US012709743B2

(12) United States Patent
Lai et al.

(10) Patent No.: US 12,709,743 B2

(45) Date of Patent: Aug. 18, 2026

(54) COMPOSITIONS AND METHODS FOR CRISPR/CAS-BASED GENE EDITING

(71) Applicant: CHINA AGRICULTURAL UNIVERSITY, Beijing (CN)

(72) Inventors: Jinsheng Lai, Beijing (CN); Zhijia Yang, Beijing (CN); Meixia Yu, Beijing (CN); Jian Chen, Beijing (CN); Beibei Xin, Beijing (CN); Yunpeng Teng, Beijing (CN); Yueheng Zhou, Beijing (CN); Haiming Zhao, Beijing (CN); Weibin Song, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 0 days.

(21) Appl. No.: 18/990,889

(22) Filed: Dec. 20, 2024

(65) Prior Publication Data

US 2025/0368974 A1 Dec. 4, 2025

Related U.S. Application Data

(63) Continuation of application No. PCT/CN2024/116796, filed on Sep. 4, 2024.

(30) Foreign Application Priority Data

Sep. 4, 2023 (CN) ......................... 202311130084.6

(51) Int. Cl.

| | |
|---|---|
| ***C12N 9/22*** | (2006.01) |
| ***C12N 15/11*** | (2006.01) |
| ***C12Q 1/34*** | (2006.01) |
| ***C12Q 1/6823*** | (2018.01) |
| ***C12Q 1/6886*** | (2018.01) |
| ***C12Q 1/6888*** | (2018.01) |

(52) U.S. Cl.

CPC ............ *C12N 9/222* (2025.05); *C12N 15/111* (2013.01); *C12Q 1/34* (2013.01); *C12Q 1/6823* (2013.01); *C12Q 1/6886* (2013.01); *C12Q 1/6888* (2013.01); *C07K 2319/09* (2013.01); *C07K 2319/40* (2013.01); *C12N 2310/20* (2017.05); *G01N 2333/922* (2013.01)

(58) Field of Classification Search

None

See application file for complete search history.

(56) References Cited

FOREIGN PATENT DOCUMENTS

| | | | |
|---|---|---|---|
| CN | 112105728 | A | 12/2020 |
| CN | 113462672 | A | 10/2021 |
| CN | 113930410 | A | 1/2022 |
| CN | 113930411 | A | 1/2022 |
| CN | 113930412 | A | 1/2022 |
| CN | 113930413 | A | 1/2022 |
| WO | WO2019201331 | A1 | 10/2019 |
| WO | WO2019214604 | A1 | 11/2019 |
| WO | WO2020088450 | A1 | 5/2020 |
| WO | WO2020098772 | A1 | 5/2020 |
| WO | WO 2023115012 | A2 | 6/2023 |

OTHER PUBLICATIONS

Accession BGY87753. Dec. 26, 2019 (Year: 2019).*
Accession BGY87826. Dec. 26, 2019 (Year: 2019).*
Accession BOJ69197. Feb. 8, 2024. (Year: 2024).*
International Search Report for International Patent Application No. PCT/CN2024/116796 dated Dec. 23, 2023, 6 pages. (English Translation).
Written Opinion for International Patent Application No. PCT/CN2024/116796 dated Dec. 16, 2023, 5 pages. (English Translation).
Yan, Winston X et al. "Cas13d Is a Compact RNA-Targeting Type VI CRISPR Effector Positively Modulated by a WYL-Domain-Containing Accessory Protein." Molecular cell vol. 70,2 (2018): 327-339.e5. doi:10.1016/j.molcel.2018.02.028.
Yan, Winston X et al. "Functionally diverse type V CRISPR-Cas systems." Science (New York, N.Y.) vol. 363,6422 (2019): 88-91. doi:10.1126/science.aav7271.
Chinese Patent and Trademark Office, First Examination Opinion Notification for Chinese Application No. 202411237279.5, issued Mar. 31, 2025. English translation (12 pages).
Chinese Patent and Trademark Office, Notice of Grant of Invention Patent Right for Chinese Application No. 202411237279.5, issued Jul. 1, 2025. English translation (8 pages).
Wang, Fangyuan et al. "Application of genome engineering in medical synthetic biology." Sheng wu gong cheng xue bao = Chinese journal of biotechnology vol. 33,3 (2017): 422-435. doi:10.13345/j.cjb.160420.
Yin, Yu-peng et al. "Application of CRISPR/Cas9 genome editing technique in cancer." J. Med Postgra, vol. 31 No. 2, Feb. 2018.
International Preliminary Report on Patentability for International Patent Application No. PCT/CN2024/116796, issued Mar. 4, 2026. English translation (12 pages).
Partial Supplementary European Search Report issued in European Application No. 24861988.4 on May 20, 2026. (13 pages).

* cited by examiner

*Primary Examiner* — Christian L Fronda

(74) *Attorney, Agent, or Firm* — Morgan, Lewis & Bockius LLP

(57) ABSTRACT

The present invention relates to the field of nucleic acid editing, in particular to the field of clustered regularly interspaced short palindromic repeat (CRISPR) technology. Specifically, the present invention relates to Cas effector proteins, fusion proteins comprising such proteins, and nucleic acid molecules encoding them. The present invention also relates to complexes and compositions for nucleic acid editing (e.g., gene or genome editing), which comprise the proteins or fusion proteins of the present invention, or nucleic acid molecules encoding them. The present invention also relates to a method for nucleic acid editing (e.g., gene or genome editing), which uses the proteins or fusion proteins comprising the present invention.

9 Claims, 6 Drawing Sheets

Specification includes a Sequence Listing.

COMPOSITIONS AND METHODS FOR CRISPR/CAS-BASED GENE EDITING

CROSS-REFERENCE-RELATED APPLICATIONS

The present application is a continuation of International Application No. PCT/CN2024/116796, filed Sep. 4, 2024, which claims the priority of Chinese patent application No. 202311130084.6 filed on Sep. 4, 2023, and the entire contents of the patent applications are incorporated herein by reference in their entirety.

SEQUENCE LISTING

The instant application contains a Sequence Listing which has been submitted electronically in XML file format and is hereby incorporated by reference in its entirety. Said XML file, created on Dec. 17, 2024, is named IEC240568PUS_Sequence Listing.xml and is 82,362 bytes in size.

TECHNICAL FIELD

The present invention relates to nucleic acid editing, particularly the field of regularly clustered interspaced short palindromic repeats (CRISPR) technology. Specifically, the present invention relates to Cas effector proteins, fusion proteins comprising such proteins, and nucleic acid molecules encoding them. The present invention also relates to complexes and compositions for nucleic acid editing (e.g., gene or genome editing), which comprise proteins or fusion proteins of the present invention or nucleic acid molecules encoding them. The present invention also relates to methods for nucleic acid editing (e.g., gene or genome editing), which use proteins or fusion proteins comprising those of the present invention.

BACKGROUND

CRISPR/Cas technology is a widely used gene editing technique that utilizes biological non-homologous end joining or homologous recombination to perform site-directed gene editing by specifically binding to target sequences on the genome through RNA guidance and cutting the DNA to produce double-strand breaks.

CRISPR/Cas9 system is the most commonly used type II CRISPR system, which recognizes 3'-NGG PAM motifs and performs blunt-end cutting on the target sequences. CRISPR/Cas Type V system is a newly discovered CRISPR system in the last two years, which has a 5'-TTN motif and performs sticky-end cutting on the target sequence, and examples include Cpf1, C2c1, CasX, and CasY. However, different CRISPR/Cas currently have distinct advantages and disadvantages. For example, Cas9, C2c1, and CasX all require two RNAs for guide RNA, while Cpf1 requires only one guide RNA and can be used for multiple gene editing. CasX has a size of 980 amino acids, while the common Cas9, C2c1, CasY, and Cpf1 are usually around 1300 amino acids in size. In addition, the PAM sequences of Cas9, Cpf1, CasX, and CasY are relatively complex and diverse. At the same time, C2c1 recognizes a rigorous 5'-TTN, so its target site is easier to predict than other systems, thereby reducing potential off-target effects.

In summary, given that currently available CRISPR/Cas systems are limited by some shortcomings, developing a new CRISPR/Cas system that is more robust and has good performance in many aspects is of great significance to the development of biotechnology.

CONTENTS OF THE INVENTION

After extensive experiments and repeated explorations, the inventor of the present application unexpectedly discovered a new type of RNA-guided endonuclease. The inventors then developed a new CRISPR/Cas system and a gene editing method based on this system.

Cas Effector Protein

Therefore, in the first aspect, the present invention provides a protein having an amino acid sequence as set forth in any one of SEQ ID NOs: 1, 2, and 3 or ortholog, homolog, variant, functional fragment thereof; wherein the ortholog, homolog, variant or functional fragment substantially retain the biological function of the sequence from which it is derived.

In the present invention, the biological function of the above sequence includes, but is not limited to, the activity of binding to a guide RNA, the activity of endonuclease, and the activity of binding to and cutting a specific site of a target sequence under the guidance of a guide RNA.

In certain embodiments, the ortholog, homolog, variant has a sequence identity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% as compared to the sequence from which it is derived.

In certain embodiments, the ortholog, homolog, variant has a sequence identity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% as compared to the sequence as set forth in any one of SEQ ID NO: 1, 2, and 3, and substantially retains the biological function of the sequence from which it is derived (e.g., the activity of binding to a guide RNA, the activity of endonuclease, the activity of binding to and cutting a specific site of a target sequence under the guidance of a guide RNA).

In certain embodiments, the protein is an effector protein in a CRISPR/Cas system.

In certain embodiments, the protein of the present invention comprises or consists of a sequence selected from the following:

(i) a sequence as set forth in any one of SEQ ID NOs: 1, 2, and 3;

(ii) a sequence having a substitution, deletion, or addition of one or more amino acids (e.g., a substitution, deletion, or addition of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 amino acids) as compared to the sequence as set forth in any one of SEQ ID NOs: 1, 2, and 3; or (iii) a sequence having a sequence identity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% as compared to the sequence as set forth in any one of SEQ ID NOs: NO: 1, 2, and 3.

Truncated Protein

In a second aspect, the present invention provides a truncated protein, in which the truncated protein has a truncation of one or more amino acids (e.g., 1 to 10, 11 to 20, 21 to 30, 31 to 40, 41 to 50, 51 to 60, or more amino acids) at the N-terminal and/or C-terminal as compared to the protein described in the first aspect.

In certain embodiments, the truncated protein has a truncation of 31 amino acids at the N-terminal as compared to the protein described in the first aspect.

In certain embodiments, the truncated protein has a truncation of 31 amino acids at the N-terminal as compared to the sequence as set forth in any one of SEQ ID NO: 1 and 2.

In certain embodiments, the term "a truncation of 31 amino acids at the N-terminal" refers to truncating 31 amino acids consecutively from the starting amino acid at the N-terminal.

In certain embodiments, the truncated protein comprises or consists of a sequence selected from the following:

(i) a sequence as set forth in SEQ ID NO: 3;

(ii) a sequence having a substitution, deletion, or addition of one or more amino acids (e.g., a substitution, deletion, or addition of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40 amino acids) as compared to the sequence as set forth in SEQ ID NO: 3; or (iii) a sequence having a sequence identity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% as compared to the sequence as set forth in SEQ ID NO: 3.

In certain embodiments, the truncated protein has the amino acid sequence as set forth in SEQ ID NO: 3.

Derivatized Protein

The protein or truncated protein of the present invention can be derivatized, for example, connected to another molecule (e.g., another polypeptide or protein). Generally, the derivatization (e.g., labeling) of a protein does not adversely affect the desired activity of the protein (e.g., activity of binding to a guide RNA, activity of endonuclease, activity of binding to and cutting a specific site of a target sequence under the guidance of a guide RNA). Therefore, the protein of the present invention is also intended to include such derivatized forms. For example, the protein of the present invention can be functionally connected (by chemical coupling, gene fusion, non-covalent connection or other means) to one or more other molecular groups, such as another protein or polypeptide, a detection agent, a pharmaceutical agent, etc.

In particular, the protein of the present invention can be linked to another functional unit. For example, it can be linked to a nuclear localization signal (NLS) sequence to improve the ability of the protein of the present invention to enter the cell nucleus. For example, it can be linked to a targeting moiety to endow the protein of the present invention with targeting ability. For example, it can be linked to a detectable label to facilitate the detection of the protein of the present invention. For example, it can be linked to an epitope tag to facilitate the expression, detection, tracing and/or purification of the protein of the present invention.

Conjugate

Therefore, in a third aspect, the present invention provides a conjugate, which comprises the protein or truncated protein as described above and a modified moiety.

In certain embodiments, the modified moiety is selected from the group consisting of an additional protein or polypeptide, a detectable label, and any combination thereof.

In certain embodiments, the additional protein or polypeptide is selected from the group consisting of an epitope tag, a reporter gene sequence, a nuclear localization signal (NLS) sequence, a targeting moiety, a transcriptional activation domain (e.g., VP64), a transcriptional repression domain (e.g., a KRAB domain or a SID domain), a nuclease domain (e.g., Fok1), a domain having an activity selected from the following: nucleotide deaminase, methylase activity, demethylase, transcriptional activation activity, transcriptional repression activity, transcriptional release factor activity, histone modification activity, nuclease activity, single-stranded RNA cleavage activity, double-stranded RNA cleavage activity, single-stranded DNA cleavage activity, double-stranded DNA cleavage activity and nucleic acid binding activity, and any combination thereof.

In certain embodiments, the conjugate of the present invention comprises one or more NLS sequences, such as a NLS of large T antigen of SV40 virus. In certain exemplary embodiments, the NLS sequence is set forth in SEQ ID NO: 27. In certain embodiments, the NLS sequence is located at, near or close to the end (e.g., N-terminal or C-terminal) of the protein or truncated protein of the present invention. In certain exemplary embodiments, the NLS sequence is located at, near, or close to the C-terminal of the protein or truncated protein of the present invention.

In certain embodiments, the conjugate of the present invention comprises an epitope tag. Such epitope tags are well known to those skilled in the art, and examples thereof include but are not limited to, His, V5, FLAG, HA, Myc, VSV to G, Trx, etc., and those skilled in the art know how to select a suitable epitope tag according to the desired purpose (e.g., purification, detection or tracing).

In certain embodiments, the conjugate of the present invention comprises a reporter gene sequence. Such reporter genes are well known to those skilled in the art, and examples thereof include but are not limited to, GST, HRP, CAT, GFP, HcRed, DsRed, CFP, YFP, BFP, etc.

In certain embodiments, the conjugate of the present invention comprises a domain capable of binding to a DNA molecule or an intracellular molecule, such as a maltose binding protein (MBP), a DNA binding domain (DBD) of Lex A, a DBD of GAL4, etc.

In certain embodiments, the conjugate of the present invention comprises a detectable label, such as a fluorescent dye, such as FITC or DAPI.

In certain embodiments, the protein or truncated protein of the present invention is coupled, conjugated, or fused to the modification portion optionally via a linker.

In certain embodiments, the modification portion is directly connected to the N-terminal or C-terminal of the protein or truncated protein of the present invention.

In certain embodiments, the modification portion is connected to the N-terminal or C-terminal of the protein or truncated protein of the present invention via a linker. Such linkers are well known in the art, and examples thereof include but are not limited to, linkers comprising one or more (e.g., 1, 2, 3, 4 or 5) amino acids (e.g., Glu or Ser) or amino acid derivatives (e.g., Ahx, β-Ala, GABA or Ava), or PEG, etc.

Fusion Protein

In a fourth aspect, the present invention provides a fusion protein, which comprises the protein described in the first aspect or the truncated protein described in the second aspect and an additional protein or polypeptide.

In certain embodiments, the additional protein or polypeptide is selected from the group consisting of an epitope tag, a reporter gene sequence, a nuclear localization signal (NLS) sequence, a targeting moiety, a transcriptional activation domain (e.g., VP64), a transcriptional repression domain (e.g., a KRAB domain or a SID domain), a nuclease domain (e.g., Fok1), a domain having an activity selected from the following: nucleotide deaminase, methylase activity, demethylase, transcriptional activation activity, transcriptional repression activity, transcriptional release factor activity, histone modification activity, nuclease activity, single-stranded RNA cleavage activity, double-stranded RNA cleavage activity, single-stranded DNA cleavage activity, double-stranded DNA cleavage activity and nucleic acid binding activity, and any combination thereof.

In certain embodiments, the fusion protein of the present invention comprises one or more NLS sequences, such as a NLS of large T antigen of SV40 virus. In certain embodiments, the NLS sequence is located at, near or close to the end (e.g., N-terminal or C-terminal) of the protein or truncated protein of the present invention. In certain exemplary embodiments, the NLS sequence is located at, near or close to the C-terminal of the protein or truncated protein of the present invention.

In certain embodiments, the fusion protein of the present invention comprises an epitope tag.

In certain embodiments, the fusion protein of the present invention comprises a reporter gene sequence.

In certain embodiments, the fusion protein of the present invention comprises a domain capable of binding to a DNA molecule or an intracellular molecule.

In certain embodiments, the protein or truncated protein of the present invention is fused to the additional protein or polypeptide optionally via a linker.

In certain embodiments, the additional protein or polypeptide is directly connected to the N-terminal or C-terminal of the protein or truncated protein of the present invention.

In certain embodiments, the additional protein or polypeptide is connected to the N-terminal or C-terminal of the protein or truncated protein of the present invention via a linker.

In certain exemplary embodiments, the fusion protein of the present invention has an amino acid sequence as set forth in any one of SEQ ID NOs: 28 to 30.

The protein of the present invention, the conjugate of the present invention or the fusion protein of the present invention is not limited by the production method thereof, for example, it can be produced by a genetic engineering method (recombinant technology) or by a chemical synthesis method.

Direct Repeat Sequence

In the fifth aspect, the present invention provides an isolated nucleic acid molecule, which comprises or consists of a sequence selected from the following sequences:

(i) a sequence as set forth in any one of SEQ ID NOs: 7, 8, 9, 10, 11, 12, 13, 14, 15 or 16;

(ii) a sequence having a substitution, deletion or addition of one or more bases (e.g., a substitution, deletion or addition of 1, 2, 3, 4, 5, 6, 7, 8, 9 or 10 bases) as compared to the sequence as set forth in any one of SEQ ID NOs: 7, 8, 9, 10, 11, 12, 13, 14, 15 or 16;

(iii) a sequence having a sequence identity of at least 20%, at least 30%, at least 40%, at least 50%, at least 60%, at least 70%, at least 80%, at least 90%, at least 95% as compared to the sequence as set forth in any one of SEQ ID NOs: 7, 8, 9, 10, 11, 12, 13, 14, 15 or 16;

(iv) a sequence capable of hybridizing with the sequence as described in any one of (i) to (iii) under a stringent condition; or (v) a complementary sequence of the sequence as described in any one of (i) to (iii);

and, the sequence as described in any one of (ii) to (v) substantially retains the biological function of the sequence from which it is derived, and the biological function of the sequence refers to the activity as a direct repeat sequence in the CRISPR-Cas system.

In certain embodiments, the isolated nucleic acid molecule is a direct repeat sequence in the CRISPR-Cas system.

In certain embodiments, the nucleic acid molecule comprises a sequence selected from the following, or consists of a sequence selected from the following:

(a) a nucleotide sequence as set forth in any one of SEQ ID NOs: 7, 8, 9, 10, 11, 12, 13, 14, 15 or 16;

(b) a sequence capable of hybridizing with the sequence as described in (a) under a stringent condition; or (c) a complementary sequence of the sequence as described in (a).

In certain embodiments, the isolated nucleic acid molecule is an RNA. In certain embodiments, the isolated nucleic acid molecule is a direct repeat sequence in the CRISPR/Cas system.

CRISPR/Cas Complex

In a sixth aspect, the present invention provides a complex, which comprises:

(i) a protein component, which is selected from the group consisting of the protein, truncated protein, conjugate or fusion protein of the present invention, and any combination thereof; and (ii) a nucleic acid component, which comprises, from the 5' to 3' direction, the isolated nucleic acid molecule as described above and a guide sequence capable of hybridizing with a target sequence, wherein the protein component and the nucleic acid component bind to each other to form a complex.

In some embodiments, the guide sequence is ligated to the 3' end of the nucleic acid molecule.

In some embodiments, the guide sequence comprises a complementary sequence to the target sequence.

In some embodiments, the nucleic acid component is a guide RNA in a CRISPR-Cas system.

In some embodiments, the nucleic acid molecule is an RNA.

In some embodiments, the complex does not comprise a trans-activating crRNA (tracrRNA).

In some embodiments, the guide sequence has a length of at least 5, at least 10, at least 15, at least 20, at least 25, at least 30 nucleotides. In some embodiments, the guide sequence has a length of 10 to 30, or 15 to 25, or 15 to 22, or 19 to 25, or 19 to 22 nucleotides.

In some embodiments, the isolated nucleic acid molecule has a length of 55 to 70 nucleotides, such as 55 to 65 nucleotides, such as 60 to 65 nucleotides, such as 62 to 65 nucleotides, such as 63 to 64 nucleotides. In some embodiments, the isolated nucleic acid molecule has a length of 15 to 30 nucleotides, such as 15 to 25 nucleotides, such as 20 to 25 nucleotides, such as 22 to 24 nucleotides, such as 23 nucleotides.

Encoding Nucleic Acid, Vector and Host Cell

In the seventh aspect, the present invention provides an isolated nucleic acid molecule, which comprises:

(i) a nucleotide sequence encoding the protein, truncated protein or fusion protein of the present invention;

(ii) a nucleotide sequence encoding the isolated nucleic acid molecule as described in the fifth aspect; or (iii) a nucleotide sequence comprising (i) and (ii).

In some embodiments, the nucleotide sequence as described in any one of (i) to (iii) is optimized with a codon for expression in prokaryotic cells. In some embodiments, the nucleotide sequence as described in any one of (i) to (iii) is optimized with a codon for expression in eukaryotic cells.

In the eighth aspect, the present invention also provides a vector, which comprises the isolated nucleic acid molecule as described in the seventh aspect. The vector of the present invention can be a cloning vector or an expression vector. In certain embodiments, the vector of the present invention is, for example, a plasmid, a cosmid, a phage, a Kos plasmid, and the like. In certain embodiments, the vector is capable of expressing the protein, truncated protein, fusion protein, isolated nucleic acid molecule as described in the fifth aspect, or the complex as described in the sixth aspect of the present invention in a subject (e.g., a mammal, such as a human).

In the ninth aspect, the present invention also provides a host cell comprising the isolated nucleic acid molecule or vector as described above. Such host cells include, but are not limited to, prokaryotic cells such as *Escherichia coli* cells, and eukaryotic cells such as yeast cells, insect cells, plant cells (e.g., cassava, corn, sorghum, soybean, wheat, oat or rice cells) and animal cells (e.g., mammalian cells, such as mouse cells, human cells, etc.). The cell of the present invention can also be a cell line, such as a 293T cell.

Composition and Vector Composition

In the tenth aspect, the present invention also provides a composition, which comprises:

(i) a first component, which is selected from the group consisting of the protein, truncated protein, conjugate, fusion protein of the present invention, or a nucleotide sequence encoding the protein, truncated protein or fusion protein, and any combination thereof; and (ii) a second component, which is a nucleotide sequence comprising a guide RNA, or a nucleotide sequence encoding the nucleotide sequence comprising the guide RNA;

wherein, the guide RNA comprises a direct repeat sequence and a guide sequence from the 5' to 3' direction, and the guide sequence is capable of hybridizing with a target sequence;

the guide RNA is capable of forming a complex with the protein, truncated protein, conjugate or fusion protein as described in (i).

In certain embodiments, the direct repeat sequence is the isolated nucleic acid molecule as defined in the fifth aspect.

In certain embodiments, the guide sequence is ligated to the 3' end of the direct repeat sequence. In certain embodiments, the guide sequence comprises a complementary sequence of the target sequence.

In certain embodiments, the composition does not comprise a trans-activating crRNA (tracrRNA).

In certain embodiments, the composition is non-naturally occurring or modified. In certain embodiments, at least one component of the composition is non-naturally occurring or modified. In certain embodiments, the first component is non-naturally occurring or modified; and/or, the second component is non-naturally occurring or modified.

In certain embodiments, when the target sequence is DNA, the target sequence is located at the 3' end of the protospacer adjacent motif (PAM), and the PAM has a sequence shown as 5'-RYR, wherein R is selected from A or G, and Y is selected from T or C. In certain embodiments, the sequence of the PAM is selected from the group consisting of ATG, ACG, GTG, ATA, ACA, GCA, GTA and/or GCG.

In certain embodiments, when the target sequence is RNA, the target sequence does not have a PAM domain restriction.

In certain embodiments, the target sequence is a DNA or RNA sequence from a prokaryotic cell or a eukaryotic cell. In certain embodiments, the target sequence is a non-naturally occurring DNA or RNA sequence.

In certain embodiments, the target sequence is present in a cell. In certain embodiments, the target sequence is present in the nucleus or the cytoplasm (e.g., an organelle). In certain embodiments, the cell is a eukaryotic cell. In certain embodiments, the cell is a prokaryotic cell.

In certain embodiments, the protein or truncated protein is linked to one or more NLS sequences. In certain embodiments, the conjugate or fusion protein comprises one or more NLS sequences. In certain embodiments, the NLS sequence is linked to the N-terminal or C-terminal of the protein. In certain embodiments, the NLS sequence is fused to the N-terminal or C-terminal of the protein.

In the eleventh aspect, the present invention also provides a composition, which comprises one or more vectors, wherein the one or more vectors comprise:

(i) a first nucleic acid, which comprises a nucleotide sequence encoding the protein, truncated protein or fusion protein of the present invention; optionally, the first nucleic acid is operably linked to a first regulatory element; and (ii) a second nucleic acid, which comprises a nucleotide sequence encoding a guide RNA; optionally, the second nucleic acid is operably linked to a second regulatory element;

wherein:

the first nucleic acid and the second nucleic acid are present on the same vector or different vectors;

the guide RNA comprises a direct repeat sequence and a guide sequence from the 5' to 3' direction, and the guide sequence is capable of hybridizing with a target sequence;

the guide RNA is capable of forming a complex with the protein, truncated protein or fusion protein as described in (i).

In certain embodiments, the direct repeat sequence is an isolated nucleic acid molecule as defined in the fifth aspect.

In certain embodiments, the guide sequence is linked to the 3' end of the direct repeat sequence. In certain embodiments, the guide sequence comprises a complementary sequence of the target sequence.

In certain embodiments, the composition does not comprise a trans-activating crRNA (tracrRNA).

In certain embodiments, the composition is non-naturally occurring or modified. In some embodiments, at least one component of the composition is non-naturally occurring or modified.

In some embodiments, the first regulatory element is a promoter, such as an inducible promoter.

In some embodiments, the second regulatory element is a promoter, such as an inducible promoter.

In some embodiments, when the target sequence is DNA, the target sequence is located at the 3' end of the protospacer adjacent motif (PAM), and the PAM has a sequence shown as 5'-RYR, wherein R is A or G, and Y is T or C.

In some embodiments, the sequence of the PAM is selected from the group consisting of ATG, ACG, GTG, ATA, ACA, GCA, GTA and/or GCG.

In some embodiments, when the target sequence is RNA, and the target sequence does not have a PAM domain restriction.

In some embodiments, the target sequence is a DNA or RNA sequence from a prokaryotic cell or a eukaryotic cell.

In some embodiments, the target sequence is a non-naturally occurring DNA or RNA sequence.

In some embodiments, the target sequence is present in a cell. In certain embodiments, the target sequence is present in the nucleus or the cytoplasm (e.g., an organelle). In certain embodiments, the cell is a eukaryotic cell. In certain embodiments, the cell is a prokaryotic cell.

In certain embodiments, the protein is linked to one or more NLS sequences. In certain embodiments, the conjugate or fusion protein comprises one or more NLS sequences. In certain embodiments, the NLS sequence is linked to the N-terminal or C-terminal of the protein. In certain embodiments, the NLS sequence is fused to the N-terminal or C-terminal of the protein.

In certain embodiments, one type of vector is a plasmid, which refers to a circular double-stranded DNA loop into which an additional DNA fragment can be inserted, for example, by standard molecular cloning techniques. Another type of vector is a viral vector, in which a virally derived DNA or RNA sequence is present in a vector for packaging a virus (e.g., a retrovirus, a replication-defective retrovirus, an adenovirus, a replication-defective adenovirus, and an adeno-associated virus). The viral vector further comprises a polynucleotide carried by a virus for transfection into a host cell. Certain vectors (e.g., bacterial vectors with bacterial replication origin, and episomal mammalian vectors) are capable of autonomous replication in host cells into which they are introduced. Other vectors (e.g., non-episomal mammalian vectors) are integrated into the genome of a host cell upon introduction into the host cell and are thereby replicated along with the host genome. Moreover, certain vectors are capable of directing the expression of genes to which they are operably linked. Such vectors are referred to herein as “expression vectors”. Common expression vectors used in recombinant DNA technology are generally in the form of plasmids.

The recombinant expression vector may comprise the nucleic acid molecule of the present invention in a form suitable for nucleic acid expression in a host cell, meaning that such recombinant expression vector comprises one or more regulatory elements selected based on the host cell to be used for expression, and the regulatory elements are operably linked to the nucleic acid sequence to be expressed.

Delivery and Delivery Composition

The protein of the present invention, the truncated protein of the present invention, the conjugate of the present invention, the fusion protein of the present invention, the isolated nucleic acid molecule as described in the fifth aspect, the complex of the present invention, the isolated nucleic acid molecule as described in the seventh aspect, the vector as described in the eighth aspect, and the composition as described in the tenth and eleventh aspects of the present invention may be delivered by any method known in the art. Such methods include but are not limited to, electroporation, lipofection, nucleofection, microinjection, sonoporation, gene gun, calcium phosphate-mediated transfection, cationic transfection, liposome transfection, dendritic transfection, heat shock transfection, nucleofection, magnetofection, lipofection, puncture transfection, optical transfection, agent-enhanced nucleic acid uptake, and delivery via liposome, immunoliposome, viral particle, artificial virion, etc.

Therefore, in the twelfth aspect, the present invention provides a delivery composition, which comprises a delivery vector, and one or more selected from the following: the protein, truncated protein, conjugate, fusion protein, isolated nucleic acid molecule as described in the fifth aspect, the complex of the present invention, the isolated nucleic acid molecule as described in the seventh aspect, the vector as described in the eighth aspect, and the composition as described in the tenth aspect and the eleventh aspect.

In some embodiments, the delivery vector is a particle.

In some embodiments, the delivery vector is selected from the group consisting of lipid particle, sugar particle, metal particle, protein particle, liposome, exosome, microvesicle, gene gun, or viral vector (e.g., replication-defective retrovirus, lentivirus, adenovirus, or adeno-associated virus).

Kit

In another aspect, the present invention provides a kit, which comprises one or more of the components described above. In certain embodiments, the kit comprises one or more components selected from the following: the protein of the present invention, the truncated protein of the present invention, the conjugate of the present invention, the fusion protein of the present invention, the isolated nucleic acid molecule as described in the fifth aspect, the complex of the present invention, the isolated nucleic acid molecule as described in the seventh aspect, the vector as described in the eighth aspect, and the composition as described in the tenth and eleventh aspects of the present invention.

In certain embodiments, the kit of the present invention comprises the composition as described in the tenth aspect. In certain embodiments, the kit further comprises instructions for using the composition.

In certain embodiments, the kit of the present invention comprises the composition as described in the eleventh aspect. In certain embodiments, the kit further comprises instructions for using the composition.

In certain embodiments, the components contained in the kit of the present invention can be provided in any suitable container.

In certain embodiments, the kit further comprises one or more buffers. The buffers can be any buffer, including but not limited to sodium carbonate buffer, sodium bicarbonate buffer, borate buffer, Tris buffer, MOPS buffer, HEPES buffer, and combinations thereof. In certain embodiments, the buffer is alkaline. In certain embodiments, the buffer has a pH of about 7 to about 10.

In certain embodiments, the kit further comprises one or more oligonucleotides, and one or more oligonucleotides correspond to a guide sequence for insertion into a vector to operably link the guide sequence and the regulatory element. In certain embodiments, the kit comprises a homologous recombination template polynucleotide.

Method and Use

In another aspect, the present invention provides a method to modify a target gene, which comprises: contacting the complex of the present invention, the composition as described in the tenth aspect and the eleventh aspect with the target gene, or delivering it to a cell containing the target gene; wherein the target sequence is present in the target gene.

In some embodiments, the method is used for modifying the target gene in vitro or ex vivo. In some embodiments, the method is not a method for treating a human or animal via therapy. In some embodiments, the method does not comprise a step of modifying a human germline genetic characteristic.

In some embodiments, the target gene is present in a cell. In some embodiments, the cell is a prokaryotic cell. In some embodiments, the cell is a eukaryotic cell. In some embodiments, the cell is a mammalian cell. In some embodiments, the cell is a human cell. In some embodiments, the cell is selected from the group consisting of non-human cell primate cell, bovine cell, porcine cell or rodent cell. In some embodiments, the cell is a non-mammalian eukaryotic cell, such as poultry or fish cell. In some embodiments, the cell is a plant cell, such as a cell of a cultivated plant (e.g., cassava, corn, sorghum, wheat or rice), algae, tree or vegetable.

In some embodiments, the target gene is present in a nucleic acid molecule (e.g., a plasmid) in vitro. In some embodiments, the target gene is present in a plasmid.

In some embodiments, the method results in a breakage in the target sequence (e.g., a double-strand breakage in DNA or a single-strand breakage in RNA). In some embodiments, the breakage results in a reduced transcription of the target gene.

In some embodiments, the method further comprises: contacting an editing template (e.g., an exogenous nucleic acid) with the target gene, or delivering it to a cell comprising the target gene. In such embodiments, the method repairs the broken target gene by homologous recombination with an editing template (e.g., an exogenous nucleic acid), wherein the repair results in a mutation comprising an insertion, deletion, or substitution of one or more nucleotides of the target gene. In some embodiments, the mutation results in one or more amino acid changes in a protein expressed from a gene comprising the target sequence.

Thus, in some embodiments, the modification further comprises inserting an editing template (e.g., an exogenous nucleic acid) into the breakage.

In certain embodiments, the protein, truncated protein, conjugate, fusion protein, isolated nucleic acid molecule, complex, vector or composition is contained in a delivery vehicle.

In certain embodiments, the delivery vehicle is selected from the group consisting of lipid particles, sugar particles, metal particles, protein particles, liposomes, exosomes, viral vectors (e.g., replication-defective retroviruses, lentiviruses, adenoviruses or adeno-associated viruses).

In certain embodiments, the method is used to modify a cell, cell line or organism by changing one or more target sequences in a target gene or a nucleic acid molecule encoding a target gene product.

In another aspect, the present invention provides a method for changing the expression of a gene product, which comprises: contacting the complex of the present invention, the composition as described in the tenth aspect and the eleventh aspect with a nucleic acid molecule encoding the gene product, or delivering it to a cell comprising the nucleic acid molecule; wherein the target sequence is present in the nucleic acid molecule.

In certain embodiments, the method is used to change the expression of a gene product in vitro or ex vivo. In certain embodiments, the method is not a method for treating a human or animal by therapy. In certain embodiments, the method does not comprise a step of modifying a human germline genetic characteristic.

In certain embodiments, the nucleic acid molecule is present in a cell. In some embodiments, the cell is a prokaryotic cell. In some embodiments, the cell is a eukaryotic cell. In some embodiments, the cell is a mammalian cell. In some embodiments, the cell is a human cell. In some embodiments, the cell is selected from the group consisting of non-human primate cell, bovine cell, porcine cell or rodent cell. In some embodiments, the cell is a non-mammalian eukaryotic cell, such as poultry or fish cell. In some embodiments, the cell is a plant cell, such as a cell of a cultivated plant (e.g., cassava, corn, sorghum, wheat or rice), algae, tree or vegetable.

In some embodiments, the nucleic acid molecule is present in a nucleic acid molecule (e.g., a plasmid) in vitro. In some embodiments, the nucleic acid molecule is present in a plasmid.

In some embodiments, the expression of the gene product is altered (e.g., enhanced or reduced). In some embodiments, the expression of the gene product is enhanced. In some embodiments, the expression of the gene product is reduced.

In some embodiments, the gene product is a protein.

In certain embodiments, the protein, truncated protein, conjugate, fusion protein, isolated nucleic acid molecule, complex, vector or composition is contained in a delivery vehicle.

In certain embodiments, the delivery vehicle is selected from the group consisting of lipid particles, sugar particles, metal particles, protein particles, liposomes, exosomes, viral vectors (e.g., replication-defective retroviruses, lentiviruses, adenoviruses or adeno-associated viruses).

In certain embodiments, the method is used for modifying a cell, a cell line or an organism by changing one or more target sequences in a target gene or a nucleic acid molecule encoding a target gene product.

In another aspect, the present invention relates to a use of the protein as described in the first aspect, the truncated protein as described in the second aspect, the conjugate as described in the third aspect, the fusion protein as described in the fourth aspect, the isolated nucleic acid molecule as described in the fifth aspect, the complex as described in the sixth aspect, the isolated nucleic acid molecule as described in the seventh aspect, the vector as described in the eighth aspect, the composition as described in the tenth aspect, the composition as described in the eleventh aspect, the kit of the present invention, in the manufacture of a preparation, in which the preparation is used for nucleic acid editing (e.g., in vitro or ex vivo nucleic acid editing).

In certain embodiments, the nucleic acid to be edited is present in a cell. In some embodiments, the cell is a prokaryotic cell or a eukaryotic cell. In some embodiments, the nucleic acid to be edited is present in a nucleic acid molecule (e.g., a plasmid) in vitro.

In some embodiments, the nucleic acid editing comprises gene or genome editing, such as modifying a gene, knocking out a gene, changing the expression of a gene product, repairing a mutation, and/or inserting a polynucleotide. In some embodiments, the gene or genome editing does not comprise a step of modifying a human germline genetic characteristic. In some embodiments, the use is not a method of treating a human or animal by therapy.

In some embodiments, the use further comprises repairing the edited target sequence by homologous recombination with an exogenous template polynucleotide, wherein the repair can produce a mutation of the target sequence, which comprises an insertion, deletion, or substitution of one or more nucleotides.

In another aspect, the present invention relates to a use of the protein as described in the first aspect, the truncated protein as described in the second aspect, the conjugate as described in the third aspect, the fusion protein as described in the fourth aspect, the isolated nucleic acid molecule as described in the fifth aspect, the complex as described in the sixth aspect, the isolated nucleic acid molecule as described in the seventh aspect, the vector as described in the eighth aspect, the composition as described in the tenth aspect, the composition as described in the eleventh aspect, the kit of the present invention, in the manufacture of a preparation, in which the preparation is used for: (i) in vitro or ex vivo DNA detection; (ii) editing a target sequence in a target locus to modify an organism or a non-human organism (e.g., a prokaryotic organism).

In certain embodiments, the preparation is used for the detection of single-stranded DNA or double-stranded DNA (e.g., detection of single-stranded or double-stranded DNA in a prokaryotic cell).

In certain embodiments, the DNA detection is used to detect a tumor, a virus or a bacterium. Without being limited by theory, it is believed that due to the non-specific cleavage characteristics of Casδ protein on single-stranded DNA after target DNA recognition, when a target DNA (e.g., a tumor-specific label, virus or bacterium-specific label) is present, it is possible to achieve the detection of tumor, Ebola virus, avian influenza virus, African swine fever virus and other viruses or bacteria by adding a detectable single-stranded DNA and detecting the non-specific cleavage of the single-stranded DNA.

On the other hand, the present invention also provides a method for detecting whether a target nucleic acid is present in a sample, which comprises the following steps:

(1) contacting the sample with a labeled DNA probe and any of the following components: the complex of the present invention, the composition as described in the tenth aspect or the eleventh aspect, or the kit of the present invention;

wherein, the guide sequence contained in the complex, composition or kit is capable of hybridizing with the target nucleic acid, and the DNA probe does not hybridize with the guide sequence;

in certain embodiments, the DNA probe emits a detectable signal after being cleaved;

(2) detecting the detectable signal generated by the cleavage of DNA probes by the protein or truncated protein contained in the complex, composition or kit cleaves the DNA probe, thereby determining whether the target nucleic acid is present in the sample.

In some embodiments, one end (e.g., 5' end) of the DNA probe is labeled with a fluorescent group, and the other end (e.g., 3' end) is labeled with a quenching group.

In some embodiments, the sequence of the target nucleic acid is a sequence obtained from a pathogen. In some embodiments, the pathogen is selected from the group consisting of a virus, a bacterium, a fungus, a protozoa, a parasite, or any combination thereof.

In some embodiments, the sequence of the target nucleic acid is obtained from the genome of a tumor cell.

The target nucleic acid detected in the present application can be a DNA or RNA. Therefore, in some embodiments, the method further comprises a step of contacting the sample with a reagent for reverse transcription. In some embodiments, the reagent for reverse transcription is selected from the group consisting of a reverse transcriptase, an oligonucleotide primer, a dNTP, or any combination thereof.

In some embodiments, the target nucleic acid is single-stranded or double-stranded. In some embodiments, the sequence of the target nucleic acid is a DNA or RNA sequence from a prokaryotic cell or a eukaryotic cell; or, the sequence of the target nucleic acid is a non-naturally occurring DNA or RNA sequence.

In some embodiments, the detectable signal is determined by one or more methods selected from the group consisting of imaging-based detection, sensor-based detection, color detection, gold nanoparticle-based detection, fluorescence polarization, colloidal phase transition/dispersion, electrochemical detection, and semiconductor-based sensing.

In some embodiments, the method further comprises a step of amplifying the target nucleic acid in the sample.

Cells and Cell Progeny

In some cases, the modification introduced into the cell by the method of the present invention may cause the cell and its progeny to be altered to improve the production of its biological product (e.g., antibody, starch, ethanol or other desired cell output). In some cases, the modification introduced into the cell by the method of the present invention may cause the cell and its progeny to comprise a change that causes a change in the produced biological product.

Therefore, in another aspect, the present invention also relates to a cell or progeny thereof obtained by the method as described above, wherein the cell comprises a modification that is not present in its wild type.

The present invention also relates to a cell product of the cell or progeny thereof as described above.

The present invention also relates to an in vitro, ex vivo or in vivo cell or cell line or progeny thereof, wherein the cell or cell line or progeny thereof comprises: the protein as described in the first aspect, the truncated protein as described in the second aspect, the conjugate as described in the third aspect, the fusion protein as described in the fourth aspect, the isolated nucleic acid molecule as described in the fifth aspect, the complex as described in the sixth aspect, the isolated nucleic acid molecule as described in the seventh aspect, the vector as described in the eighth aspect, the composition as described in the tenth aspect, and the composition as described in the eleventh aspect.

In certain embodiments, the cell is a prokaryotic cell.

In certain embodiments, the cell is a eukaryotic cell. In certain embodiments, the cell is a mammalian cell. In certain embodiments, the cell is a human cell. In certain embodiments, the cell is a non-human mammalian cell, such as a cell of a non-human primate, cow, sheep, pig, dog, monkey, rabbit, or rodent (e.g., rat or mouse). In certain embodiments, the cell is a non-mammalian eukaryotic cell, such as a cell of a poultry bird (e.g., chicken), fish or crustacean (e.g., clam, shrimp). In some embodiments, the cell is a plant cell, such as a cell of a monocot or dicot plant or a cell of a cultivated plant, or a cell of a food crop, such as cassava, corn, sorghum, soybean, wheat, oat or rice, such as algae, tree or production plant, fruit or vegetable (e.g., tree, such as citrus tree, nut tree; nightshade, cotton, tobacco, tomato, grape, coffee, cocoa, etc.).

In some embodiments, the cell is a stem cell or a stem cell line.

Definition of Terms

In the present invention, unless otherwise specified, the scientific and technical terms used herein have the meanings commonly understood by those skilled in the art. In addition, the molecular genetics, nucleic acid chemistry, chemistry, molecular biology, biochemistry, cell culture, microbiology, cell biology, genomics and recombinant DNA operation steps used herein are all conventional steps widely used in the corresponding fields. At the same time, in order to better understand the present invention, the definitions and explanations of the relevant terms are provided below.

In the present invention, the expression "Casδ" refers to a Cas effector protein first discovered and identified by the inventors, which has an amino acid sequence selected from the following:

(i) a sequence as set forth in any one of SEQ ID NOs: 1, 2, and 3;

(ii) a sequence having a substitution, deletion, or addition of one or more amino acids (e.g., a substitution, deletion, or addition of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids) as compared to the sequence as set forth in any one of SEQ ID NOs: 1, 2, and 3; or (iii) a sequence having a sequence identity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% as compared to the sequence as set forth in any one of SEQ ID NOs: 1, 2, and 3.

The Casδ of the present invention is an endonuclease that binds to and cuts a specific site of a target sequence under the guidance of a guide RNA.

As used herein, the term "clustered regularly interspaced short palindromic repeats (CRISPR)-CRISPR-associated (Cas) (CRISPR-Cas) system" or "CRISPR system" is used interchangeably and has the meaning generally understood by those skilled in the art, which generally comprises a transcription product or other element related to the expression of a CRISPR-associated ("Cas") gene, or a transcription product or other element capable of directing the activity of the Cas gene. Such transcripts or other elements may comprise sequences encoding Cas effector proteins and guide RNAs comprising CRISPR RNA (crRNA), as well as trans-activating crRNA (tracrRNA) sequences contained in the CRISPR-Cas9 system, or other sequences or transcripts from CRISPR locus. In the Casδ-CRISPR system described in the present invention, the tracrRNA sequence is not required.

As used herein, the terms "Cas effector protein" and "Cas effector enzyme" are used interchangeably and refer to any protein greater than 800 amino acids in length presented in the CRISPR-Cas system. In some cases, such protein refers to a protein identified from the Cas locus.

As used herein, the terms "guide RNA" and "mature crRNA" are used interchangeably and have the meanings commonly understood by those skilled in the art. In general, the guide RNA may comprise a direct repeat sequence and a guide sequence, or may consist essentially of or consist of a direct repeat sequence and a guide sequence (also referred to as a spacer in the context of an endogenous CRISPR system). In some cases, the guide sequence is any polynucleotide sequence that has sufficient complementarity with a target sequence to hybridize with the target sequence and guide the specific binding of the CRISPR/Cas complex to the target sequence. In certain embodiments, when optimally aligned, the degree of complementarity between the guide sequence and corresponding target sequence thereof is at least 50%, at least 60%, at least 70%, at least 80%, at least 90%, at least 95%, or at least 99%. Determining the optimal alignment is within the capabilities of a person of ordinary skill in the art. For example, there are publicly available and commercially available alignment algorithms and programs, such as, but not limited to, ClustalW, Smith-Waterman in matlab, Bowtie, Geneious, Biopython, and SeqMan.

In some cases, the guide sequence has a length of at least 5, at least 10, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, or at least 50 nucleotides. In some cases, the guide sequence has a length of no more than 50, 45, 40, 35, 30, 25, 24, 23, 22, 21, 20, 15, 10 or less nucleotides. In certain embodiments, the guide sequence has a length of 10 to 30, or 15 to 25, or 15 to 22, or 19 to 25, or 19 to 22 nucleotides.

In some cases, the direct repeat sequence has a length of at least 10, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, at least 50, at least 55, at least 56, at least 57, at least 58, at least 59, at least 60, at least 61, at least 62, at least 63, at least 64, at least 65, or at least 70 nucleotides. In some cases, the direct repeat sequence has a length of no more than 70, 65, 64, 63, 62, 61, 60, 59, 58, 57, 56, 55, 50, 45, 40, 35, 30, 29, 28, 27, 26, 25, 24, 23, 22, 21, 20, 15, 10 or less nucleotides. In certain embodiments, the direct repeat sequence has a length of 55 to 70 nucleotides, such as 55 to 65 nucleotides, such as 60 to 65 nucleotides, such as 62 to 65 nucleotides, such as 63 to 64 nucleotides. In certain embodiments, the direct repeat sequence has a length of 15 to 30 nucleotides, such as 15 to 25 nucleotides, such as 20 to 25 nucleotides, such as 22 to 24 nucleotides, such as 23 nucleotides.

As used herein, the term "CRISPR/Cas complex" refers to a ribonucleoprotein complex formed by the binding of a guide RNA or mature crRNA to a Cas protein, which comprises a guide sequence that hybridizes to a target sequence and binds to the Cas protein. The ribonucleoprotein complex is capable of recognizing and cleaving a polynucleotide capable of hybridizing to the guide RNA or mature crRNA.

Therefore, in the case of forming a CRISPR/Cas complex, a "target sequence" refers to a polynucleotide targeted by a guide sequence designed to having targeting ability, such as a sequence complementary to the guide sequence, wherein the hybridization between the target sequence and the guide sequence will promote the formation of the CRISPR/Cas complex. Complete complementarity is not required, as long as there is sufficient complementarity to cause the hybridization and promote the formation of the CRISPR/Cas complex. The target sequence may comprise any polynucleotide, such as DNA or RNA. In some cases, the target sequence is located in the nucleus or cytoplasm of a cell. In some cases, the target sequence may be located in an organelle of a eukaryotic cell, such as a mitochondria or a chloroplast. A sequence or template that can be used for a recombination into a target locus containing the target sequence is referred to as an "editing template" or "editing polynucleotide" or "editing sequence". In certain embodiments, the editing template is an exogenous nucleic acid. In certain embodiments, the recombination is a homologous recombination.

In the present invention, the expression "target sequence" or "target polynucleotide" can be any polynucleotide that is endogenous or exogenous to a cell (e.g., a eukaryotic cell). For example, the target polynucleotide can be a polynucleotide present in the nucleus of a eukaryotic cell. The target polynucleotide can be a sequence encoding a gene product (e.g., a protein) or a non-coding sequence (e.g., a regulatory polynucleotide or a useless DNA). In some cases, it is believed that the target sequence should be associated with a protospacer adjacent motif (PAM). The exact sequence and length requirements for the PAM vary depending on the Cas effector enzyme used, but the PAM is typically a sequence of 2 to 5 base pairs adjacent to the protospacer sequence (i.e., the target sequence). Those skilled in the art are able to identify the PAM sequence for use together with a given Cas effector protein. Herein, "specific motif sequence recognized by Cas protein" or "motif sequence" refers to a PAM sequence.

In some cases, the target sequence or target polynucleotide may comprise multiple disease-related genes and polynucleotides and signal transduction biochemical pathway-related genes and polynucleotides. Non-limiting examples of such target sequences or target polynucleotides include those listed in U.S. provisional patent applications 61/736,527 and 61/748,427 filed on Dec. 12, 2012 and Jan. 2, 2013, respectively, and international application PCT/US2013/074667 filed on Dec. 12, 2013, all of which are incorporated herein by reference.

In some cases, examples of target sequences or target polynucleotides include sequences related to signal transduction biochemical pathways, such as genes or polynucleotides related to signal transduction biochemical pathways. Examples of target polynucleotides include disease-related genes or polynucleotides. A "disease-associated" gene or polynucleotide refers to any gene or polynucleotide that produces a transcriptional or translational product at an abnormal level or in an abnormal form in cells derived from a disease-affected tissue compared to tissues or cells of a non-disease control. In cases where the altered expression is associated with the onset and/or progression of a disease, it may be a gene that is expressed at an abnormally high level; alternatively, it may be a gene that is expressed at an abnormally low level. A disease-associated gene also refers to a gene that has one or more mutations or genetic variations that are directly responsible for or in linkage disequilibrium with one or more genes responsible for the etiology of the disease. The transcribed or translated product may be known or unknown and may be at normal level or abnormal level.

As used herein, the term "wild type" has the meaning commonly understood by those skilled in the art, which refers to a typical form of an organism, strain, gene, or a characteristic that distinguishes it from a mutant or variant form when it exists in nature, which can be isolated from a source in nature and has not been intentionally and artificially modified.

As used herein, the terms "non-naturally occurring" or "engineered" are used interchangeably and indicate artificial participation. When these terms are used to describe a nucleic acid molecule or polypeptide, it means that the nucleic acid molecule or polypeptide is at least substantially free from at least another component with which it is associated in nature or found in nature.

As used herein, the term "orthologue" or "ortholog" has the meaning commonly understood by those skilled in the art. As a further guide, an "ortholog" of protein as described herein refers to a protein belonging to a different species, and the protein performs the same or similar function as a protein that is its ortholog.

As used herein, the term "identity" is used to refer to the matching of sequences between two polypeptides or between two nucleic acids. When a position in both compared sequences is occupied by the same base or amino acid monomer subunit (e.g., a position in each of the two DNA molecules is occupied by adenine, or a position in each of the two polypeptides is occupied by lysine), then the molecules are identical at that position. The "percentage identity" between two sequences is a function of the number of matching positions shared by the two sequences divided by the number of positions compared×100. For example, if 6 out of 10 positions of the two sequences match, then the two sequences have an identity of 60%. For example, the DNA sequences CTGACT and CAGGTT have an identity of 50% (3 out of a total of 6 positions match). Typically, the two sequences are compared when they are aligned to produce maximum identity. Such an alignment can be achieved by using, for example, the method of Needleman et al. *J Mol. Biol.* 48: 443 to 453 (1970), which can be conveniently performed by a computer program such as the Align program (DNAstar, Inc.). The algorithm of E. Meyers and W. Miller (Comput. Appl Biosci., 4: 11 to 17 (1988)), which has been incorporated into the ALIGN program (version 2.0), can also be used to determine the percentage identity between two amino acid sequences using a PAM120 weight residue table, a gap length penalty of 12, and a gap penalty of 4. In addition, the percentage identity between two amino acid sequences can be determined using the algorithm of Needleman and Wunsch (J MoI Biol. 48:444 to 453 (1970)), which has been incorporated into the GAP program of the GCG software package (available at www.gcg.com), using a Blossum 62 matrix or a PAM250 matrix as well as a gap weight of 16, 14, 12, 10, 8, 6 or 4 and a length weight of 1, 2, 3, 4, 5 or 6.

As used herein, the term "vector" refers to a nucleic acid delivery vehicle into which a polynucleotide can be inserted. When a vector is capable of expressing a protein encoded by the inserted polynucleotide, the vector is called an expression vector. The vector can be introduced into a host cell by transformation, transduction or transfection so that the genetic material elements it carries are expressed in the host cell. Vectors are well known to those skilled in the art, including but not limited to: plasmid; phagemid; cosmid; artificial chromosome, such as yeast artificial chromosome (YAC), bacterial artificial chromosome (BAC) or P1-derived artificial chromosome (PAC); bacteriophage such as k phage or M13 phage and animal virus, etc. Animal viruses that can be used as vectors include but are not limited to retrovirus (including lentivirus), adenovirus, adeno-associated virus, herpes virus (e.g., herpes simplex virus), poxvirus, baculovirus, papillomavirus, papovavirus (e.g., SV40). A vector may contain a variety of elements for controlling expression, including but not limited to promoter sequence, transcription start sequence, enhancer sequence, selection element and reporter gene. In addition, the vector may also comprise a replication origin.

As used herein, the term "host cell" refers to a cell that can be used to introduce a vector, including but not limited to prokaryotic cell such as *Escherichia coli* or *Bacillus subtilis*, fungal cell such as yeast cell or *Aspergillus*, insect cell such as S2 *Drosophila* cell or Sf9, or animal cell such as fibroblast, CHO cell, COS cell, NSO cell, HeLa cell, BHK cell, HEK 293 cell or human cell.

Those skilled in the art will understand that the design of expression vector may depend on factors such as the choice of host cell to be transformed, the desired expression level, etc. A vector can be introduced into a host cell to produce a transcript, protein, or peptide, including the protein, fusion protein, isolated nucleic acid molecule, etc. as described herein (e.g., CRISPR transcript, such as nucleic acid transcript, protein, or enzyme).

As used herein, the term "regulatory element" is intended to include a promoter, enhancer, internal ribosome entry site (IRES), and other expression control element (e.g., transcription termination signal, such as polyadenylation signal and poly-U sequence), which may be referred in details to Goeddel, GENE EXPRESSION TECHNOLOGY: METHODS IN ENZYMOLOGY 185, Academic Press, San Diego, California (1990). In some cases, regulatory elements include those sequences that direct the constitutive expression of a nucleotide sequence in many types of host cells and those sequences (e.g., tissue-specific regulatory sequences) that direct the nucleotide sequence to be expressed only in certain host cells. Tissue-specific promoters may primarily direct expression in the desired tissue of interest, such as muscle, neuron, bone, skin, blood, specific organ (e.g., liver, pancreas), or special cell type (e.g., lymphocyte). In some cases, regulatory elements may also direct expression in a timing-dependent manner (e.g., in a cell cycle-dependent or developmental stage-dependent manner), which may or may not be tissue or cell type-specific. In some cases, the term "regulatory element" encompasses enhancer elements, such as WPRE; CMV enhancer; R-U5' fragment (Mol. Cell. Biol., Vol. 8(1), pp. 466 to 472, 1988); SV40 enhancer; and intron sequence between exons 2 and 3 of rabbit β-globin (Proc. Natl. Acad. Sci. USA., Vol. 78(3), pp. 1527 to 31, 1981).

As used herein, the term "promoter" has the meaning well known to those skilled in the art, which refers to a non-coding nucleotide sequence located upstream of a gene that can initiate expression of a downstream gene. A constitutive promoter is a nucleotide sequence that, when operably linked to a polynucleotide encoding or defining a gene product, leads to the production of a gene product in a cell under most or all of the physiological conditions of the cell. An inducible promoter is a nucleotide sequence that, when operably linked to a polynucleotide encoding or defining a gene product, leads to the production of a gene product in a cell substantially only when an inducer corresponding to the promoter is present in the cell. A tissue-specific promoter is a nucleotide sequence that, when operably linked to a polynucleotide encoding or defining a gene product, leads to the production of a gene product in a cell substantially only when the cell is a cell of the tissue type corresponding to the promoter.

As used herein, the term "operably linked" is intended to mean that the nucleotide sequence of interest is linked to the one or more regulatory elements in a manner that allows the expression of the nucleotide sequence (e.g., in an in vitro transcription/translation system or in a host cell when the vector is introduced into the host cell).

As used herein, the term "complementarity" refers to the ability of a nucleic acid to form one or more hydrogen bonds with another nucleic acid sequence by means of traditional Watson-Crick or other non-traditional types. The percentage of complementarity indicates the percentage of residues in a nucleic acid molecule that can form hydrogen bonds (e.g., Watson-Crick base pairing) with a second nucleic acid sequence (e.g., for 5, 6, 7, 8, 9, 10 out of 10, the complementarity is 50%, 60%, 70%, 80%, 90%, and 100%, respectively). "Complete complementarity" means that all consecutive residues of a nucleic acid sequence form hydrogen bonds with the same number of residues in a second nucleic acid sequence. As used herein, "substantially complementary" refers to a degree of complementarity of at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50 or more nucleotides, or refers to two nucleic acids that hybridize under stringent conditions.

As used herein, "stringent conditions" for hybridization refer to conditions in which a nucleic acid having complementarity to a target sequence predominantly hybridizes to the target sequence and does not substantially hybridize to non-target sequences. Stringent conditions are typically sequence-dependent and vary depending on many factors. In general, the longer the sequence, the higher the temperature at which the sequence specifically hybridizes to its target sequence. Non-limiting examples of stringent conditions are described in Tijssen, Laboratory Techniques In Biochemistry And Molecular Biology-Hybridization With Nucleic Acid Probes, Part I, Chapter 2, "Overview of principles of hybridization and the strategy of nucleic acid probe assay", (1993), Elsevier, New York.

As used herein, the term "hybridization" refers to a reaction in which one or more polynucleotides react to form a complex that is stabilized by hydrogen bonding of the bases between the nucleotide residues. Hydrogen bonding may occur by means of Watson-Crick base pairing, Hoogstein binding, or in any other sequence-specific manner. The complex may contain two strands forming a duplex, three or more strands forming a multi-stranded complex, a single self-hybridizing strand, or any combination thereof. A hybridization reaction may constitute a step in a broader process (e.g., initiation of PCR, or cleavage of polynucleotide by enzyme). A sequence capable of hybridizing to a given sequence is called the "complement" of the given sequence.

As used herein, the term "expression" refers to a process by which a polynucleotide is transcribed from a DNA template (e.g., transcribed into mRNA or other RNA transcript) and/or a process by which the transcribed mRNA is subsequently translated into a peptide, polypeptide or protein. The transcript and encoded polypeptide can be collectively referred to as "gene products". If the polynucleotide is derived from a genomic DNA, the expression may comprise splicing of mRNA in a eukaryotic cell.

As used herein, the term "linker" refers to a linear polypeptide formed by multiple amino acid residues connected by peptide bonds. The linker of the present invention can be an artificially synthesized amino acid sequence, or a naturally occurring polypeptide sequence, such as a polypeptide having a hinge region function. Such linker polypeptides are well known in the art (see, for example, Holliger, P. et al. (1993) Proc. Natl. Acad. Sci. USA 90: 6444 to 6448; Poljak, R. J. et al. (1994) Structure 2: 1121-1123).

As used herein, the term "treatment" refers to treating or curing a condition, delaying the onset of symptoms of a condition, and/or delaying the development of a condition.

As used herein, the term "subject" includes, but is not limited to, various animals, such as mammals, such as bovines, equines, ovines, porcines, canines, felines, lagomorphs, rodents (e.g., mice or rats), non-human primates (e.g., macaques or cynomolgus monkeys), or humans. In certain embodiments, the subject (e.g., a human) suffers from a condition (e.g., a condition caused by a disease-related gene defect).

Beneficial Effects of the Invention

Compared with the prior art, the Cas protein and system of the present invention have significant advantages. For example, the Cas effector protein of the present invention is smaller in molecular size than Cas9, C2c1, CasY, and Cpf1 proteins, and therefore has better transfection efficiency than Cas9, C2c1, CasY, and Cpf1 proteins. For example, the PAM domain of the Cas effector protein of the present invention is of the 5' RYR structure (R is A or G, Y is T or C), and there are 8 recognizable PAM combinations, namely ATG, ACG, ATA, ACA, GTG, GTA, GCG and GCA, which have wider recognition sites than the currently reported NGG PAM recognized by SpCas9 and TTN PAM recognized by LbCas12a.

The embodiments of the present invention will be described in detail below in conjunction with the accompanying drawings and examples, but those skilled in the art will understand that the following drawings and examples are only used to illustrate the present invention, rather than to limit the scope of the present invention. According to the following detailed description of the accompanying drawings and preferred embodiments, the various objects and advantages of the present invention will become apparent to those skilled in the art.

SEQUENCE INFORMATION

Figure 1A:
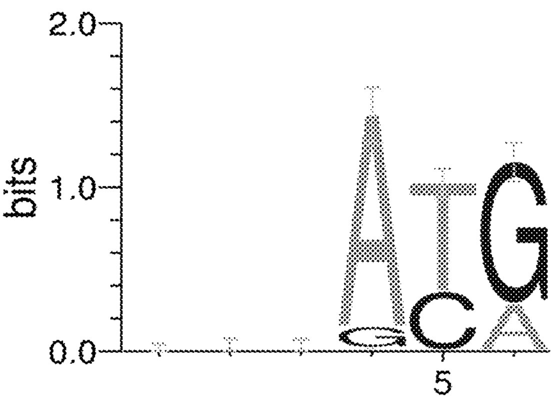
FIGS. 1A and B show the PAM structure analysis and verification results of Casδ-1 in Example 3.
Figure 1A:
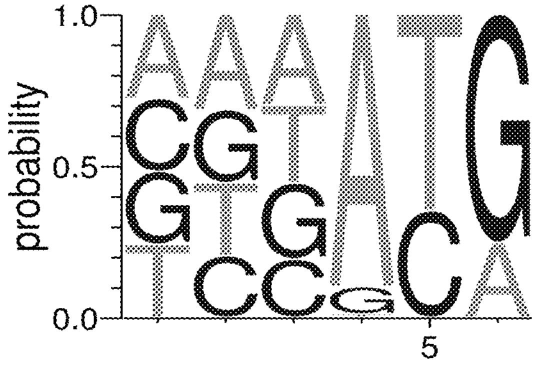

The information of the partial sequences involved in the present invention is provided in Table 1 below.

TABLE 1

Description of sequences

| SEQ ID NO: | Description |
|---|---|
| 1 | Amino acid sequence of Casδ-1<br>MSKDGDKMKHSKQEVSEDKGVKKDPSVFRCQNLAILEMREEVADYYADLQADYR<br>HYLPLMILWGQNGFMEPDETGLNFSAVLPSTAKTRCENRYGAQIAADLKLIADDLP<br>SSLYAIFTNDYQPLTGVKKVGDRWKFVTSLNTVSDEEFAKKVKPLLRDYKGVTEEQ<br>WRRFREER VAGKTADQVWDDLDSILRNPTLAALKKIHDKHMFRVKRPESKLYCDA<br>LAHmLSSSYDSWKKINEARQLELQAMRDEQQGLLANKTTNSLYNLVCEFADELESQ<br>NYGLTRRIFFIARKEWEDEKSHYLPVIKLLVTEKYLPLLQADNKTVSPAVKAWDICS<br>TLKQRSPYIRFVPPTKDYPIPFGQTGRGHKFTLKEEAGKVCFLVPGLTKDEMPLSGSH<br>YFSSLRIDKVGTDFKISFRHKTKIRSKKSARVTVKQPRINGTVTEVGILRRNGKFFLR<br>VAYKIAYPQHNIDLKSYFASAAPSTQKLELLPAQMRVAGVDLNISDPIVVSKADIFK<br>GEDGGPLSVLDYGSGKVVGEPVIICKDTSRAGKISSLATKCRTLRDVIRNFRHSLHQ<br>GTPLPSKSLEFLQEVPVAQEDLKSPSPRYLIQTWIKYIRTEMKRLHYKVWLDGYCHT<br>SEAMRmLDLVDQVAFLMKSYENIHVKPGHKIPKKTTASLKIRETSRTRFRLHVSRLV<br>GARVVRACEDCQMIFLEDLSTGFSEGSNNSLARLFSAGQLKNSIVMAAEKVGKAVV<br>FVCKDGTSIKDPVFGLHGLRPSKKTPGIPPDKKRLYVRRDGKIGYINADQAASLNVL<br>LVGLSHSVAKYKFFVKDGKLQDDEEVAAQQGKKPRKIGVRLERLLKMNFDTPARL<br>FFSLEKDQVVPCYEATETPYTGWVYVYHDRLLTTRQRDQQVNQLAQEVKDLLRDG<br>VKIPKWDVIPDCDNSCLGFSPCLVLDDETAAVSVV |
| 2 | Amino acid sequence of Casδ-2<br>MELKTTFCQSLKIKILPESHKLYYDELQADLKKMRIFFATHSGLNYSYKEDENDSEW<br>KIASSKKSTLSPEAQRLIDIIAKGGIGAEHAYGIFYKDKKVSDKIRRDNSNCIFAmLLP<br>NLVNFEEEYKKRKSKLQLTKEEWEEYHKRCLAGESVEVLWSEEIAPKIGPNEAARL<br>ASLAYHQFPDSRHPADITHCRALMSMVADSFCSWVECHKLHREETEKLKTKLQEKI<br>ESCKEAYNLLLAYSEDLYSRNYGLSARVLKALIDNKSRCCFDIAFQIAEKYPALMKI<br>DEKTLFKAYNALKLHWKIKRRKPFISLPKIERDYQVPFGLTGSRGKKFDVYVENKNI<br>VVEIDGQKVETFSSHYFSDMQISKIYGEKKNLKGFKLKFRHKLKDKKKEVYGEWIE<br>AELKEIKIKKDMETGDFYLYLPYTTTHNEKNLLLEKFFSYADPLKETIFKNGKTELPN<br>EFLGFGFDLNLSDPIAMAVAEFVRDSSDGEIGALDYGHGKLLDASVLVCNSSLSKRI<br>NDLVGDNRKLIQAIRSYKNSLVTKEMDEESGEWLKKALGNAKYGNHRHQLQLVMS<br>KLNKKSKKYWQECRKNGHNDLSENIALLKLLDVQFSLHKSYNNIHIFDYKKQIHSH<br>KTDSKRENFREFVTKQFAATIVKHCKEVMAKYGREYAVVFLEDLEMYFDADADNN<br>SLIRLFAPGQLKKYIASALAKSKIGYVFIPPAGTSKTDPLTSKIGFRATGKYYKQLGY<br>LLNKSDLYVERNGVIGKINSDVAAAINILLKGVNHSIVPYRFLNKHAGSEQKRLKRF<br>EGEIGCDLKKMPKTRLYYLDGKIITEEEKNSLEEALLAEIKHFLLSKANIPEFDAIPGS<br>NGTCKAFSVPRCLK |
| 3 | Amino acid sequence of Casδ-1D31<br>NLAILEMREEVADYYADLQADYRHYLPLMILWGQNGFMEPDETGLNFSAVLPSTA<br>KTRCENRYGAQIAADLKLIADDLPSSLYAIFTNDYQPLTGVKKVGDRWKFVTSLNT<br>VSDEEFAKKVKPLLRDYKGVTEEQWRRFREERVAGKTADQVWDDLDSILRNPTLA<br>ALKKIHDKHMFRVKRPESKLYCDALAHmLSSSYDSWKKINEARQLELQAMRDEQQ<br>GLLANKTTNSLYNLVCEFADELESQNYGLTRRIFFIARKEWEDEKSHYLPVIKLLVT<br>EKYLPLLQADNKTVSPAVKAWDICSTLKQRSPYIRFVPPTKDYPIPFGQTGRGHKFT<br>LKEEAGKVCFLVPGLTKDEMPLSGSHYFSSLRIDKVGTDFKISFRHKTKIRSKKSARV<br>TVKQPRINGTVTEVGILRRNGKFFLRVAYKIAYPQHNIDLKSYFASAAPSTQKLELLP<br>AQMRVAGVDLNISDPIVVSKADIFKGEDGGPLSVLDYGSGKVVGEPVIICKDTSRAG<br>KISSLATKCRTLRDVIRNFRHSLHQGTPLPSKSLEFLQEVPVAQEDLKSPSPRYLIQT<br>WIKYIRTEMKRLHYKVWLDGYCHTSEAMRmLDLVDQVAFLMKSYENIHVKPGHKI |

TABLE 1-continued

| SEQ ID NO: | Description of sequences<br>Description |
|---|---|
| | PKKTTASLKIRETSRTRFRLHVSRLVGARVVRACEDCQMIFLEDLSTGFSEGSNNSLA<br>RLFSAGQLKNSIVMAAEKVGKAVVFVCKDGTSIKDPVFGLHGLRPSKKTPGIPPDKK<br>RLYVRRDGKIGYINADQAASLNVLLVGLSHSVAKYKFFVKDGKLQDDEEVAAQQG<br>KKPRKIGVRLERLLKMNFDTPARLFFSLEKDQVVPCYEATETPYTGWVYVYHDRLL<br>TTRQRDQQVNQLAQEVKDLLRDGVKIPKWDVIPDCDNSCLGFSPCLVLDDETAAVS<br>VV |
| 4 | Encoding nucleotide sequence of Casδ-1<br>ATGTCCAAAGACGGTGACAAGATGAAGCACAGCAAACAAGAAGTCTCTGAGGA<br>CAAAGGGGTCAAGAAAGACCCGTCTGTCTTCCGCTGTCAGAACCTCGCGATTCT<br>GGAGATGCGTGAAGAAGTCGCTGATTACTACGCCGACCTTCAGGCCGACTACCG<br>TCACTACTTGCCCCTGATGATCCTCTGGGGCCAGAACGGGTTCATGGAGCCAGA<br>CGAAACTGGTCTGAACTTCAGTGCCGTCCTGCCATCGACCGCAAAAACACGGTG<br>CGAGAACCGCTACGGTGCGCAGATTGCGGCTGATCTCAAGTTGATCGCCGACGA<br>TCTCCCGAGCAGTCTCTATGCCATCTTCACCAACGACTACCAGCCCCTCACCGGC<br>GTGAAGAAGGTCGGCGACAGATGGAAGTTCGTCACGTCCCTCAACACTGTCAGC<br>GACGAAGAGTTCGCCAAGAAGGTGAAGCCGCTCCTGCGTGACTACAAAGGCGTT<br>ACCGAAGAGCAGTGGCGTCGATTTCGTGAAGAGCGTGTCGCCGGCAAGACAGCC<br>GATCAGGTCTGGGACGACCTTGACAGCATTCTGCGAAACCCGACGCTCGCGGCC<br>CTGAAGAAGATCCACGACAAGCACATGTTCCGGGTCAAGCGACCCGAGAGCAA<br>ACTCTACTGTGACGCCCTGGCTCACATGCTGAGTTCCAGCTACGACAGTTGGAA<br>GAAAATCAACGAGGCCCGCCAACTCGAACTCCAAGCCATGCGTGACGAGCAGC<br>AGGGCTTGCTCGCCAACAAGACCACGAACAGTCTGTACAATCTGGTGTGCGAGT<br>TCGCCGACGAACTGGAGTCGCAGAACTACGGTCTGACTCGGCGGATCTTCTTCA<br>TCGCCCGCAAAGAGTGGGAGGACGAAAAGTCCCATTACCTCCCGGTCATCAAGC<br>TCCTCGTCACGGAGAAGTATCTGCCCCTGCTCCAGGCGGATAACAAGACTGTCA<br>GCCCCGCCGTCAAGGCGTGGGACATCTGCTCTACTCTGAAGCAGAGGTCGCCGT<br>ACATCCGCTTCGTGCCTCCGACCAAGGACTATCCGATCCCCTTCGGCCAGACGG<br>GTCGCGGACACAAGTTCACCTTGAAAGAGGAAGCCGGAAAGGTCTGTTTCCTCG<br>TACCCGGCCTGACCAAGGACGAGATGCCTCTGTCCGGCTCTCACTACTTCTCAAG<br>CCTCCGTATCGACAAGGTCGGCACAGACTTCAAGATCTCGTTCCGTCACAAGAC<br>CAAGATTCGCAGCAAAAAGTCTGCGCGAGTCACCGTCAAGCAGCCCAGGATCAA<br>CGGCACCGTCACTGAGGTCGGCATCCTACGCAGGAACGGCAAGTTCTTCCTGCG<br>TGTCGCTTACAAGATCGCCTACCCACAGCACAACATCGACCTGAAGAGCTACTT<br>CGCCTCGGCAGCCCCCTCCACGCAAAAGCTGGAGCTTCTGCCGGCTCAAATGAG<br>AGTCGCGGGCGTCGATCTGAACATCAGCGACCCGATTGTCGTCTCCAAGGCCGA<br>CATCTTCAAGGGCGAAGACGGCGGGCCGCTGTCTGTGCTGGACTACGGCTCTGG<br>CAAGGTGGTAGGTGAGCCTGTGATCATCTGCAAGGACACCAGCAGGGCCGGGA<br>AGATCAGTTCCCTCGCCACGAAATGCCGGACGCTACGCGACGTGATCCGCAACT<br>TTCGTCATTCACTGCATCAGGGTACGCCCTTGCCCAGCAAGAGTCTTGAATTTCT<br>CCAAGAAGTTCCCGTGGCGCAGGAGGACTTGAAGTCGCCCAGCCCTCGCTATCT<br>GATCCAGACGTGGATCAAGTACATCAGGACCGAGATGAAGCGACTTCACTACAA<br>GGTCTGGCTCGACGGGTACTGCCACACTAGCGAAGCCATGCGGATGCTCGATCT<br>GGTCGATCAGGTCGCGTTCCTAATGAAGTCGTATGAGAACATCCACGTCAAACC<br>GGGTCACAAGATCCCGAAGAAGACCACTGCGTCCCTGAAGATTCGCGAGACGAG<br>CCGAACGCGGTTCAGGCTGCATGTCTCCCGACTTGTCGGTGCGCGAGTGGTTCGT<br>GCGTGCGAGGACTGCCAGATGATCTTCTTGGAAGATCTCTCGACAGGTTTCTCCG<br>AAGGCAGCAATAACTCGTTGGCCCGGCTGTTTTCGGCTGGCCAACTGAAGAACT<br>CCATCGTCATGGCGGCAGAGAAGGTCGGCAAAGCCGTAGTCTTCGTGTGCAAGG<br>ACGGTACGTCTATCAAAGATCCTGTTTTCGGTCTGCACGGCCTGCGGCCTTCCAA<br>GAAGACCCCAGGCATTCCGCCGGACAAGAAGCGTCTCTACGTCCGTCGCGACGG<br>CAAAATCGGCTACATCAACGCCGATCAGGCGGCTTCGCTGAATGTGCTGCTGGT<br>GGGGCTGTCGCACTCCGTCGCCAAGTACAAGTTCTTTGTCAAGGACGGGAAGCT<br>ACAAGACGACGAGGAGGTGGCTGCCCAGCAAGGCAAGAAGCCGCGTAAGATCG<br>GTGTTCGTCTGGAAAGACTCCTCAAGATGAACTTCGACACCCCTGCCAGACTTTT<br>CTTCTCGCTGGAGAAAGATCAGGTGGTGCCGTGCTACGAGGCCACGGAAACGCC<br>TTACACCGGCTGGGTCTACGTCTACCACGACCGACTGCTGACCACCCGGCAACG<br>TGATCAGCAAGTCAATCAACTCGCACAGGAAGTCAAGGATCTCCTGCGGGATGG<br>TGTCAAAATTCCTAAATGGGACGTAATCCCAGACTGCGACAACAGTTGCCTCGG<br>CTTCTCTCCGTGTCTGGTGCTTGACGACGAAACCGCCGCTGTTTCTGTGGTTTAG |
| 5 | Encoding nucleotide sequence of Casδ-2<br>ATGGAATTGAAGACAACTTTTTGTCAGTCACTAAAAATTAAGATCCTCCCCGAA<br>AGCCATAAGTTGTATTACGATGAGCTGCAAGCCGACCTAAAGAAGATGAGAATC<br>TTCTTCGCAACGCACTCTGGGCTCAACTACAGCTACAAGGAAGATGAAAACGAT<br>TCGGAATGGAAGATAGCGTCGTCAAAAAAGAGCACACTCTCACCTGAAGCCCAA<br>AGGCTTATTGACATCATCGCCAAAGGCGGTATAGGAGCAGAGCACGCCTACGGA<br>ATATTTTACAAGGACAAAAAGGTGTCGGACAAGATCCGGCGAGATAATTCAAAC<br>TGCATCTTCGCCATGCTATTACCTAACCTCGTCAATTTCGAGGAAGAATACAAAA<br>AGAGGAAAAGTAAGCTCCAGCTCACCAAGGAAGAGTGGGAGGAGTACCATAAA<br>CGATGTCTTGCAGGCGAGAGCGTGGAAGTCCTGTGGTCCGAGGAGATTGCTCCA<br>AAAATTGGGCCTAACGAAGCGGCGAGACTGGCATCACTCGCGTATCACCAGTTC<br>CCAGATTCTCGTCATCCGGCGGACATTACCCACTGCAGGGCGCTCATGTCTATGG<br>TAGCAGACTCTTTTTGTTCCTGGGTCGAGTGCCACAAGCTGCACCGTGAGGAAA |

TABLE 1-continued

| Description of sequences | |
|---|---|
| SEQ ID NO: | Description |
| | CAGAGAAACTCAAGACGAAATTACAGGAGAAGATAGAGAGCTGCAAGGAGGCA<br>TACAATCTGCTACTCGCTTATTCCGAAGACCTGTACAGTAGGAATTATGGTCTGA<br>GTGCCAGGGTTTTGAAGGCACTTATTGACAACAAATCCCGGTGCTGCTTCGACAT<br>AGCCTTTCAGATCGCGGAGAAATATCCTGCACTGATGAAGATTGATGAAAAGAC<br>CCTGTTCAAGGCCTACAACGCCCTAAAGCTCCACTGGAAAATAAAACGACGCAA<br>GCCGTTCATCTCGCTGCCCAAGATCGAGAGGGACTACCAGGTGCCCTTTGGACT<br>CACAGGAAGCAGAGGCAAGAAGTTCGACGTCTATGTGGAAAACAAGAATATTG<br>TGGTCGAGATCGACGGCCAGAAAGTCGAAACCTTCAGCTCTCACTATTTCTCTGA<br>TATGCAGATCTCCAAGATTTACGGTGAAAAGAAAAATTTGAAGGGATTCAAGTT<br>GAAATTCCGCCACAAGCTGAAGGACAAGAAGAAGGAGGTTTATGGAGAGTGGA<br>TTGAGGCGGAGCTGAAGGAAATCAAGATTAAGAAAGACATGGAGACAGGCGAC<br>TTCTACCTGTATCTCCCATACACTACAACGCATAATGAGAAAAACTTATTGCTCG<br>AGAAGTTCTTTTCCTACGCCGATCCACTTAAGGAGACTATTTTTAAGAACGGAAA<br>GACGGAGCTTCCAAATGAATTTCTAGGCTTCGGCTTCGATTTGAACCTTTCCGAC<br>CCGATTGCGATGGCGGTTGCCGAGTTTGTTCGGGACTCATCAGATGGTGAGATT<br>GGCGCCCTCGACTATGGTCACGGTAAGCTCCTCGACGCTAGTGTTTTGGTCTGCA<br>ACTCATCACTATCAAAGCGCATCAATGACCTGGTTGGAGACAATAGAAAGCTGA<br>TCCAAGCTATTAGATCGTACAAGAACTCGCTAGTAACTAAGGAAATGGACGAGG<br>AGAGTGGCGAGTGGCTTAAAAAAGCTCTAGGCAATGCAAAGTACGGCAACCAT<br>AGGCATCAGCTTCAACTGGTCATGTCTAAGCTGAACAAAAAAAGCAAAAAGTAC<br>TGGCAGGAATGTCGCAAGAACGGCCACAACGATCTTTCCGAAAATATTGCACTA<br>TTAAAGTTGTTGGACGTGCAGTTCTCTTTGCATAAAAGCTATAACAACATACACA<br>TCTTTGATTACAAAAAACAAATTCACAGCCATAAGACTGACTCCAAAAGGGAGA<br>ATTTCCGTGAATTTGTGACGAAGCAATTTGCGGCTACCATAGTAAAGCATTGCA<br>AGGAGGTGATGGCTAAATATGGCAGAGAGTACGCCGTTGTCTTTTTGGAGGACC<br>TGGAGATGTACTTTGATGCTGATGCTGATAACAATTCTCTGATCCGGCTTTTTGC<br>ACCCGGCCAATTGAAGAAGTACATCGCCTCCGCTCTGGCTAAGAGCAAGATAGG<br>TTATGTGTTCATCCCTCCTGCTGGGACAAGTAAGACCGACCCGTTAACTTCGAAA<br>ATTGGATTCAGGGCTACCGGAAAATACTACAAGCAGCTGGGCTATCTGCTTAAT<br>AAGTCCGACCTCTACGTGGAGCGCAACGGGGTTATCGGGAAGATCAACAGTGAT<br>GTAGCTGCGGCGATAAATATTCTCTTAAAGGGCGTGAACCACTCAATCGTGCCG<br>TACCGCTTCCTGAATAAACATGCTGGGTCTGAACAGAAGCGCCTCAAACGTTTT<br>GAAGGGGAGATCGGTTGTGATCTGAAAAAGATGCCAAAGACACGCCTCTACTAT<br>CTTGACGGAAAAATCATCACTGAAGAGGAGAAGAACAGCCTGGAGGAAGCGCT<br>ACTCGCTGAGATCAAGCACTTCCTTCTGTCGAAGGCCAACATTCCGGAGTTTGAT<br>GCAATACCGGGGAGCAATGGCACCTGCAAAGCCTTCTCCGTTCCACGCTGCCTT<br>AAGTGA |
| 6 | Encoding nucleotide sequence of Casδ-1D31<br>AACCTCGCGATTCTGGAGATGCGTGAAGAAGTCGCTGATTACTACGCCGACCTT<br>CAGGCCGACTACCGTCACTACTTGCCCCTGATGATCCTCTGGGGCCAGAACGGG<br>TTCATGGAGCCAGACGAAACTGGTCTGAACTTCAGTGCCGTCCTGCCATCGACC<br>GCAAAAACACGGTGCGAGAACCGCTACGGTGCGCAGATTGCGGCTGATCTCAAG<br>TTGATCGCCGACGATCTCCCGAGCAGTCTCTATGCCATCTTCACCAACGACTACC<br>AGCCCCTCACCGGCGTGAAGAAGGTCGGCGACAGATGGAAGTTCGTCACGTCCC<br>TCAACACTGTCAGCGACGAAGAGTTCGCCAAGAAGGTGAAGCCGCTCCTGCGTG<br>ACTACAAAGGCGTTACCGAAGAGCAGTGGCGTCGATTTCGTGAAGAGCGTGTCG<br>CCGGCAAGACAGCCGATCAGGTCTGGGACGACCTTGACAGCATTCTGCGAAACC<br>CGACGCTCGCGGCCCTGAAGAAGATCCACGACAAGCACATGTTCCGGGTCAAGC<br>GACCCGAGAGCAAACTCTACTGTGACGCCCTGGCTCACATGCTGAGTTCCAGCT<br>ACGACAGTTGGAAGAAAATCAACGAGGCCCGCCAACTCGAACTCCAAGCCATGC<br>GTGACGAGCAGCAGGGCTTGCTCGCCAACAAGACCACGAACAGTCTGTACAATC<br>TGGTGTGCGAGTTCGCCGACGAACTGGAGTCGCAGAACTACGGTCTGACTCGGC<br>GGATCTTCTTCATCGCCCGCAAAGAGTGGGAGGACGAAAAGTCCCATTACCTCC<br>CGGTCATCAAGCTCCTCGTCACGGAGAAGTATCTGCCCCTGCTCCAGGCGGATA<br>ACAAGACTGTCAGCCCCGCCGTCAAGGCGTGGGACATCTGCTCTACTCTGAAGC<br>AGAGGTCGCCGTACATCCGCTTCGTGCCTCCGACCAAGGACTATCCGATCCCCTT<br>CGGCCAGACGGGTCGCGGACACAAGTTCACCTTGAAAGAGGAAGCCGGAAAGG<br>TCTGTTTCCTCGTACCCGGCCTGACCAAGGACGAGATGCCTCTGTCCGGCTCTCA<br>CTACTTCTCAAGCCTCCGTATCGACAAGGTCGGCACAGACTTCAAGATCTCGTTC<br>CGTCACAAGACCAAGATTCGCAGCAAAAAGTCTGCGCGAGTCACCGTCAAGCAG<br>CCCAGGATCAACGGCACCGTCACTGAGGTCGGCATCCTACGCAGGAACGGCAAG<br>TTCTTCCTGCGTGTCGCTTACAAGATCGCCTACCCACAGCACAACATCGACCTGA<br>AGAGCTACTTCGCCTCGGCAGCCCCCTCCACGCAAAAGCTGGAGCTTCTGCCGG<br>CTCAAATGAGAGTCGCGGGCGTCGATCTGAACATCAGCGACCCGATTGTCGTCT<br>CCAAGGCCGACATCTTCAAGGGCGAAGACGGCGGGCCGCTGTCTGTGCTGGACT<br>ACGGCTCTGGCAAGGTGGTAGGTGAGCCTGTGATCATCTGCAAGGACACCAGCA<br>GGGCCGGGAAGATCAGTTCCCTCGCCACGAAATGCCGGACGCTACGCGACGTGA<br>TCCGCAACTTTCGTCATTCACTGCATCAGGGTACGCCCTTGCCCAGCAAGAGTCT<br>TGAATTTCTCCAAGAAGTTCCCGTGGCGCAGGAGGACTTGAAGTCGCCCAGCCC<br>TCGCTATCTGATCCAGACGTGGATCAAGTACATCAGGACCGAGATGAAGCGACT<br>TCACTACAAGGTCTGGCTCGACGGGTACTGCCACACTAGCGAAGCCATGCGGAT<br>GCTCGATCTGGTCGATCAGGTCGCGTTCCTAATGAAGTCGTATGAGAACATCCA<br>CGTCAAACCGGGTCACAAGATCCCGAAGAAGACCACTGCGTCCCTGAAGATTCG |

TABLE 1-continued

| Description of sequences | |
|---|---|
| SEQ ID NO: | Description |
| | CGAGACGAGCCGAACGCGGTTCAGGCTGCATGTCTCCCGACTTGTCGGTGCGCG<br>AGTGGTTCGTGCGTGCGAGGACTGCCAGATGATCTTCTTGGAAGATCTCTCGAC<br>AGGTTTCTCCGAAGGCAGCAATAACTCGTTGGCCCGGCTGTTTTCGGCTGGCCAA<br>CTGAAGAACTCCATCGTCATGGCGGCAGAGAAGGTCGGCAAAGCCGTAGTCTTC<br>GTGTGCAAGGACGGTACGTCTATCAAAGATCCTGTTTTCGGTCTGCACGGCCTGC<br>GGCCTTCCAAGAAGACCCCAGGCATTCCGCCGGACAAGAAGCGTCTCTACGTCC<br>GTCGCGACGGCAAAATCGGCTACATCAACGCCGATCAGGCGGCTTCGCTGAATG<br>TGCTGCTGGTGGGGCTGTCGCACTCCGTCGCCAAGTACAAGTTCTTTGTCAAGGA<br>CGGGAAGCTACAAGACGACGAGGAGGTGGCTGCCCAGCAAGGCAAGAAGCCGC<br>GTAAGATCGGTGTTCGTCTGGAAAGACTCCTCAAGATGAACTTCGACACCCCTG<br>CCAGACTTTTCTTCTCGCTGGAGAAAGATCAGGTGGTGCCGTGCTACGAGGCCA<br>CGGAAACGCCTTACACCGGCTGGGTCTACGTCTACCACGACCGACTGCTGACCA<br>CCCGGCAACGTGATCAGCAAGTCAATCAACTCGCACAGGAAGTCAAGGATCTCC<br>TGCGGGATGGTGTCAAAATTCCTAAATGGGACGTAATCCCAGACTGCGACAACA<br>GTTGCCTCGGCTTCTCTCCGTGTCTGGTGCTTGACGACGAAACCGCCGCTGTTTC<br>TGTGGTTTAG |
| 7 | Direct repeat sequence of Casδ-1<br>GUGCUGACGACCAGCACUAGAUGGUCGUUCAGGCAC |
| 8 | Direct repeat sequence of Casδ-2<br>GUGCUGAACAGGGUCGCUAGGCGUUGUUCAAGGCAC |
| 9 | Direct repeat sequence of Casδ-1R34<br>GCUGACGACCAGCACUAGAUGGUCGUUCAGGCAC |
| 10 | Direct repeat sequence of Casδ-1R32<br>UGACGACCAGCACUAGAUGGUCGUUCAGGCAC |
| 11 | Direct repeat sequence of Casδ-1R30<br>ACGACCAGCACUAGAUGGUCGUUCAGGCAC |
| 12 | Direct repeat sequence of Casδ-1R28<br>GACCAGCACUAGAUGGUCGUUCAGGCAC |
| 13 | Direct repeat sequence of Casδ-1R26<br>CCAGCACUAGAUGGUCGUUCAGGCAC |
| 14 | Direct repeat sequence of Casδ-1R24<br>AGCACUAGAUGGUCGUUCAGGCAC |
| 15 | Direct repeat sequence of Casδ-1R22<br>CACUAGAUGGUCGUUCAGGCAC |
| 16 | Direct repeat sequence of Casδ-1R20<br>CUAGAUGGUCGUUCAGGCAC |
| 17 | Encoding nucleic acid sequence of direct repeat sequence of Casδ-1<br>GTGCTGACGACCAGCACTAGATGGTCGTTCAGGCAC |
| 18 | Encoding nucleic acid sequence of direct repeat sequence of Casδ-2<br>GTGCTGAACAGGGTCGCTAGGCGTTGTTCAAGGCACG |
| 19 | Encoding nucleic acid sequence of direct repeat sequence of Casδ-1R34<br>GCTGACGACCAGCACTAGATGGTCGTTCAGGCAC |
| 20 | Encoding nucleic acid sequence of direct repeat sequence of Casδ-1R32<br>TGACGACCAGCACTAGATGGTCGTTCAGGCAC |
| 21 | Encoding nucleic acid sequence of direct repeat sequence of Casδ-1R30<br>ACGACCAGCACTAGATGGTCGTTCAGGCAC |
| 22 | Encoding nucleic acid sequence of direct repeat sequence of Casδ-1R28<br>GACCAGCACTAGATGGTCGTTCAGGCAC |
| 23 | Encoding nucleic acid sequence of direct repeat sequence of Casδ-1R26<br>CCAGCACTAGATGGTCGTTCAGGCAC |
| 24 | Encoding nucleic acid sequence of direct repeat sequence of Casδ-1R24<br>AGCACTAGATGGTCGTTCAGGCAC |
| 25 | Encoding nucleic acid sequence of direct repeat sequence of Casδ-1R22<br>CACTAGATGGTCGTTCAGGCAC |

TABLE 1-continued

| SEQ ID NO: | Description |
|---|---|
| 26 | Encoding nucleic acid sequence of direct repeat sequence of Casδ-1R20<br>CTAGATGGTCGTTCAGGCAC |
| 27 | NLS sequence<br>SRADPKKKRKV |
| 28 | Amino acid sequence of Casδ-1-NLS fusion protein<br>MGPKKKRKVMDYKDHDGDYKDHDIDYKDDDDKMSKDGDKMKHSKQEVSEDKG<br>VKKDPSVFRCONLAILEMREEVADYYADLQADYRHYLPLMILWGQNGFMEPDETG<br>LNFSAVLPSTAKTRCENRYGAQIAADLKLIADDLPSSLYAIFTNDYQPLTGVKKVGD<br>RWKFVTSLNTVSDEEFAKKVKPLLRDYKGVTEEQWRRFREERVAGKTADQVWDD<br>LDSILRNPTLAALKKIHDKHMFRVKRPESKLYCDALAHmLSSSYDSWKKINEARQL<br>ELQAMRDEQQGLLANKTTNSLYNLVCEFADELESQNYGLTRRIFFIARKEWEDEKS<br>HYLPVIKLLVTEKYLPLLQADNKTVSPAVKAWDICSTLKQRSPYIRFVPPTKDYPIPF<br>GQTGRGHKFTLKEEAGKVCFLVPGLTKDEMPLSGSHYFSSLRIDKVGTDFKISFRHK<br>TKIRSKKSARVTVKQPRINGTVTEVGILRRNGKFFLRVAYKIAYPQHNIDLKSYFASA<br>APSTQKLELLPAQMRVAGVDLNISDPIVVSKADIFKGEDGGPLSVLDYGSGKVVGEP<br>VIICKDTSRAGKISSLATKCRTLRDVIRNFRHSLHQGTPLPSKSLEFLQEVPVAQEDL<br>KSPSPRYLIQTWIKYIRTEMKRLHYKVWLDGYCHTSEAMRmLDLVDQVAFLMKSY<br>ENIHVKPGHKIPKKTTASLKIRETSRTRFRLHVSRLVGARVVRACEDCQMIFLEDLST<br>GFSEGSNNSLARLFSAGQLKNSIVMAAEKVGKAVVFVCKDGTSIKDPVFGLHGLRP<br>SKKTPGIPPDKKRLYVRRDGKIGYINADQAASLNVLLVGLSHSVAKYKFFVKDGKL<br>QDDEEVAAQQGKKPRKIGVRLERLLKMNFDTPARLFFSLEKDQVVPCYEATETPYT<br>GWVYVYHDRLLTTRQRDQQVNQLAQEVKDLLRDGVKIPKWDVIPDCDNSCLGFSP<br>CLVLDDETAAVSVVSRADPKKKRKV |
| 29 | Amino acid sequence of Casδ-2-NLS fusion protein<br>MGPKKKRKVMDYKDHDGDYKDHDIDYKDDDDKMELKTTFCQSLKIKILPESHKLY<br>YDELQADLKKMRIFFATHSGLNYSYKEDENDSEWKIASSKKSTLSPEAQRLIDIIAKG<br>GIGAEHAYGIFYKDKKVSDKIRRDNSNCIFAmLLPNLVNFEEEYKKRKSKLQLTKEE<br>WEEYHKRCLAGESVEVLWSEEIAPKIGPNEAARLASLAYHQFPDSRHPADITHCRAL<br>MSMVADSFCSWVECHKLHREETEKLKTKLQEKIESCKEAYNLLLAYSEDLYSRNYG<br>LSARVLKALIDNKSRCCFDIAFQIAEKYPALMKIDEKTLFKAYNALKLHWKIKRRKP<br>FISLPKIERDYQVPFGLTGSRGKKFDVYVENKNIVVEIDGQKVETFSSHYFSDMQISK<br>IYGEKKNLKGFKLKFRHKLKDKKKEVYGEWIEAELKEIKIKKDMETGDFYLYLPYT<br>TTHNEKNLLLEKFFSYADPLKETIFKNGKTELPNEFLGFGFDLNLSDPIAMAVAEFVR<br>DSSDGEIGALDYGHGKLLDASVLVCNSSLSKRINDLVGDNRKLIQAIRSYKNSLVTK<br>EMDEESGEWLKKALGNAKYGNHRHQLQLVMSKLNKKSKKYWQECRKNGHNDLS<br>ENIALLKLLDVQFSLHKSYNNIHIFDYKKQIHSHKTDSKRENFREFVTKQFAATIVKH<br>CKEVMAKYGREYAVVFLEDLEMYFDADADNNSLIRLFAPGQLKKYIASALAKSKIG<br>YVFIPPAGTSKTDPLTSKIGFRATGKYYKQLGYLLNKSDLYVERNGVIGKINSDVAA<br>AINILLKGVNHSIVPYRFLNKHAGSEQKRLKRFEGEIGCDLKKMPKTRLYYLDGKIIT<br>EEEKNSLEEALLAEIKHFLLSKANIPEFDAIPGSNGTCKAFSVPRCLKSRADPKKKRK<br>V |
| 30 | Amino acid sequence of Casδ-1D31-NLS fusion protein<br>MGPKKKRKVMDYKDHDGDYKDHDIDYKDDDDKNLAILEMREEVADYYADLQAD<br>YRHYLPLMILWGQNGFMEPDETGLNFSAVLPSTAKTRCENRYGAQIAADLKLIADD<br>LPSSLYAIFTNDYQPLTGVKKVGDRWKFVTSLNTVSDEEFAKKVKPLLRDYKGVTE<br>EQWRRFREERVAGKTADQVWDDLDSILRNPTLAALKKIHDKHMFRVKRPESKLYC<br>DALAHmLSSSYDSWKKINEARQLELQAMRDEQQGLLANKTTNSLYNLVCEFADEL<br>ESQNYGLTRRIFFIARKEWEDEKSHYLPVIKLLVTEKYLPLLQADNKTVSPAVKAWD<br>ICSTLKQRSPYIRFVPPTKDYPIPFGQTGRGHKFTLKEEAGKVCFLVPGLTKDEMPLS<br>GSHYFSSLRIDKVGTDFKISFRHKTKIRSKKSARVTVKQPRINGTVTEVGILRRNGKF<br>FLRVAYKIAYPQHNIDLKSYFASAAPSTQKLELLPAQMRVAGVDLNISDPIVVSKADI<br>FKGEDGGPLSVLDYGSGKVVGEPVIICKDTSRAGKISSLATKCRTLRDVIRNFRHSLH<br>QGTPLPSKSLEFLQEVPVAQEDLKSPSPRYLIQTWIKYIRTEMKRLHYKVWLDGYCH<br>TSEAMRmLDLVDQVAFLMKSYENIHVKPGHKIPKKTTASLKIRETSRTRFRLHVSRL<br>VGARVVRACEDCQMIFLEDLSTGFSEGSNNSLARLFSAGQLKNSIVMAAEKVGKAV<br>VFVCKDGTSIKDPVFGLHGLRPSKKTPGIPPDKKRLYVRRDGKIGYINADQAASLNV<br>LLVGLSHSVAKYKFFVKDGKLQDDEEVAAQQGKKPRKIGVRLERLLKMNFDTPAR<br>LFFSLEKDQVVPCYEATETPYTGWVYVYHDRLLTTRQRDQQVNQLAQEVKDLLRD<br>GVKIPKWDVIPDCDNSCLGFSPCLVLDDETAAVSVVSRADPKKKRKV |
| 31 | Nucleotide sequence of Casδ-1 system expression cassette<br>ATGGGACCAAAGAAGAAGAGAAAGGTTATGGATTACAAGGACCACGACGGAGA<br>CTATAAAGATCATGACATCGATTATAAGGATGATGATGACAAGATGTCTAAAGA<br>CGGGGACAAAATGAAACACTCCAAGCAAGAAGTTTCCGAGGACAAAGGCGTCA<br>AGAAAGATCCGTCCGTGTTTCGATGCCAGAACCTCGCCATACTCGAGATGAGGG<br>AGGAGGTCGCTGACTATTACGCAGACCTTCAGGCTGACTACCGGCACTACCTGC<br>CTCTGATGATTCTGTGGGGGCAAAATGGCTTTATGGAGCCAGATGAAACGGGCC<br>TCAACTTCAGCGCCGTCCTGCCGTCGACCGCGAAAACACGCTGTGAGAATAGGT<br>ATGGTGCCCAGATTGCAGCCGACCTGAAACTCATCGCAGATGATCTGCCGTCTA<br>GCCTGTATGCTATATTCACGAATGATTACCAGCCTTTAACTGGCGTGAAGAAGGT |

TABLE 1-continued

Description of sequences

| SEQ ID NO: | Description |
|---|---|
| | TGGTGACCGTTGGAAGTTTGTGACTTCATTGAACACCGTGTCGGATGAGGAATTT GCAAAGAAAGTCAAACCCCTCCTTCGCGACTACAAAGGTGTCACAGAGGAGCAG TGGCGTCGTTTCCGTGAGGAACGAGTTGCTGGGAAAACAGCCGACCAGGTTTGG GACGATCTCGATTCCATCTTGAGGAACCCGACGCTTGCCGCCCTCAAAAAGATT CATGACAAGCACATGTTCAGAGTTAAGAGGCCGGAGTCAAAGCTGTATTGTGAT GCATTGGCGCATATGCTCTCATCTTCATATGATTCATGGAAAAAGATCAATGAA GCACGTCAGTTGGAACTACAGGCCATGAGAGACGAACAACAAGGCCTGCTGGC AAATAAAACTACTAACTCTCTTTACAATCTGGTCTGTGAGTTCGCGGATGAGCTT GAATCACAAAACTACGGCCTGACCCGAAGGATATTCTTCATCGCCAGGAAAGAG TGGGAGGATGAAAAGTCGCACTACCTTCCTGTGATCAAACTCTTGGTGACCGAG AAGTATCTTCCACTTCTGCAGGCGGATAACAAAACAGTTTCTCCGGCGGTTAAG GCGTGGGATATTTGCAGCACGTTGAAGCAGCGCAGTCCATATATACGGTTCGTT CCTCCCACAAAAGACTATCCGATTCCATTTGGCCAGACAGGTAGGGGACACAAG TTTACACTCAAGGAGGAGGCCGGGAAGGTTTGCTTCCTGGTTCCAGGACTCACC AAGGATGAAATGCCACTCTCGGGCTCCCACTATTTCTCTAGTCTGCGAATTGACA AGGTCGGCACAGACTTCAAGATCAGCTTCCGCCATAAGACGAAGATTCGAAGCA AGAAGTCAGCTAGAGTGACCGTAAAACAACCTCGGATCAACGGCACCGTTACGG AGGTGGGTATCCTGCGTCGCAACGGCAAGTTTTTCTTACGGGTTGCGTACAAGAT TGCTTACCCGCAACACAACATTGATCTTAAGAGCTACTTCGCCAGCGCCGCCCCT TCCACTCAGAAGCTCGAGCTGCTCCCTGCTCAGATGAGGGTGGCGGGAGTCGAT TTGAACATTTCCGATCCCATCGTCGTATCCAAAGCTGATATTTTTAAGGGAGAGG ATGGAGGGCCATTATCGGTCTTGGACTACGGATCTGGCAAGGTAGTGGGCGAGC CCGTCATCATCTGTAAGGATACAAGTCGCGCAGGTAAAATCTCCTCGCTCGCGA CTAAGTGCCGCACCTTAAGAGACGTCATTCGGAATTTCCGCCACTCTCTCCATCA GGGAACCCCCCTACCCAGTAAGAGCCTGGAGTTTCTGCAGGAGGTGCCAGTGGC CCAGGAGGACCTAAAATCGCCATCCCCCAGGTATCTCATACAGACCTGGATAAA GTATATCAGAACAGAGATGAAGCGCTTGCATTATAAAGTGTGGTTGGACGGCTA CTGCCACACATCTGAAGCTATGCGTATGCTTGATCTAGTTGATCAGGTCGCCTTC CTCATGAAGTCATACGAAAACATACATGTGAAGCCGGGCCATAAAATTCCCAAG AAAACTACCGCGAGTCTCAAGATTAGGGAAACATCCAGGACGAGATTTAGACTG CATGTATCCAGGTTGGTCGGGGCCAGGGTGGTCCGCGCCTGTGAAGATTGTCAG ATGATCTTCCTGGAAGACTTGTCGACCGGCTTCTCAGAAGGTAGCAACAATAGC CTCGCGCGGCTGTTTAGCGCCGGCCAGCTGAAGAATAGTATAGTGATGGCGGCG GAGAAGGTGGGTAAAGCTGTTGTATTTGTCTGCAAGGATGGAACTAGCATAAAG GACCCTGTCTTCGGTTTACACGGCCTTCGGCCGTCGAAAAAGACCCCAGGCATC CCTCCGGATAAAAAAAGACTTTATGTGAGACGGGATGGTAAGATTGGGTACATC AATGCTGATCAAGCTGCAAGTCTGAATGTACTATTGGTAGGTCTGAGCCATAGT GTGGCCAAGTACAAGTTCTTCGTCAAAGATGGTAAGTTGCAGGATGACGAAGAG GTGGCGGCACAACAAGGAAAGAAGCCTAGGAAGATTGGCGTTCGCCTGGAAAG ACTACTAAAGATGAATTTTGATACCCCGGCCCGCCTTTTTTTTAGCCTGGAGAAG GACCAGGTGGTTCCGTGCTACGAGGCGACTGAGACGCCTTACACGGGTTGGGTG TACGTCTACCATGACAGGCTTCTCACAACACGCCAGAGGGACCAACAGGTGAAT CAACTTGCCCAAGAGGTGAAAGACTTACTTAGGGACGGGGTGAAGATCCCTAAA TGGGACGTGATCCCAGACTGCGACAACAGTTGCCTCGGGTTCTCTCCCTGCCTGG TGCTTGACGACGAGACTGCTGCTGTCTCAGTTGTTGGATCTGGGAGCAAGCGGC CCGCAGCAACGAAAAAGGCAGGGCAAGCAAAAAAGAAGAAATGA |
| 32 | Nucleotide sequence of Casδ-2 system expression cassette ATGGGTCCGAAAAAGAAGCGGAAAGTTATGGATTATAAGGATCATGATGGCGA CTATAAGGATCATGACATAGATTATAAAGATGATGACGACAAAATGGAATTGAA GACAACTTTTTGTCAGTCACTAAAAATTAAGATCCTCCCCGAAAGCCATAAGTTG TATTACGATGAGCTGCAAGCCGACCTAAAGAAGATGAGAATCTTCTTCGCAACG CACTCTGGGCTCAACTACAGCTACAAGGAAGATGAAAACGATTCGGAATGGAAG ATAGCGTCGTCAAAAAAGAGCACACTCTCACCTGAAGCCCAAAGGCTTATTGAC ATCATCGCCAAAGGCGGTATAGGAGCAGAGCACGCCTACGGAATATTTTACAAG GACAAAAAGGTGTCGGACAAGATCCGGCGAGATAATTCAAACTGCATCTTCGCC ATGCTATTACCTAACCTCGTCAATTTCGAGGAAGAATACAAAAAGAGGAAAAGT AAGCTCCAGCTCACCAAGGAAGAGTGGGAGGAGTACCATAAACGATGTCTTGCA GGCGAGAGCGTGGAAGTCCTGTGGTCCGAGGAGATTGCTCCAAAAATTGGGCCT AACGAAGCGGCGAGACTGGCATCACTCGCGTATCACCAGTTCCCAGATTCTCGT CATCCGGCGGACATTACCCACTGCAGGGCGCTCATGTCTATGGTAGCAGACTCTT TTTGTTCCTGGGTCGAGTGCCACAAGCTGCACCGTGAGGAAACAGAGAAACTCA AGACGAAATTACAGGAGAAGATAGAGAGCTGCAAGGAGGCATACAATCTGCTA CTCGCTTATTCCGAAGACCTGTACAGTAGGAATTATGGTCTGAGTGCCAGGGTTT TGAAGGCACTTATTGACAACAAATCCCGGTGCTGCTTCGACATAGCCTTTCAGAT CGCGGAGAAATATCCTGCACTGATGAAGATTGATGAAAAGACCCTGTTCAAGGC CTACAACGCCCTAAAGCTCCACTGGAAAATAAAACGACGCAAGCCGTTCATCTC GCTGCCCAAGATCGAGAGGGACTACCAGGTGCCCTTTGGACTCACAGGAAGCAG AGGCAAGAAGTTCGACGTCTATGTGGAAAACAAGAATATTGTGGTCGAGATCGA CGGCCAGAAAGTCGAAACCTTCAGCTCTCACTATTTCTCTGATATGCAGATCTCC AAGATTTACGGTGAAAAGAAAAAATTTGAAGGGATTCAAGTTGAAATTCCGCCAC AAGCTGAAGGACAAGAAGAAGGAGGTTTATGGAGAGTGGATTGAGGCGGAGCT GAAGGAAATCAAGATTAAGAAAGACATGGAGACAGGCGACTTCTACCTGTATCT CCCATACACTACAACGCATAATGAGAAAAACTTATTGCTCGAGAAGTTCTTTTCC |

TABLE 1-continued

| SEQ ID NO: | Description |
|---|---|
| | Description of sequences |
| | TACGCCGATCCACTTAAGGAGACTATTTTTAAGAACGGAAAGACGGAGCTTCCA AATGAATTTCTAGGCTTCGGCTTCGATTTGAACCTTTCCGACCCGATTGCGATGG CGGTTGCCGAGTTTGTTCGGGACTCATCAGATGGTGAGATTGGCGCCCTCGACTA TGGTCACGGTAAGCTCCTCGACGCTAGTGTTTTGGTCTGCAACTCATCACTATCA AAGCGCATCAATGACCTGGTTGGAGACAATAGAAAGCTGATCCAAGCTATTAGA TCGTACAAGAACTCGCTAGTAACTAAGGAAATGGACGAGGAGAGTGGCGAGTG GCTTAAAAAAGCTCTAGGCAATGCAAAGTACGGCAACCATAGGCATCAGCTTCA ACTGGTCATGTCTAAGCTGAACAAAAAAAGCAAAAAGTACTGGCAGGAATGTCG CAAGAACGGCCACAACGATCTTTCCGAAAATATTGCACTATTAAAGTTGTTGGA CGTGCAGTTCTCTTTGCATAAAAGCTATAACAACATACACATCTTTGATTACAAA AAACAAATTCACAGCCATAAGACTGACTCCAAAAGGGAGAATTTCCGTGAATTT GTGACGAAGCAATTTGCGGCTACCATAGTAAAGCATTGCAAGGAGGTGATGGCT AAATATGGCAGAGAGTACGCCGTTGTCTTTTTGGAGGACCTGGAGATGTACTTT GATGCTGATGCTGATAACAATTCTCTGATCCGGCTTTTTGCACCCGGCCAATTGA AGAAGTACATCGCCTCCGCTCTGGCTAAGAGCAAGATAGGTTATGTGTTCATCC CTCCTGCTGGGACAAGTAAGACCGACCCGTTAACTTCGAAAATTGGATTCAGGG CTACCGGAAAATACTACAAGCAGCTGGGCTATCTGCTTAATAAGTCCGACCTCT ACGTGGAGCGCAACGGGGTTATCGGGAAGATCAACAGTGATGTAGCTGCGGCG ATAAATATTCTCTTAAAGGGCGTGAACCACTCAATCGTGCCGTACCGCTTCCTGA ATAAACATGCTGGGTCTGAACAGAAGCGCCTCAAACGTTTTGAAGGGGAGATCG GTTGTGATCTGAAAAAGATGCCAAAGACACGCCTCTACTATCTTGACGGAAAAA TCATCACTGAAGAGGAGAAGAACAGCCTGGAGGAAGCGCTACTCGCTGAGATC AAGCACTTCCTTCTGTCGAAGGCCAACATTCCGGAGTTTGATGCAATACCGGGG AGCAATGGCACCTGCAAAGCCTTCTCCGTTCCACGCTGCCTTAAGGGCAGCGGG AGCAAGCGGCCCGCCGCGACCAAAAAAGCGGGGCAAGCCAAGAAGAAAAAGTG A |
| 33 | Nucleotide sequence of Casδ-1D31 system expression cassette ATGGGACCAAAGAAGAAGAGAAAGGTTATGGATTACAAGGACCACGACGGAGA CTATAAAGATCATGACATCGATTATAAGGATGATGATGACAAGAACCTCGCCAT ACTCGAGATGAGGGAGGAGGTCGCTGACTATTACGCAGACCTTCAGGCTGACTA CCGGCACTACCTGCCTCTGATGATTCTGTGGGGGCAAAATGGCTTTATGGAGCC AGATGAAACGGGCCTCAACTTCAGCGCCGTCCTGCCGTCGACCGCGAAAACACG CTGTGAGAATAGGTATGGTGCCCAGATTGCAGCCGACCTGAAACTCATCGCAGA TGATCTGCCGTCTAGCCTGTATGCTATATTCACGAATGATTACCAGCCTTTAACT GGCGTGAAGAAGGTTGGTGACCGTTGGAAGTTTGTGACTTCATTGAACACCGTG TCGGATGAGGAATTTGCAAAGAAAGTCAAACCCCTCCTTCGCGACTACAAAGGT GTCACAGAGGAGCAGTGGCGTCGTTTCCGTGAGGAACGAGTTGCTGGGAAAACA GCCGACCAGGTTTGGGACGATCTCGATTCCATCTTGAGGAACCCGACGCTTGCC GCCCTCAAAAAGATTCATGACAAGCACATGTTCAGAGTTAAGAGGCCGGAGTCA AAGCTGTATTGTGATGCATTGGCGCATATGCTCTCATCTTCATATGATTCATGGA AAAAGATCAATGAAGCACGTCAGTTGGAACTACAGGCCATGAGAGACGAACAA CAAGGCCTGCTGGCAAATAAAACTACTAACTCTCTTTACAATCTGGTCTGTGAGT TCGCGGATGAGCTTGAATCACAAAACTACGGCCTGACCCGAAGGATATTCTTCA TCGCCAGGAAAGAGTGGGAGGATGAAAAGTCGCACTACCTTCCTGTGATCAAAC TCTTGGTGACCGAGAAGTATCTTCCACTTCTGCAGGCGGATAACAAAACAGTTTC TCCGGCGGTTAAGGCGTGGGATATTTGCAGCACGTTGAAGCAGCGCAGTCCATA TATACGGTTCGTTCCTCCCACAAAAGACTATCCGATTCCATTTGGCCAGACAGGT AGGGGACACAAGTTTACACTCAAGGAGGAGGCCGGGAAGGTTTGCTTCCTGGTT CCAGGACTCACCAAGGATGAAATGCCACTCTCGGGCTCCCACTATTTCTCTAGTC TGCGAATTGACAAGGTCGGCACAGACTTCAAGATCAGCTTCCGCCATAAGACGA AGATTCGAAGCAAGAAGTCAGCTAGAGTGACCGTAAAACAACCTCGGATCAAC GGCACCGTTACGGAGGTGGGTATCCTGCGTCGCAACGGCAAGTTTTTCTTACGG GTTGCGTACAAGATTGCTTACCCGCAACACAACATTGATCTTAAGAGCTACTTCG CCAGCGCCGCCCCTTCCACTCAGAAGCTCGAGCTGCTCCCTGCTCAGATGAGGG TGGCGGGAGTCGATTTGAACATTTCCGATCCCATCGTCGTATCCAAAGCTGATAT TTTTAAGGGAGAGGATGGAGGGCCATTATCGGTCTTGGACTACGGATCTGGCAA GGTAGTGGGCGAGCCCGTCATCATCTGTAAGGATACAAGTCGCGCAGGTAAAAT CTCCTCGCTCGCGACTAAGTGCCGCACCTTAAGAGACGTCATTCGGAATTTCCGC CACTCTCTCCATCAGGGAACCCCCCTACCCAGTAAGAGCCTGGAGTTTCTGCAG GAGGTGCCAGTGGCCCAGGAGGACCTAAAATCGCCATCCCCCAGGTATCTCATA CAGACCTGGATAAAGTATATCAGAACAGAGATGAAGCGCTTGCATTATAAAGTG TGGTTGGACGGCTACTGCCACACATCTGAAGCTATGCGTATGCTTGATCTAGTTG ATCAGGTCGCCTTCCTCATGAAGTCATACGAAAACATACATGTGAAGCCGGGCC ATAAAATTCCCAAGAAAACTACCGCGAGTCTCAAGATTAGGGAAACATCCAGGA CGAGATTTAGACTGCATGTATCCAGGTTGGTCGGGGCCAGGGTGGTCCGCGCCT GTGAAGATTGTCAGATGATCTTCCTGGAAGACTTGTCGACCGGCTTCTCAGAAG GTAGCAACAATAGCCTCGCGCGGCTGTTTAGCGCCGGCCAGCTGAAGAATAGTA TAGTGATGGCGGCGGAGAAGGTGGGTAAAGCTGTTGTATTTGTCTGCAAGGATG GAACTAGCATAAAGGACCCTGTCTTCGGTTTACACGGCCTTCGGCCGTCGAAAA AGACCCCAGGCATCCCTCCGGATAAAAAAAGACTTTATGTGAGACGGGATGGTA AGATTGGGTACATCAATGCTGATCAAGCTGCAAGTCTGAATGTACTATTGGTAG GTCTGAGCCATAGTGTGGCCAAGTACAAGTTCTTCGTCAAAGATGGTAAGTTGC AGGATGACGAAGAGGTGGCGGCACAACAAGGAAAGAAGCCTAGGAAGATTGGC |

TABLE 1-continued

| SEQ ID NO: | Description of sequences<br>Description |
|---|---|
| | GTTCGCCTGGAAAGACTACTAAAGATGAATTTTGATACCCCGGCCCGCCTTTTTT TTAGCCTGGAGAAGGACCAGGTGGTTCCGTGCTACGAGGCGACTGAGACGCCTT ACACGGGTTGGGTGTACGTCTACCATGACAGGCTTCTCACAACACGCCAGAGGG ACCAACAGGTGAATCAACTTGCCCAAGAGGTGAAAGACTTACTTAGGGACGGGG TGAAGATCCCTAAATGGGACGTGATCCCAGACTGCGACAACAGTTGCCTCGGGT TCTCTCCCTGCCTGGTGCTTGACGACGAGACTGCTGCTGTCTCAGTTGTTGGATC TGGGAGCAAGCGGCCCGCAGCAACGAAAAAGGCAGGGCAAGCAAAAAAGAAG AAATGA |
| 34 | PAM library sequence<br>NNNNNNNNGGTATAACAACTTCGACGAGCTCTACA |
| 35 | Target sequences for PAM recognition site identification of Casδ-1<br>GGUAUAACAACUUCGACGAGCUCUACA |
| 36 | Guide sequence of in vitro enzyme digestion of Casδ-1<br>GGUAUAACAACUUCGACGAGCUCUACA |
| 37 | Guide sequence of Casδ-1 in maize<br>CGGUGGGCUGGCGCUGGGGUUCAGCU |
| 38 | Guide sequence of sg1 of Casδ-1 in human cells<br>GAGCCAGAGAGGAUCCUGGGAGGGAG |
| 39 | Guide sequence of sg2 of Casδ-1 in human cells<br>UGACUUUGUCACAGCCCAAGAUAGUU |
| 40 | Guide sequence of sg3 of Casδ-1 in human cells<br>AAACCCAGACACAUAGCAAUUCAGGA |
| 41 | Guide sequence of sg4 of Casδ-1 in human cells<br>CUGAGGGGCUGCUGGUUUGGCUGGUG |
| 42 | Guide sequence of sg5 of Casδ-1 in human cells<br>GAGAUGCCAGCAGAAGUUGGGCAGAA |
| 43 | Guide sequence of sg6 of Casδ-1 in human cells<br>GGGCAGAGUGGAGAUGGUGGGGACAA |
| 44 | Guide sequence of sg7 of Casδ-1 in human cells<br>ACUAGGGUGGGCAACCACAAACCCAC |
| 45 | Guide sequence of sg8 of Casδ-1 in human cells<br>UGUACAGAAGGCUGAAAGGAGAGAAC |
| 46 | Guide sequence of sg9 of Casδ-1 in human cells<br>CGGUACCAGUUUAGCACGAAGCUCUC |
| 47 | Guide sequence of sg10 of Casδ-1 in human cells<br>CCACCAUUGUCUUUCCUAGCGGAAUG |
| 48 | Guide sequence of sg11 of Casδ-1 in human cells<br>AAGCACUGUGGGUACGAAGGAAAUGA |
| 49 | Guide sequence of sg12 of Casδ-1 in human cells<br>UGUCACAAAGUAAGGAUUCUGAUGUG |
| 50 | Guide sequence of sg13 of Casδ-1 in human cells<br>CUGUUGUUGAAGGCGUUUGCACAUGC |
| 51 | Guide sequence of sg14 of Casδ-1 in human cells<br>UCUGCAGGCCAGAUGAGGGCUCCAGA |
| 52 | Guide sequence of AAVS1-ATG PAM in Casδ-1 human cells<br>GAGCCAGAGAGGAUCCUGGGAGGGAG |
| 53 | Guide sequence of AAVS1-ATA PAM in Casδ-1 human cells<br>GACCACUGUGUGGGGGUAAAGGACCU |
| 54 | Guide sequence of AAVS1-ACA PAM in Casδ-1 human cells<br>CCCCCAUUUCCUGGAGCCAUCUCUCU |
| 55 | Guide sequence of AAVS1-GCA PAM in Casδ-1 human cells<br>AACCUUAGAGGUUCUGGCAAGGAGAG |

TABLE 1-continued

| SEQ ID NO: | Description |
|---|---|
| 56 | Guide sequence of AAVS1-GTA PAM in Casδ-1 human cells AGCAAACCUUAGAGGUUCUGGCAAGG |
| 57 | Guide sequence of AAVS1-ACG PAM in Casδ-1 human cells AUGGAGCCAGAGAGGAUCCUGGGAGG |
| 58 | Guide sequence of AAVS1-GTG PAM in Casδ-1 human cells GGAGGGAAGGGGGGGAUGCGUGACCU |
| 59 | Guide sequence of AAVS1-GCG PAM in Casδ-1 human cells UGACCUGCCCGGUUCUCAGUGGCCAC |
| 60 | Guide sequence of Casδ-1T26 GAGCCAGAGAGGAUCCUGGGAGGGAG |
| 61 | Guide sequence of Casδ-1T24 GAGCCAGAGAGGAUCCUGGGAGGG |
| 62 | Guide sequence of Casδ-1T22 GAGCCAGAGAGGAUCCUGGGAG |
| 63 | Guide sequence of Casδ-1T21 GAGCCAGAGAGGAUCCUGGGA |
| 64 | Guide sequence of Casδ-1T20 GAGCCAGAGAGGAUCCUGGG |
| 65 | Guide sequence of Casδ-1T19 GAGCCAGAGAGGAUCCUGG |
| 66 | Guide sequence of Casδ-1T18 GAGCCAGAGAGGAUCCUG |
| 67 | Guide sequence of Casδ-1T16 GAGCCAGAGAGGAUCC |

Specific Models for Carrying Out the Invention

The present invention is now described with reference to the following examples which are intended to illustrate the present invention (but not to limit the present invention).

Unless otherwise specified, the experiments and procedures described in the examples were basically performed according to the methods known in the art and using conventional methods described in various references. For example, conventional techniques of immunology, biochemistry, chemistry, molecular biology, microbiology, cell biology, genomics and recombinant DNA used in the present invention can be found in Sambrook, Fritsch, and Maniatis, MOLECULAR CLONING: A LABORATORY MANUAL, 2nd ed. (1989); CURRENT PROTOCOLS IN MOLECULAR BIOLOGY, edited by F. M. Ausubel et al. (1987)); METHODS IN ENZYMOLOGY series, Academic Press: PCR 2: A PRACTICAL METHOD APPROACH, edited by M. J. MacPherson, B. D. Hames, and G. R. Taylor (1995); ANTIBODIES, A LABORATORY MANUAL, edited by Harlow and Lane (1988); and, ANIMAL CELL CULTURE, edited by R. I. Freshney (1987).

In addition, when specific conditions were not specified in the examples, they were carried out under conventional conditions or conditions recommended by the manufacturer. The reagents or instruments used without indicating the manufacturer were all conventional products that could be obtained commercially. It is known to those skilled in the art that the examples describe the present invention by way of example, and are not intended to limit the scope sought to be protected by the present invention. All publications and other references mentioned herein are incorporated herein by reference in their entirety.

The sources of some reagents involved in the following examples were as follows:

LB liquid culture medium: 10 g of tryptone, 5 g of yeast extract, 10 g of NaCl, diluted to 1 L, and sterilized. If the addition of an antibiotic was required, it was added after the culture medium was cooled down, and its final concentration was 50 μg/mL.

Chloroform/isoamyl alcohol: 240 mL of chloroform was added with 10 mL of isoamyl alcohol, and mixed well.

RNP buffer: 100 mM sodium chloride, 50 mM Tris-HCl, 10 mM $MgCl_2$, 100 μg/mL BSA, pH 7.9.

Prokaryotic expression vectors pET-30a, pUC19, and pACYCDuet-1 were purchased from Beijing Quanshijin Biotechnology Co., Ltd.

*Escherichia coli* competent TSC-E03 was purchased from Beijing Qingke Biotechnology Co., Ltd.

Example 1. Acquisition of Casδ Sequences and Casδ Guide RNA

1. Annotation of CRISPR and genes: Prodigal was used to perform the gene annotation of the data of microbial genome and metagenome of NCBI and JGI databases to obtain all proteins, and Piler-CR was used to perform the annotation of CRISPR loci, and the parameters were all default parameters.

2. Protein filtering: The annotated proteins were subjected to redundancy removal through sequence consistency so as to remove proteins with completely identical sequences.

3. Acquisition of CRISPR-related proteins: Each CRISPR locus was extended by 10 Kb upstream and downstream, and the non-redundant proteins in the CRISPR adjacent interval were identified.

4. Clustering of CRISPR-related proteins: BLASTP was used to perform internal pairwise alignment of non-redundant CRISPR-related proteins, and the alignment results with Evalue<1E−10 were outputted. MCL was used to perform clustering analysis on the output results of BLASTP, CRISPR-related protein families.

5. Identification of CRISPR-enriched protein families: BLASTP was used to align the proteins of the CRISPR-related protein families to the non-redundant proteins databases from which the non-CRISPR-related proteins were removed, and the alignment results with Evalue<1E−10 were outputted. If the homologous proteins found in a non-CRISPR-related protein database were less than 100%, it meant that the proteins of this family were enriched in the CRISPR region. In this way, the CRISPR-enriched protein families were identified.

6. Annotation of protein functions and domains: The CRISPR-enriched protein family was annotated using the Pfam database, the NR database, and the Cas proteins collected from NCBI to obtain a new CRISPR/Cas protein family. Multiple sequence alignment of each CRISPR/Cas family protein was performed using Mafft, and then conserved domain analysis was performed using JPred and HHpred to identify the protein family containing RuvC domain.

On this basis, the inventors obtained some new Cas effector proteins, which were named Casδ-1 and Casδ-2, respectively, the sequences of the proteins were set forth in SEQ ID NO: 1 and SEQ ID NO: 2, and the nucleotide sequences encoding the proteins were as set forth in SEQ ID NO: 4 and SEQ ID NO: 5. The direct repeat sequences (the repeat sequences contained in pre-crRNA) corresponding to Casδ-1 and Casδ-2 were set forth in SEQ ID NO: 7 and SEQ ID NO: 8.

Example 2. Description of Sequence Structure of Casδ Gene

1. The CRISPR/Casδ sequence fragment was synthesized by Beijing Qingke Biotechnology Co., Ltd. and constructed into the protein expression vector pET-30a (+), and the first generation sequencing was performed for confirmation. According to the sequencing results, the recombinant plasmid pET-30a+CRISPR/Casδ was described as follows:

(1) The recombinant plasmid pET-30a+CRISPR/Casδ-1 contained an expression cassette, and the expression cassette sequence was set forth in SEQ ID NO: 31. In the sequence as set forth in SEQ ID NO: 31, from the 5' end, positions 1 to 27 were the nucleotide sequence of SV40-NLS, positions 28 to 96 were the nucleotide sequence of 3×FLAG, positions 97 to 2904 are were nucleotide sequence of Casδ-1, and positions 2905 to 2964 were the nucleoplasmin NLS signal peptide.

(2) The recombinant plasmid pET-30a+CRISPR/Casδ-2 contained an expression cassette, and the expression cassette sequence was set forth in SEQ ID NO: 32. In the sequence as set forth in SEQ ID NO: 32, from the 5' end, positions 1 to 27 were the nucleotide sequence of SV40-NLS, positions 28 to 96 were the nucleotide sequence of 3×FLAG, positions 97 to 2697 were the nucleotide sequence of Casδ-2, and positions 2698 to 2757 were the nucleoplasmin NLS signal peptide.

Example 3. Identification of PAM and DNA Cleavage Mode of CRISPR/Casδ System

I. In Vitro Expression and Purification of Casδ Protein

The specific steps of in vitro expression and purification of Casδ protein were as follows:

1. Artificial synthesis of nucleotide sequences as set forth in SEQ ID NOs: 31 to 32.

2. The recombinant plasmids pET-30a-CRISPR/Casδ-1 and pET-30a-CRISPR/Casδ-2 were introduced into *E. coli* TSC-E03 to obtain recombinant bacteria, and the recombinant bacteria were named TSC-E03-CRISPR/Casδ-1 and TSC-E03-CRISPR/Casδ-2. The single clones of TSC-E03-CRISPR/Casδ-1 and TSC-E03-CRISPR/Casδ-2 were picked out, inoculated into 100 mL of LB liquid culture medium (containing 50 μg/mL kanamycin), and cultured under shaking at 37° C. and 200 rpm for 12 h to obtain culture solutions.

3. The culture solutions were taken and inoculated into 50 mL of LB liquid culture medium (containing 50 μg/mL kanamycin) at a volume ratio of 1:100, cultured under shaking at 37° C. and 200 rpm until the $OD_{600\ nm}$ value was 0.6, then IPTG was added to have a concentration of 1 mM, cultured under shaking at 18° C. and 220 rpm for 14 h, and centrifuged at 4° C. and 7000 rpm for 10 min to obtain bacterial precipitates.

5. The bacterial precipitates were taken, added with 100 mL of pH 8.0, 100 mM Tris-HCl buffer, resuspended and ultrasonically disrupted (ultrasonic power was 600 W, and cycle program was: disruption 4 s, stop 6 s, total 20 min), and then centrifuged at 4° C., 10000 rpm for 10 min to collect Supernatant A.

6. Supernatant A was taken, centrifuged at 4° C., 12000 rpm for 10 min to collect Supernatant B.

7. The nickel column produced by GE was used to purify Supernatant B (referring to the instructions of the nickel column for the specific steps of purification), and then the protein quantification kit produced by Thermo Fisher was used to quantify Casδ-1 to Casδ-3 proteins.

II. Transcription and Purification of Casδ Protein Guide RNA:

1. The templates for guide RNA transcription were designed respectively. The structure of the transcription templates were: (1) T7 promoter+direct repeat sequence of Casδ-1 and Casδ-2 (SEQ ID NOs: 7 to 8)+guide sequence (SEQ ID NO: 36). The primers were designed using Primer5.0 software to ensure that the Forward primer and Reward primer had at least 18 bp of overlapping sequence.

2. The following reaction system was prepared, gently blown and beaten and mixed well, then centrifuged briefly, and placed in a PCR instrument for slow annealing. The PCR system was as follows:

| Component | Volume (μL) |
|---|---|
| Forward Primer (100 nM) | 7.5 |
| Reward Primer (100 nM) | 7.5 |
| 2*KAPA Mix | 25 |
| $ddH_2O$ | 10 |
| Total volume | 50 |

3. MinElute PCR Purifcation Kit was used to purify the template, and the steps were as follows:

1) The PCR product was added with PB of 5 times volume, and a MinElute column was placed on a 2 mL collection tube, allowed to stand at room temperature for 2 min, and centrifuged at 12000 g for 1 min;
2) The waste liquid was discarded, and 750 μL of Buffer PE (ethanol was added before use) was added and centrifuged at 12000 g for 1 min;
3) The waste liquid was discarded, 350 μL of Buffer PE was added and centrifuged at 12000 g for 1 min, then the waste liquid was added, and centrifugation was performed at 12000 g for 2 min;
4) The MinElute column was placed on a new 1.5 mL centrifuge tube, the lid was opened, and standing was performed at 65° C. for 2 min;
5) 20 μL of preheated EB solution was added, allowed to stand for 2 min, and centrifuged at 12000 g for 2 min. In order to improve the recovery rate, the content of the centrifuge tube could pass through the MinElute centrifuge column 2 to 3 times;
6) The template was measured for concentration by Nanodrop, and frozen at −20° C. for later use.

4. Purification of guide RNA: DNaseI in the system was extracted and removed with phenol: chloroform: isoamyl alcohol (25:24:1);

1) 80 μL of RNA free $H_2O$ was added to the post-transcription reaction system to adjust the volume to 100 L;
2) 2 mL of Phase Lock Gel (PLG) Heavy was taken out, centrifuged at 15000 g for 2 min, and added with 100 μL of phenol: chloroform: isoamyl alcohol (25:24:1), and 100 μL of RNA digested with DNAseI, and the Phase-Lock tube was gently flicked 5 to 10 times by hand to mix evenly, and then centrifuged at 15° C. and 16000 g for 12 min;
3) A new RNA-free 1.5 mL centrifuge tube was taken, the supernatant was pipetted from the previous centrifugation and added to the centrifuge tube without pipetting the gel, then added with isopropanol of the same volume as the supernatant and sodium acetate solution of the one-tenth the volume, mixed well with a pipette tip, and placed into a −20° C. refrigerator for 1 h or overnight;
4) Centrifugation was performed at 4° C., 16000 g for 30 min, the supernatant was discarded, 75% pre-cooled ethanol was added, the precipitate was mixed well by pipetting, and centrifuged at 4° C., 16000 g for 12 min, the supernatant was discarded, then it was allowed to stand in a fume hood for 2 to 3 min, the ethanol on RNA surface was dried in the air, 100 μL of RNA free $H_2O$ was added, and mixed well by pipetting.

5. The purified crRNA was measured for concentration by Nanodrop, and uniformly diluted to 250 ng/μL, divided into 200 μL PCR centrifuge tubes, and frozen at −80° C. for later use.

III. Casδ Protein In Vitro Enzyme Digestion and PAM Consumption:

1. Establishment of Double-Stranded DNA Enzyme Digestion System:

(1) The following reaction system was prepared, gently pipetted and mixed well, and then centrifuged briefly. It was placed at 37° C. for 15 min; and the DNA cleavage reaction system was as follows:

| Component | Sample amount |
|---|---|
| 12δ-crRNA (250 ng/μL) | 600 ng |
| 12δ protein (0.5 μg/μL) | 0.5 μg |
| 10*DNA Cleavage buffer | 1 μL |
| RNA-Free $H_2O$ | Supplemented to 7 μL |

(2) 300 ng of substrate DNA (100 ng/μL), 3 μL, was added, gently pipetted to mix well and then centrifuged briefly. It was placed at 37° C. for 8 h;
(3) RNAse was added, placed at 37° C. for 15 min to fully digest the RNA impurities in the system;
(4) Proteinase K was added, placed at 58° C. for 15 min to digest Casδ-1 to 3 proteins;
(5) Detection was performed by running agarose gel.

The gel results showed that Casδ-1 was capable of effectively cleaving double-stranded DNA.

2. Identification of PAM Site:

(1) The reaction system as in step 6 above was prepared, the substrate DNA was replaced with a plasmid library with 8 random bases before target, and placed at 37° C. for 8 h, and the secondary control sample was a sample with Casδ added but no crRNA added. Three repeats were set for each protein;
(2) After the reaction, the reaction sample was subjected to column purification, and the purified product was used as a template to construct the second-generation library. The system and method for library construction were the same as the library construction method in step 2 of PAM library consumption in *Escherichia coli*. The specific operation process was as follows:

(Each sample corresponded to one R-directed primer, and corresponded to multiple F-directed primers), the following reagents were prepared:

| Reagent | Usage amount |
|---|---|
| Template | 20 ng |
| High-fidelity PCR mix | 20 μL |
| NGS-Lib-Fwd-1-10 | 2 μL |
| NGS-Lib-Rev | 2 μL |
| distilled water | Supplemented to 40 μL |

The prepared reaction system was loaded in a PCR instrument, and the program was as follows:

| Temperature | Time |
|---|---|
| 98° C. | 3 min |
| 98° C. | 15 s |
| 60° C. | 30 s |
| 72° C. | 20 s |
| Go to step 2 | 20 cycles |
| 72° C. | 5 min |
| 10° C. | forever |

Figure 1B:
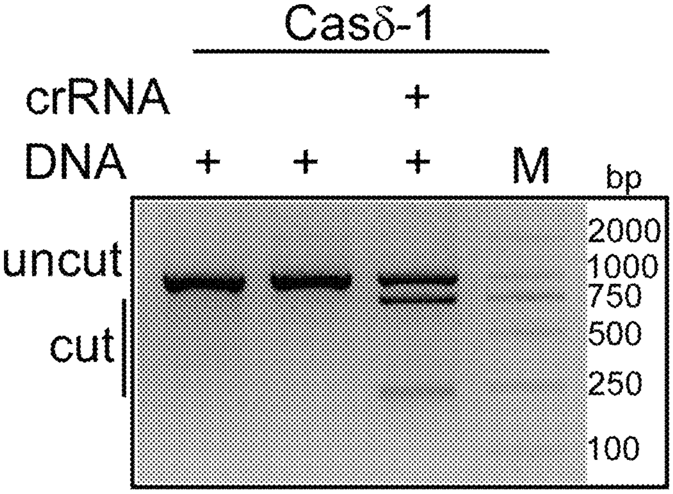

Sequencing 1G for each sample;

(3) The numbers of occurrences of the combined PAM sequences in the experimental group and the control group were counted, respectively, and standardized with the number of all PAM sequences in each group. For any PAM sequence, when log 2 (normalized value of the control group/normalized value of the experimental group) was greater than 3.5, it was believed that this PAM was significantly consumed. The significantly consumed PAM sequences were obtained from all PAM sequences. In addition, Weblogo was used to predict the significantly consumed PAM sequences, and finally the PAM domains of Casδ were obtained (FIG. 1A and FIG. 1B).

Figure 2:
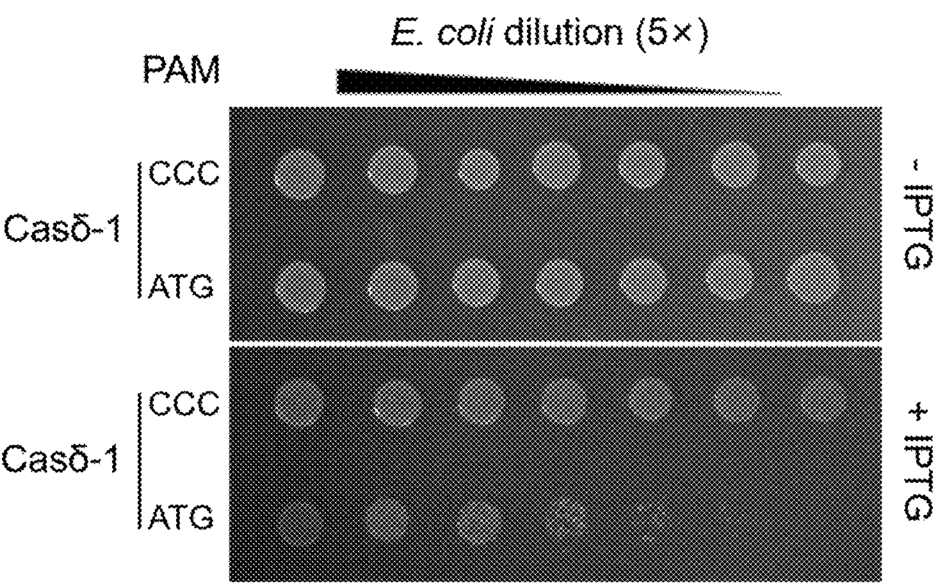
FIG. 2 shows the verification of the PAM recognition site of Casδ-1 in *Escherichia coli* in Example 3.

(4) Verification of PAM library domains: Through the PAM library consumption experiment, we obtained the PAM domain of Casδ-1. In order to verify the rigor of this domain, we set up ATG PAM for in vivo experiments to test the editing activity of Casδ-1 on this PAM. First, we integrated the 26 nt target of the T7 promoter with the corresponding PAM site and the sequence of the T7 terminator into the vector pET30a-Casδ-1, which was then co-transfected with the pACYCDuet-1 plasmid and coated on kanamycin and chloramphenicol resistance plates for screening. The monoclonal plaques with double resistance were selected for shaking bacteria, and IPTG induction was performed for 12 hours at an OD value of 1.0. Then, the bacteria before and after induction were observed by gradient dilution. If the chloramphenicol gene was edited, the growth on the chloramphenicol resistance plate was poor. Through the experimental results (FIG. 2 and FIG. 3), we could see that CRISPR/Casδ-1 could only effectively edit target sequences with specific PAM domains (e.g., ATG), but had no editing activity on the rest of the target sequences (e.g., CCC), thus verifying the accuracy of Casδ-1 for recognition of PAM domains. Through the above experimental results, it was confirmed that Casδ-1 had a rigorous PAM recognition mode, so Casδ-1 could significantly reduce off-target effects.

Figure 3:
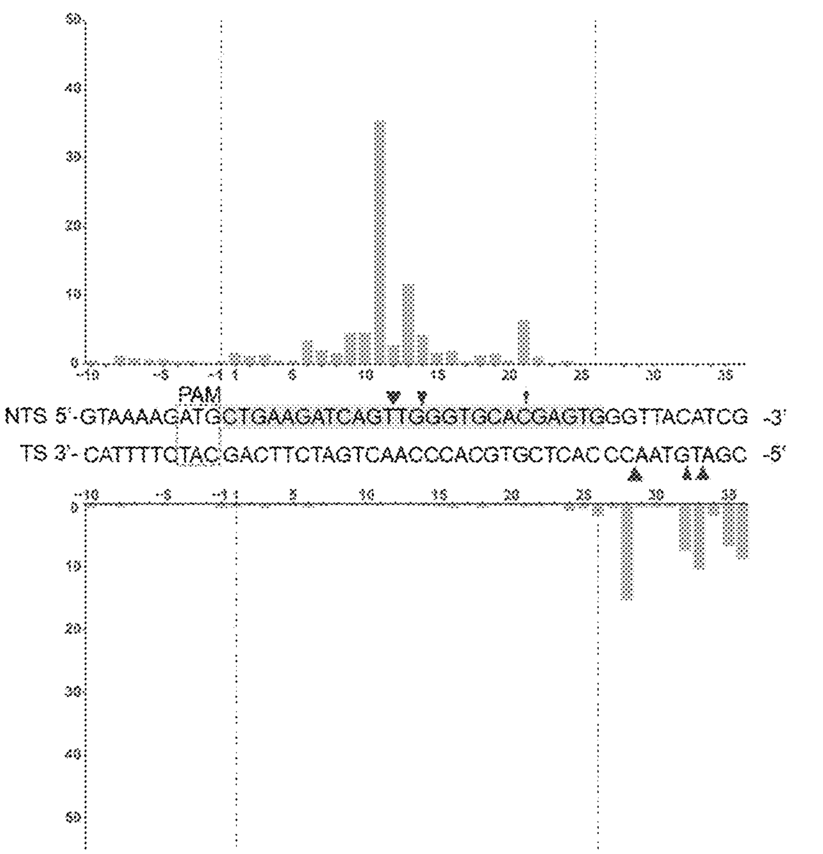
FIG. 3 shows the analysis of the cleavage characteristics of Casδ-1 protein on the target sequence in Example 3.

(5) Analysis of dsDNA cleavage mode of Casδ-1 protein:

In order to further determine the cleavage site and substrate cleavage mode of Casδ-1 protein when targeting dsDNA, the cut bands after enzymatic digestion of Casδ-1 protein-targeted substrate dsDNA were individually cut and recovered. Since the dsDNA fragments were designed with the 26 nt target site at a greater distance from the 5' end than from the 3' end, bands with larger fragment lengths were subjected to the first-generation sequencing using F-direct primers that amplified linear dsDNA fragments, while the recovered bands with shorter fragment lengths were sequenced with R-direct primers as amplified. By aligning the results of the first-generation sequencing to the reference dsDNA sequence, the cleavage site of the Casδ-1 protein for the substrate was located at 18 nt and 19 nt far from the PAM, thereby forming a sticky end with a 1 nt protrusion (FIG. 3).

Example 4. Analysis of Trans-Cleavage Activity of CRISPR/Casδ System

A single-stranded or double-stranded DNA without SEQ ID NO: 36 was designed as the enzyme substrate for trans-cleavage activity analysis; a single-stranded or double-stranded DNA containing SEQ ID NO: 36 was used as the targeted substrate, and the purified protein and the corresponding crRNA were prepared into the following reaction system as shown in the table below.

| Component | Volume |
|---|---|
| Cas protein | 1 μL (60 nM) |
| crRNA | 1 μL (120 nM) |
| ssDNA | 1 μL (30 nM) |
| 10X ssDNA Cleavage Buffer | 2 μL |

The above reaction system was placed in a PCR instrument and incubated at 25° C. for 10 min; then 2 μL of single-stranded DNA without target sequence was added and incubated at 37° C. for 1 h; 1 μL of RNase A was added and incubated at 37° C. for 30 min; 1 μL of Proteinase K was added and incubated at 55° C. for 30 min; 4 μL of 6×DNA loading buffer was added, and detection was performed by running 1.5% agarose gel. If the targeted substrate was dsDNA, it was necessary to synthesize a primer of about 90 nt without target sequence, which was diluted to 1 μM, packaged and stored at −20° C. as a random substrate in the trans-cleavage experiment. The dsDNA fragments in the in vitro dsDNA enzyme cleavage experiment were used as the targeted substrate, and the purified proteins and corresponding crRNA were prepared into the reaction system as shown in the following table.

| Component | Volume |
|---|---|
| Cas protein | 1 μL (200 nM) |
| crRNA | 1 μL (800 nM) |
| dsDNA | 1 μL (30 nM) |
| 10X ssDNA Cleavage Buffer | 2 μL |
| Nuclease-free water | Supplemented to 18 μL |

The above reaction system was placed in a PCR instrument and incubated at 37° C. for 15 min; (1) 2 μL (100 nM) of diluted random substrate ssDNA was added and incubated at 37° C. for 2 h; (2) 1 μL of RNase A was added and incubated at 37° C. for 30 min; (3) 1 μL of Proteinase K was added and incubated at 55° C. for 30 min; (4) 2×RNA Loading Buffer was added, and detection was performed by running 10% nucleic acid denaturing acrylamide gel.

Figure 4A:
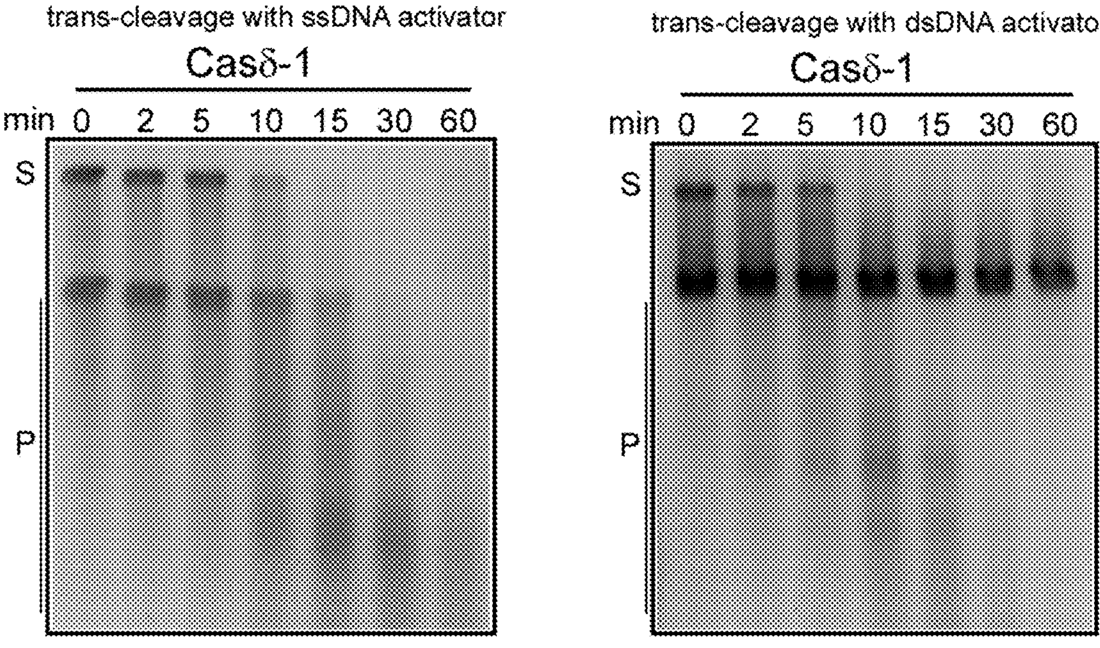
FIGS. 4A and B show the analysis results of the trans-cleavage activity of Casδ-1 in Example 4.
Figure 4B:
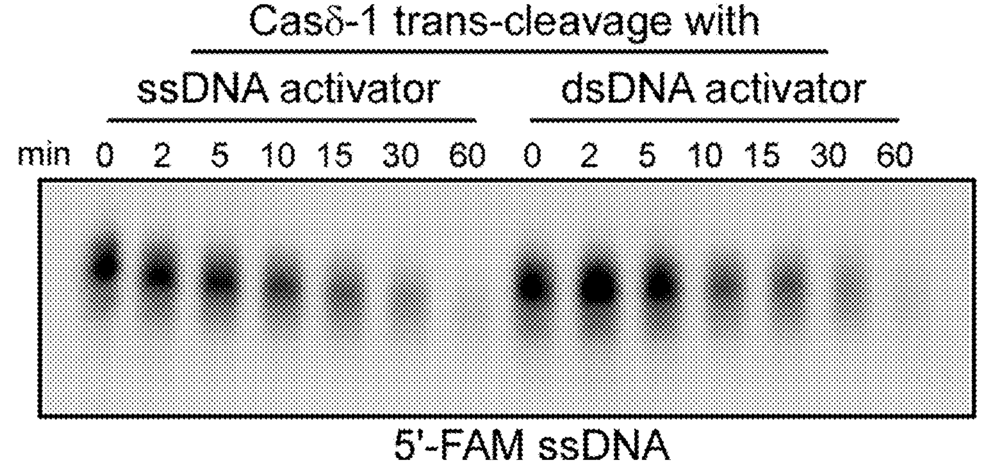

The experimental results were shown in FIG. 4A and FIG. 4B, and the experimental results confirmed that after the trans-cleavage activity of Casδ-1 protein was activated, both single-stranded DNA and double-stranded DNA substrates could be cleaved.

Example 5. Detection of Editing Activity of Casδ in Human Cells

In this example, 14 target sites, i.e., sg1 to sg14, were selected from the genome sequence of human HELA cells, and 14 guide sequences were designed for these target sites (the sequences were set forth in SEQ ID NO: 38 to SEQ ID NO: 51, respectively). Further, the eukaryotic expression vector containing Casδ-1 gene and the expression vector containing U6 promoter and guide RNA (containing the direct repeat sequence as set forth in SEQ ID NO: 7 and the editing guide sequence in human cells containing SEQ ID NO: 38 to SEQ ID NO: 51) were transferred into human HELA cells by liposome transfection, and cultured at 37° C. and 5% carbon dioxide concentration for 72 hours. DNA from all cells was extracted, and the sequences containing 200 bp of the target site were amplified. The PCR products were sent to Beijing Jiyinjia Medical Testing Laboratory Co., Ltd. for second-generation library construction and sequencing.

Figure 5:
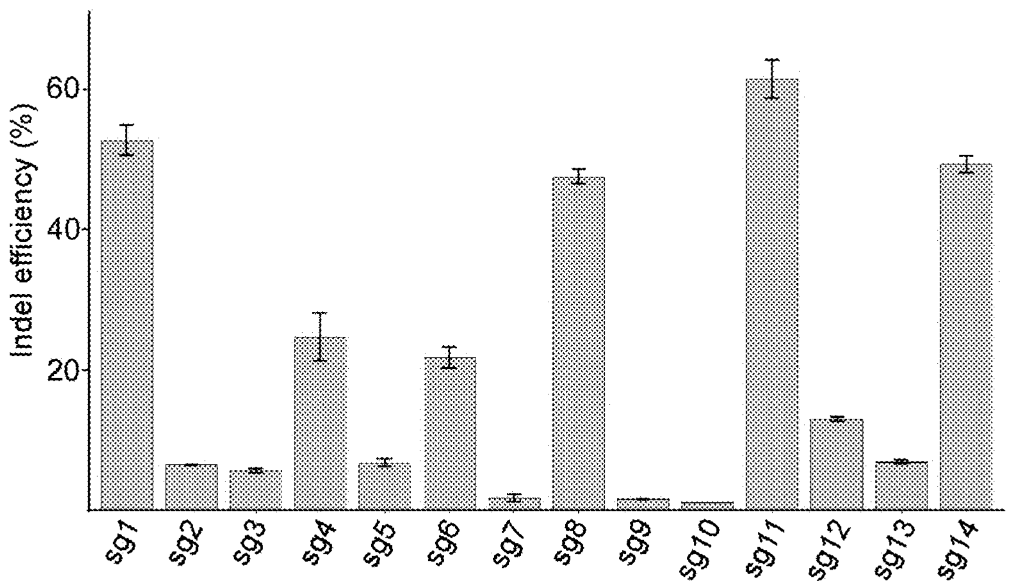
FIG. 5 shows the analysis of the editing activity of Casδ-1 at 14 target sites in HELA cells in Example 5.

The sequencing results were statistically analyzed by bioinformatics and the original target sequence. The results showed that Casδ-1 could effectively edit all 14 target sites, and the editing efficiency could reach up to about 60% (FIG. 5).

Example 6. Analysis of Editing Activity of Different PAM Recognition Sites of Casδ-1 in HELA Cells The PAM site recognized by Casδ-1 was identified as RYR (where R was A or G, and Y was T or C) by the experimental method of Example 3. In order to further confirm whether all recognized PAM sites had editing efficiency in eukaryotes, their editing efficiency was verified in HELA cells. Eight guide sequences were designed for these PAM recognition sites (the sequences were set forth in SEQ ID NO: 52 to SEQ ID NO: 59, respectively). The target sequences of different PAM recognition sites were selected within the 200 bp range of the AAVS1 gene, and the expression vector containing U6 promoter and guide RNA (containing the direct repeat sequence as set forth in SEQ ID NO: 7 and the editing guide sequence in human cells containing SEQ ID NO: 52 to SEQ ID NO: 59) was transferred into human HELA cells by liposome transfection and cultured at 37° C. and 5% carbon dioxide concentration for 72 hours.

Figure 6A:
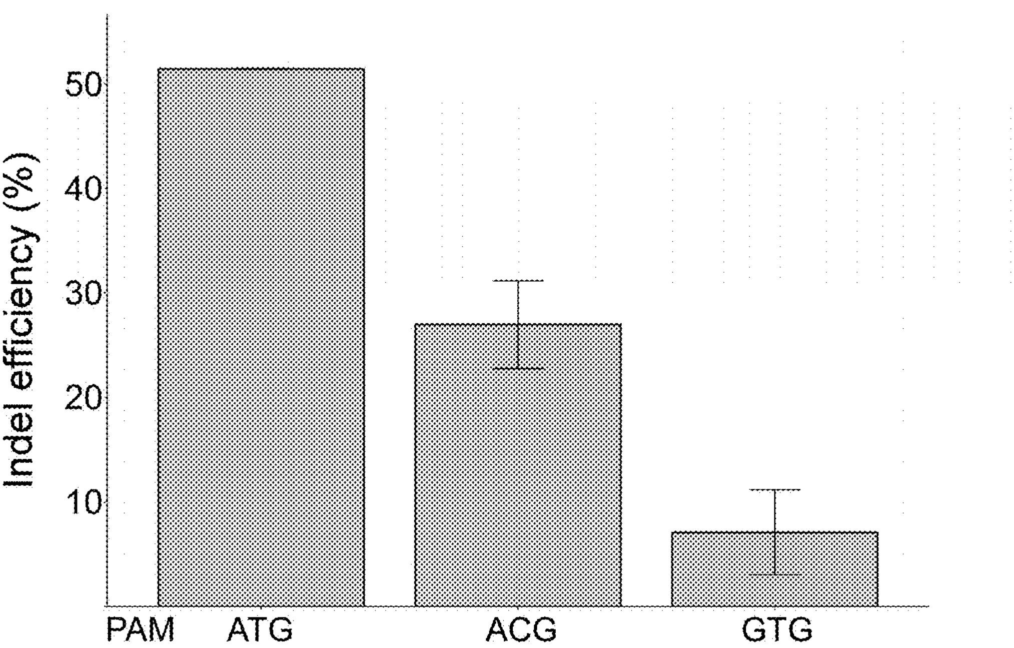
FIGS. 6A and B show the editing activity of Casδ-1 on AAVS1 targets at different PAM sites in HELA cells in Example 5.
Figure 6B:
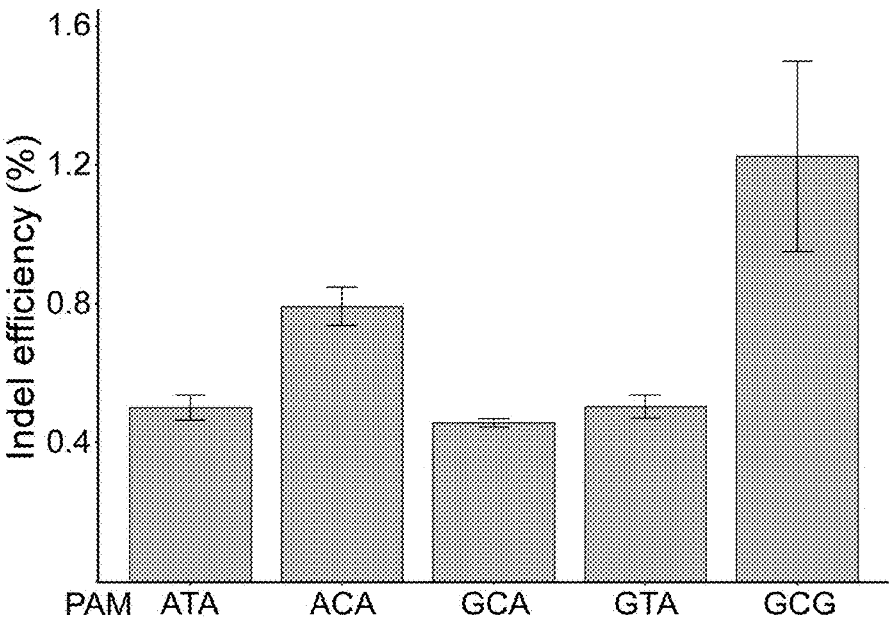

Through the second-generation library construction, second-generation sequencing and bioinformatics analysis of the transformed samples, it was found that the RYR PAM recognition sites of Casδ-1 all had different degrees of editing efficiency, among which the PAM recognition sites of ATG and ACG had higher editing efficiency (FIG. 6A and FIG. 6B).

Example 7. Analysis of Editing Activity of Casδ-1 with Different Repeat and Target Lengths In order to further verify the effects of direct repeat sequences (Repeat) and guide sequences (Target) with different lengths on editing efficiency, we selected Repeat (SEQ ID NO: 7 or 9 to 16) and Target (SEQ ID NO: 38) sequences with different lengths for combination, and Target (SEQ ID NO: 60 to 67) and Repeat (SEQ ID NO: 7) sequences with different lengths for combination, and confirmed their differences in editing efficiency in eukaryotes by animal cell transfection. The specific experimental procedures and steps were referred to Example 5.

Figure 7:
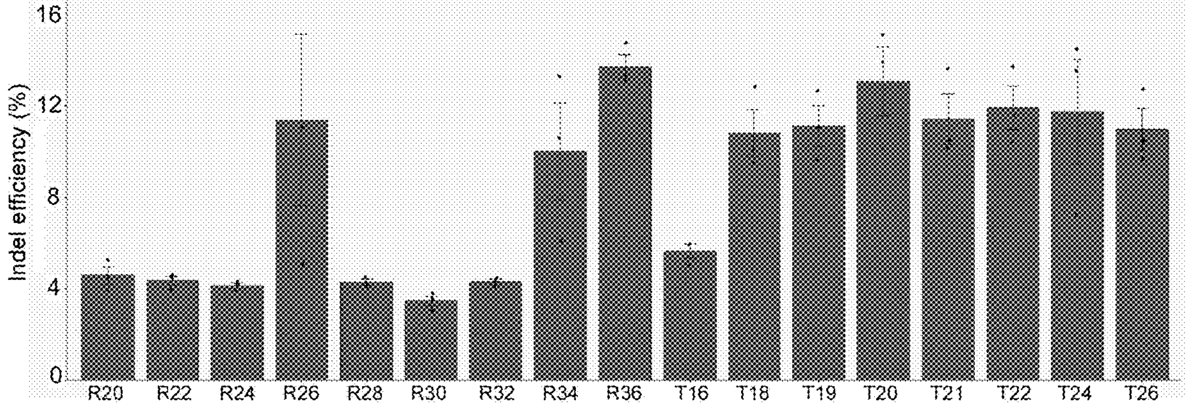
FIG. 7 shows the editing activity of Casδ-1 for crRNAs composed of direct repeat sequences and guide sequences with different lengths in HELA cells in Example 5, in which R represents direct repeat sequences, T represents guide sequences, and the numbers represent the number of bases in the corresponding sequence.

Through bioinformatics analysis, it was found that Repeat still retained a certain editing activity when 18 bases or less were cut off from the 5' end, and Target had editing activity in the range of 16 to 26 bases (FIG. 7).

Figure 8A:
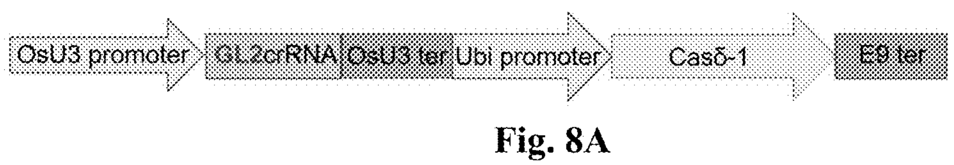
FIG. 8A shows the components in the expression vector with the protein of Casδ-1 constructed in Example 6.
Figure 8B:
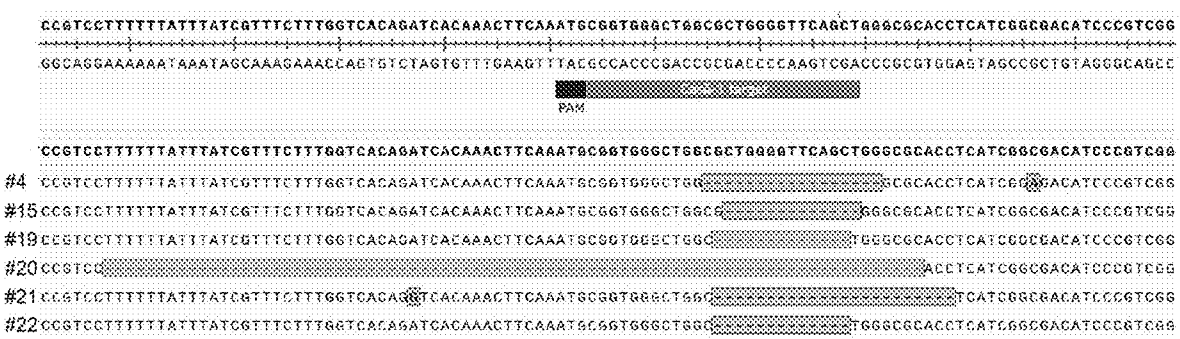
FIG. 8B shows the base sequences of Casδ-1-edited plants in maize in Example 6.

Example 8. Analysis of Editing Activity of Casδ-1 in Stable Genetic Transformation of Maize The target site of maize ZmGL2 gene was designed (wherein, the direct repeat sequence of Casδ-1 protein was set forth in SEQ ID NO: 7, and the guide sequence was set forth in SEQ ID NO: 37), and the crRNA sequence was ligated to the expression vector of OsU3 promoter, and the Ubi promoter and Casδ-1 protein coding sequence were constructed into the same expression vector (FIG. 8A). Positive plants were obtained by genetic transformation screening of maize callus, and the first-generation sequencing experimental method was used to analyze whether the ZmGL2 target site was edited, and a total of 6 mutants of different deletion types were obtained (FIG. 8B).

The above experiments confirmed that the Casδ-1 protein successfully edited the target site in maize.

Example 9. Analysis of Editing Activity of Casδ-1 Truncated Protein

In order to further reduce the protein size and improve the delivery efficiency, we deleted the 31 amino acids at the N-terminal of Casδ-1 to obtain a truncated form of Casδ-1, and named the truncated form Casδ-1D31 (the amino acid sequence was set forth in SEQ ID NO: 3, and the nucleotide sequence was set forth in SEQ ID NO: 6). Furthermore, the amino acid sequence of the Casδ-1D31-NLS fusion protein as set forth in SEQ ID NO: 30 was synthesized based on its amino acid sequence, and constructed into the pET30a vector by homologous recombination experimental method. The steps of prokaryotic protein purification and in vitro enzyme digestion experiment were the same as those described in Example 3.

Figure 9:
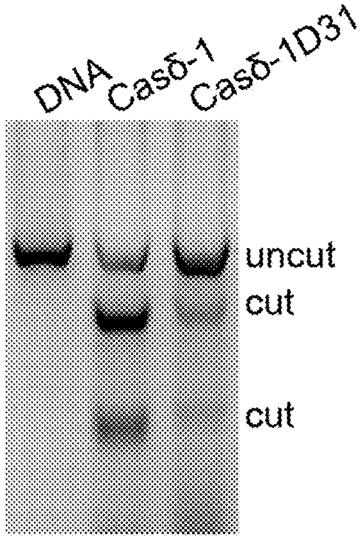
FIG. 9 shows the cleavage results of Casδ-1D31 on double-stranded DNA in Example 9.

The results of in vitro enzyme digestion verification showed that Casδ-1D31 still had double-stranded DNA cleavage activity (FIG. 9).

Although the specific models of the present invention have been described in detail, those skilled in the art will understand that various modifications and changes can be made to the details based on all the teachings that have been disclosed, and these changes are within the scope of protection of the present invention. All of the invention is given by the appended claims and any equivalents thereof.

What is claimed:

1. A fusion protein, which comprises a first protein and a second protein or polypeptide; wherein the first protein comprises or consists of a sequence as set forth in any one of SEQ ID NOs: 1, 2, and 3.

2. The fusion protein according to claim 1, wherein the second protein or polypeptide is selected from the group consisting of epitope tag, reporter gene sequence, nuclear localization signal (NLS) sequence, targeting moiety, transcription activation domain, transcription repression domain, nuclease domain, and any combination thereof.

3. The fusion protein according to claim 2, wherein the fusion protein has an amino acid sequence as set forth in any one of SEQ ID NOs: 28 to 30.

4. A composition or complex, which comprises:

(i) a first component, which is selected from the group consisting of: the fusion protein according to claim 1, a nucleotide sequence encoding the fusion protein, and any combination thereof; and (ii) a second component, which is a nucleotide sequence comprising a guide RNA, or a nucleotide sequence encoding the nucleotide sequence comprising the guide RNA;

wherein, the guide RNA comprises a direct repeat sequence and a guide sequence from the 5' to 3' direction, and the guide sequence is capable of hybridizing with a target sequence;

the guide RNA is capable of forming a complex with the fusion protein as described in (i).

5. The composition or complex according to claim 4, wherein:

(1) the guide sequence is linked to the 3' end of the direct repeat sequence;

(2) the guide sequence comprises a complementary sequence of the target sequence; or (3) the composition or complex does not comprise a trans-activating crRNA (tracrRNA).

6. The composition or complex according to claim 4, wherein, when the target sequence is DNA, the target sequence is located at the 3' end of a protospacer adjacent motif (PAM), and the PAM has a sequence shown as 5'-RYR, wherein R is A or G, and Y is T or C.

7. The composition or complex according to claim 4, wherein, the target sequence is a DNA or RNA sequence derived from a prokaryotic cell or a eukaryotic cell; or, the target sequence is a non-naturally occurring DNA or RNA sequence.

8. The composition or complex according to claim 4, wherein, the target sequence is present in a cell; or, the target sequence is present in a nucleic acid molecule in vitro.

9. The composition or complex according to claim 4, wherein, the fusion protein comprises one or more NLS sequences.

* * * * *

SEQUENCE LISTING

```
Sequence total quantity: 67
SEQ ID NO: 1            moltype = AA  length = 936
FEATURE                 Location/Qualifiers
source                  1..936
                        mol_type = protein
                        organism = synthetic construct
SEQUENCE: 1
MSKDGDKMKH SKQEVSEDKG VKKDPSVFRC QNLAILEMRE EVADYYADLQ ADYRHYLPLM  60
ILWGQNGFME PDETGLNFSA VLPSTAKTRC ENRYGAQIAA DLKLIADDLP SSLYAIFTND  120
YQPLTGVKKV GDRWKFVTSL NTVSDEEFAK KVKPLLRDYK GVTEEQWRRF REERVAGKTA  180
DQVWDDLDSI LRNPTLAALK KIHDKHMFRV KRPESKLYCD ALAHMLSSSY DSWKKINEAR  240
QLELQAMRDE QQGLLANKTT NSLYNLVCEF ADELESQNYG LTRRIFFIAR KEWEDEKSHY  300
LPVIKLLVTE KYLPLLQADN KTVSPAVKAW DICSTLKQRS PYIRFVPPTK DYPIPFGQTG  360
RGHKFTLKEE AGKVCFLVPG LTKDEMPLSG SHYFSSLRID KVGTDFKISF RHKTKIRSKK  420
SARVTVKQPR INGTVTEVGI LRRNGKFFLR VAYKIAYPQH NIDLKSYFAS AAPSTQKLEL  480
LPAQMRVAGV DLNISDPIVV SKADIFKGED GGPLSVLDYG SGKVVGEPVI ICKDTSRAGK  540
ISSLATKCRT LRDVIRNFRH SLHQGTPLPS KSLEFLQEVP VAQEDLKSPS PRYLIQTWIK  600
YIRTEMKRLH YKVWLDGYCH TSEAMRMLDL VDQVAFLMKS YENIHVKPGH KIPKKTTASL  660
KIRETSRTRF RLHVSRLVGA RVVRACEDCQ MIFLEDLSTG FSEGSNNSLA RLFSAGQLKN  720
SIVMAAEKVG KAVVFVCKDG TSIKDPVFGL HGLRPSKKTP GIPPDKKRLY VRRDGKIGYI  780
NADQAASLNV LLVGLSHSVA KYKFFVKDGK LQDDEEVAAQ QGKKPRKIGV RLERLLKMNF  840
DTPARLFFSL EKDQVVPCYE ATETPYTGWV YVYHDRLLTT RQRDQQVNQL AQEVKDLLRD  900
GVKIPKWDVI PDCDNSCLGF SPCLVLDDET AAVSVV                            936
```

-continued

```
SEQ ID NO: 2           moltype = AA  length = 867
FEATURE                Location/Qualifiers
source                 1..867
                       mol_type = protein
                       organism = synthetic construct
SEQUENCE: 2
MELKTTFCQS LKIKILPESH KLYYDELQAD LKKMRIFFAT HSGLNYSYKE DENDSEWKIA  60
SSKKSTLSPE AQRLIDIIAK GGIGAEHAYG IFYKDKKVSD KIRRDNSNCI FAMLLPNLVN  120
FEEEYKKRKS KLQLTKEEWE EYHKRCLAGE SVEVLWSEEI APKIGPNEAA RLASLAYHQF  180
PDSRHPADIT HCRALMSMVA DSFCSWVECH KLHREETEKL KTKLQEKIES CKEAYNLLLA  240
YSEDLYSRNY GLSARVLKAL IDNKSRCCFD IAFQIAEKYP ALMKIDEKTL FKAYNALKLH  300
WKIKRRKPFI SLPKIERDYQ VPFGLTGSRG KKFDVYVENK NIVVEIDGQK VETFSSHYFS  360
DMQISKIYGE KKNLKGFKLK FRHKLKDKKK EVYGEWIEAE LKEIKIKKDM ETGDFYLYLP  420
YTTTHNEKNL LLEKFFSYAD PLKETIFKNG KTELPNEFLG FGFDLNLSDP IAMAVAEFVR  480
DSSDGEIGAL DYGHGKLLDA SVLVCNSSLS KRINDLVGDN RKLIQAIRSY KNSLVTKEMD  540
EESGEWLKKA LGNAKYGNHR HQLQLVMSKL NKKSKKYWQE CRKNGHNDLS ENIALLKLLD  600
VQFSLHKSYN NIHIFDYKKQ IHSHKTDSKR ENFREFVTKQ FAATIVKHCK EVMAKYGREY  660
AVVFLEDLEM YFDADADNNS LIRLFAPGQL KKYIASALAK SKIGYVFIPP AGTSKTDPLT  720
SKIGFRATGK YYKQLGYLLN KSDLYVERNG VIGKINSDVA AAINILLKGV NHSIVPYRFL  780
NKHAGSEQKR LKRFEGEIGC DLKKMPKTRL YYLDGKIITE EEKNSLEEAL LAEIKHFLLS  840
KANIPEFDAI PGSNGTCKAF SVPRCLK                                    867

SEQ ID NO: 3           moltype = AA  length = 905
FEATURE                Location/Qualifiers
source                 1..905
                       mol_type = protein
                       organism = synthetic construct
SEQUENCE: 3
NLAILEMREE VADYYADLQA DYRHYLPLMI LWGQNGFMEP DETGLNFSAV LPSTAKTRCE  60
NRYGAQIAAD LKLIADDLPS SLYAIFTNDY QPLTGVKKVG DRWKFVTSLN TVSDEEFAKK  120
VKPLLRDYKG VTEEQWRRFR EERVAGKTAD QVWDDLDSIL RNPTLAALKK IHDKHMFRVK  180
RPESKLYCDA LAHMLSSSYD SWKKINEARQ LELQAMRDEQ QGLLANKTTN SLYNLVCEFA  240
DELESQNYGL TRRIFFIARK EWEDEKSHYL PVIKLLVTEK YLPLLQADNK TVSPAVKAWD  300
ICSTLKQRSP YIRFVPPTKD YPIPFGQTGR GHKFTLKEEA GKVCFLVPGL TKDEMPLSGS  360
HYFSSLRIDK VGTDFKISFR HKTKIRSKKS ARVTVKQPRI NGTVTEVGIL RRNGKFFLRV  420
AYKIAYPQHN IDLKSYFASA APSTQKLELL PAQMRVAGVD LNISDPIVVS KADIFKGEDG  480
GPLSVLDYGS GKVVGEPVII CKDTSRAGKI SSLATKCRTL RDVIRNFRHS LHQGTPLPSK  540
SLEFLQEVPV AQEDLKSPSP RYLIQTWIKY IRTEMKRLHY KVWLDGYCHT SEAMRMLDLV  600
DQVAFLMKSY ENIHVKPGHK IPKKTTASLK IRETSRTRFR LHVSRLVGAR VVRACEDCQM  660
IFLEDLSTGF SEGSNNSLAR LFSAGQLKNS IVMAAEKVGK AVVFVCKDGT SIKDPVFGLH  720
GLRPSKKTPG IPPDKKRLYV RRDGKIGYIN ADQAASLNVL LVGLSHSVAK YKFFVKDGKL  780
QDDEEVAAQQ GKKPRKIGVR LERLLKMNFD TPARLFFSLE KDQVVPCYEA TETPYTGWVY  840
VYHDRLLTTR QRDQQVNQLA QEVKDLLRDG VKIPKWDVIP DCDNSCLGFS PCLVLDDETA  900
AVSVV                                                            905

SEQ ID NO: 4           moltype = DNA  length = 2811
FEATURE                Location/Qualifiers
source                 1..2811
                       mol_type = other DNA
                       organism = synthetic construct
SEQUENCE: 4
atgtccaaag acggtgacaa gatgaagcac agcaaacaag aagtctctga ggacaaaggg  60
gtcaagaaag acccgtctgt cttccgctgt cagaacctcg cgattctgga gatgcgtgaa  120
gaagtcgctg attactacgc cgaccttcag gccgactacc gtcactactt gcccctgatg  180
atcctctggg gccagaacgg gttcatggag ccagacgaaa ctggtctgaa cttcagtgcc  240
gtcctgccat cgaccgcaaa aacacggtgc gagaaccgct acggtgcgca gattgcggct  300
gatctcaagt tgatcgccga cgatctcccg agcagtctct atgccatctt caccaacgac  360
taccagcccc tcaccggcgt gaagaaggtc ggcgacagat ggaagttcgt cacgtccctc  420
aacactgtca gcgacgaaga gttcgccaag aaggtgaagc cgctcctgcg tgactacaaa  480
ggcgttaccg aagagcagtg gcgtcgattt cgtgaagagc gtgtcgccgg caagacagcc  540
gatcaggtct gggacgacct tgacagcatt ctgcgaaacc cgacgctcgc ggccctgaag  600
aagatccacg acaagcacat gttccgggtc aagcgacccg agagcaaact ctactgtgac  660
gccctggctc acatgctgag ttccagctac gacagttgga agaaaatcaa cgaggcccgc  720
caactcgaac tccaagccat gcgtgacgag cagcagggct tgctcgccaa caagaccacg  780
aacagtctgt acaatctggt gtgcgagttc gccgacgaac tggagtcgca gaactacggt  840
ctgactcggc ggatcttctt catcgcccgc aaagagtggg aggacgaaaa gtcccattac  900
ctcccggtca tcaagctcct cgtcacggag aagtatctgc ccctgctcca ggcggataac  960
aagactgtca gccccgccgt caaggcgtgg gacatctgct ctactctgaa gcagaggtcg  1020
ccgtacatcc gcttcgtgcc tccgaccaag gactatccga tccccttcgg ccagacgggt  1080
cgcggacaca agttcacctt gaaagaggaa gccggaaagg tctgtttcct cgtacccggc  1140
ctgaccaagg acgagatgcc tctgtccggc tctcactact tctcaagcct ccgtatcgac  1200
aaggtcggca cagacttcaa gatctcgttc cgtcacaaga ccaagattcg cagcaaaaag  1260
tctgcgcgag tcaccgtcaa gcagcccagg atcaacggca ccgtcactga ggtcggcatc  1320
ctacgcagga acggcaagtt cttcctgcgt gtcgcttaca agatcgccta cccacagcac  1380
aacatcgacc tgaagagcta cttcgcctcg gcagcccccct ccacgcaaaa gctggagctt  1440
ctgccggctc aaatgagagt cgcgggcgtc gatctgaaca tcagcgaccc gattgtcgtc  1500
tccaaggccg acatcttcaa gggcgaagac ggcgggccgc tgtctgtgct ggactacggc  1560
tctggcaagg tggtaggtga gcctgtgatc atctgcaagg acaccagcag ggccgggaag  1620
atcagttccc tcgccacgaa atgccggacg ctacgcgacg tgatccgcaa ctttcgtcat  1680
```

```
tcactgcatc agggtacgcc cttgcccagc aagagtcttg aatttctcca agaagttccc  1740
gtggcgcagg aggacttgaa gtcgcccagc cctcgctatc tgatccagac gtggatcaag  1800
tacatcagga ccgagatgaa gcgacttcac tacaaggtct ggctcgacgg gtactgccac  1860
actagcgaag ccatgcggat gctcgatctg gtcgatcagg tcgcgttcct aatgaagtcg  1920
tatgagaaca tccacgtcaa accgggtcac aagatcccga agaagaccac tgcgtccctg  1980
aagattcgcg agacgagccg aacgcggttc aggctgcatg tctcccgact tgtcggtgcg  2040
cgagtggttc gtgcgtgcga ggactgccag atgatcttct tggaagatct ctcgacaggt  2100
ttctccgaag gcagcaataa ctcgttggcc cggctgtttt cggctggcca actgaagaac  2160
tccatcgtca tggcggcaga gaaggtcggc aaagccgtag tcttcgtgtg caaggacggt  2220
acgtctatca aagatcctgt tttcggtctg cacggcctgc ggccttccaa gaagacccca  2280
ggcattccgc cggacaagaa gcgtctctac gtccgtcgcg acggcaaaat cggctacatc  2340
aacgccgatc aggcggcttc gctgaatgtg ctgctggtgg ggctgtcgca ctccgtcgcc  2400
aagtacaagt tctttgtcaa ggacgggaag ctacaagacg acgaggaggt ggctgcccag  2460
caaggcaaga agccgcgtaa gatcggtgtt cgtctggaaa gactcctcaa gatgaacttc  2520
gacacccctg ccagactttt cttctcgctg gagaaagatc aggtggtgcc gtgctacgag  2580
gccacggaaa cgccttacac cggctgggtc tacgtctacc acgaccgact gctgaccacc  2640
cggcaacgtg atcagcaagt caatcaactc gcacaggaag tcaaggatct cctgcgggat  2700
ggtgtcaaaa ttcctaaatg ggacgtaatc ccagactgcg acaacagttg cctcggcttc  2760
tctccgtgtc tggtgcttga cgacgaaacc gccgctgttt ctgtggttta g            2811

SEQ ID NO: 5            moltype = DNA  length = 2604
FEATURE                 Location/Qualifiers
source                  1..2604
                        mol_type = other DNA
                        organism = synthetic construct
SEQUENCE: 5
atggaattga agacaacttt ttgtcagtca ctaaaaatta agatcctccc cgaaagccat  60
aagttgtatt acgatgagct gcaagccgac ctaaagaaga tgagaatctt cttcgcaacg  120
cactctgggc tcaactacag ctacaaggaa gatgaaaacg attcggaatg gaagatagcg  180
tcgtcaaaaa agagcacact ctcacctgaa gcccaaaggc ttattgacat catcgccaaa  240
ggcggtatag gagcagagca cgcctacgga atattttaca aggacaaaaa ggtgtcggac  300
aagatccggc gagataattc aaactgcatc ttcgccatgc tattacctaa cctcgtcaat  360
ttcgaggaag aatacaaaaa gaggaaaagt aagctccagc tcaccaagga agagtgggag  420
gagtaccata aacgatgtct tgcaggcgag agcgtggaag tcctgtggtc cgaggagatt  480
gctccaaaaa ttgggcctaa cgaagcggcg agactggcat cactcgcgta tcaccagttc  540
ccagattctc gtcatccggc ggacattacc cactgcaggg cgctcatgtc tatggtagca  600
gactcttttt gttcctgggt cgagtgccac aagctgcacc gtgaggaaac agagaaactc  660
aagacgaaat tacaggagaa gatagagagc tgcaaggagg catacaatct gctactcgct  720
tattccgaag acctgtacag taggaattat ggtctgagtg ccagggtttt gaaggcactt  780
attgacaaca aatcccggtg ctgcttcgac atagcctttc agatcgcgga gaaatatcct  840
gcactgatga agattgatga aaagaccctg ttcaaggcct acaacgccct aaagctccac  900
tggaaaataa aacgacgcaa gccgttcatc tcgctgccca agatcgagag ggactaccag  960
gtgccctttg gactcacagg aagcagaggc aagaagttcg acgtctatgt ggaaaacaag  1020
aatattgtgg tcgagatcga cggccagaaa gtcgaaacct tcagctctca ctatttctct  1080
gatatgcaga tctccaagat ttacggtgaa aagaaaaatt tgaagggatt caagttgaaa  1140
ttccgccaca agctgaagga caagaagaag gaggtttatg gagagtggat tgaggcggag  1200
ctgaaggaaa tcaagattaa gaaagacatg gagacaggcg acttctacct gtatctccca  1260
tacactacaa cgcataatga gaaaaactta ttgctcgaga agttcttttc ctacgccgat  1320
ccacttaagg agactatttt taagaacgga aagacggagc ttccaaatga atttctaggc  1380
ttcggcttcg atttgaacct ttccgacccg attgcgatgg cggttgccga gtttgttcgg  1440
gactcatcag atggtgagat tggcgccctc gactatggtc acggtaagct cctcgacgct  1500
agtgttttgg tctgcaactc atcactatca aagcgcatca atgacctggt tggagacaat  1560
agaaagctga tccaagctat tagatcgtac aagaactcgc tagtaactaa ggaaatggac  1620
gaggagagtg gcgagtggct taaaaaagct ctaggcaatg caaagtacgg caaccatagg  1680
catcagcttc aactggtcat gtctaagctg aacaaaaaaa gcaaaaagta ctggcaggaa  1740
tgtcgcaaga acggccacaa cgatctttcc gaaaatattg cactattaaa gttgttggac  1800
gtgcagttct ctttgcataa aagctataac aacatacaca tctttgatta caaaaaacaa  1860
attcacagcc ataagactga ctccaaaagg gagaatttcc gtgaatttgt gacgaagcaa  1920
tttgcggcta ccatagtaaa gcattgcaag gaggtgatgg ctaaatatgg cagagagtac  1980
gccgttgtct ttttggagga cctggagatg tactttgatg ctgatgctga taacaattct  2040
ctgatccggc tttttgcacc cggccaattg aagaagtaca tcgcctccgc tctggctaag  2100
agcaagatag gttatgtgtt catccctcct gctgggacaa gtaagaccga cccgttaact  2160
tcgaaaattg gattcagggc taccggaaaa tactacaagc agctgggcta tctgcttaat  2220
aagtccgacc tctacgtgga gcgcaacggg gttatcggga agatcaacag tgatgtagct  2280
gcggcgataa atattctctt aaagggcgtg aaccactcaa tcgtgccgta ccgcttcctg  2340
aataaacatg ctgggtctga acagaagcgc ctcaaacgtt ttgaagggga gatcggttgt  2400
gatctgaaaa agatgccaaa gacacgcctc tactatcttg acggaaaaat catcactgaa  2460
gaggagaaga acagcctgga ggaagcgcta ctcgctgaga tcaagcactt ccttctgtcg  2520
aaggccaaca ttccggagtt tgatgcaata ccggggagca atggcacctg caaagccttc  2580
tccgttccac gctgccttaa gtga                                        2604

SEQ ID NO: 6            moltype = DNA  length = 2718
FEATURE                 Location/Qualifiers
source                  1..2718
                        mol_type = other DNA
                        organism = synthetic construct
SEQUENCE: 6
aacctcgcga ttctggagat gcgtgaagaa gtcgctgatt actacgccga ccttcaggcc  60
gactaccgtc actacttgcc cctgatgatc ctctggggcc agaacgggtt catggagcca  120
```

```
gacgaaactg gtctgaactt cagtgccgtc ctgccatcga ccgcaaaaac acggtgcgag  180
aaccgctacg gtgcgcagat tgcggctgat ctcaagttga tcgccgacga tctcccgagc  240
agtctctatg ccatcttcac caacgactac cagcccctca ccggcgtgaa gaaggtcggc  300
gacagatgga agttcgtcac gtccctcaac actgtcagcg acgaagagtt cgccaagaag  360
gtgaagccgc tcctgcgtga ctacaaaggc gttaccgaag agcagtggcg tcgatttcgt  420
gaagagcgtg tcgccggcaa gacagccgat caggtctggg acgaccttga cagcattctg  480
cgaaacccga cgctcgcggc cctgaagaag atccacgaca agcacatgtt ccgggtcaag  540
cgacccgaga gcaaactcta ctgtgacgcc ctggctcaca tgctgagttc cagctacgac  600
agttggaaga aaatcaacga ggcccgccaa ctcgaactcc aagccatgcg tgacgagcag  660
cagggcttgc tcgccaacaa gaccacgaac agtctgtaca atctggtgtg cgagttcgcc  720
gacgaactgg agtcgcagaa ctacggtctg actcggcgga tcttcttcat cgcccgcaaa  780
gagtgggagg acgaaaagtc ccattacctc ccggtcatca agctcctcgt cacggagaag  840
tatctgcccc tgctccaggc ggataacaag actgtcagcc ccgccgtcaa ggcgtgggac  900
atctgctcta ctctgaagca gaggtcgccg tacatccgct tcgtgcctcc gaccaaggac  960
tatccgatcc ccttcggcca gacgggtcgc ggacacaagt tcaccttgaa agaggaagcc  1020
ggaaaggtct gtttcctcgt acccggcctg accaaggacg agatgcctct gtccggctct  1080
cactacttct caagcctccg tatcgacaag gtcggcacag acttcaagat ctcgttccgt  1140
cacaagacca agattcgcag caaaaagtct gcgcgagtca ccgtcaagca gcccaggatc  1200
aacggcaccg tcactgaggt cggcatccta cgcaggaacg gcaagttctt cctgcgtgtc  1260
gcttacaaga tcgcctaccc acagcacaac atcgacctga agagctactt cgcctcggca  1320
gccccctcca cgcaaaagct ggagcttctg ccggctcaaa tgagagtcgc gggcgtcgat  1380
ctgaacatca gcgacccgat tgtcgtctcc aaggccgaca tcttcaaggg cgaagacggc  1440
gggccgctgt ctgtgctgga ctacggctct ggcaaggtgg taggtgagcc tgtgatcatc  1500
tgcaaggaca ccagcagggc cgggaagatc agttccctcg ccacgaaatg ccggacgcta  1560
cgcgacgtga tccgcaactt tcgtcattca ctgcatcagg gtacgccctt gcccagcaag  1620
agtcttgaat ttctccaaga agttcccgtg gcgcaggagg acttgaagtc gcccagccct  1680
cgctatctga tccagacgtg gatcaagtac atcaggaccg agatgaagcg acttcactac  1740
aaggtctggc tcgacgggta ctgccacact agcgaagcca tgcggatgct cgatctggtc  1800
gatcaggtcg cgttcctaat gaagtcgtat gagaacatcc acgtcaaacc gggtcacaag  1860
atcccgaaga agaccactgc gtccctgaag attcgcgaga cgagccgaac gcggttcagg  1920
ctgcatgtct cccgacttgt cggtgcgcga gtggttcgtg cgtgcgagga ctgccagatg  1980
atcttcttgg aagatctctc gacaggtttc tccgaaggca gcaataactc gttggcccgg  2040
ctgttttcgg ctggccaact gaagaactcc atcgtcatgg cggcagagaa ggtcggcaaa  2100
gccgtagtct tcgtgtgcaa ggacggtacg tctatcaaag atcctgtttt cggtctgcac  2160
ggcctgcggc cttccaagaa gaccccaggc attccgccgg acaagaagcg tctctacgtc  2220
cgtcgcgacg gcaaaatcgg ctacatcaac gccgatcagg cggcttcgct gaatgtgctg  2280
ctggtggggc tgtcgcactc cgtcgccaag tacaagttct ttgtcaagga cgggaagcta  2340
caagacgacg aggaggtggc tgcccagcaa ggcaagaagc cgcgtaagat cggtgttcgt  2400
ctggaaagac tcctcaagat gaacttcgac accoctgcca gacttttctt ctcgctggag  2460
aaagatcagg tggtgccgtg ctacgaggcc acggaaacgc cttacaccgg ctgggtctac  2520
gtctaccacg accgactgct gaccacccgg caacgtgatc agcaagtcaa tcaactcgca  2580
caggaagtca aggatctcct gcgggatggt gtcaaaattc ctaaatggga cgtaatccca  2640
gactgcgaca acagttgcct cggcttctct ccgtgtctgg tgcttgacga cgaaaccgcc  2700
gctgtttctg tggtttag                                                2718

SEQ ID NO: 7            moltype = RNA  length = 36
FEATURE                 Location/Qualifiers
source                  1..36
                        mol_type = other RNA
                        organism = synthetic construct
SEQUENCE: 7
gtgctgacga ccagcactag atggtcgttc aggcac                             36

SEQ ID NO: 8            moltype = RNA  length = 36
FEATURE                 Location/Qualifiers
source                  1..36
                        mol_type = other RNA
                        organism = synthetic construct
SEQUENCE: 8
gtgctgaaca gggtcgctag gcgttgttca aggcac                             36

SEQ ID NO: 9            moltype = RNA  length = 34
FEATURE                 Location/Qualifiers
source                  1..34
                        mol_type = other RNA
                        organism = synthetic construct
SEQUENCE: 9
gctgacgacc agcactagat ggtcgttcag gcac                               34

SEQ ID NO: 10           moltype = RNA  length = 32
FEATURE                 Location/Qualifiers
source                  1..32
                        mol_type = other RNA
                        organism = synthetic construct
SEQUENCE: 10
tgacgaccag cactagatgg tcgttcaggc ac                                 32

SEQ ID NO: 11           moltype = RNA  length = 30
FEATURE                 Location/Qualifiers
```

```
source                  1..30
                        mol_type = other RNA
                        organism = synthetic construct
SEQUENCE: 11
acgaccagca ctagatggtc gttcaggcac                                      30

SEQ ID NO: 12           moltype = RNA  length = 28
FEATURE                 Location/Qualifiers
source                  1..28
                        mol_type = other RNA
                        organism = synthetic construct
SEQUENCE: 12
gaccagcact agatggtcgt tcaggcac                                        28

SEQ ID NO: 13           moltype = RNA  length = 26
FEATURE                 Location/Qualifiers
source                  1..26
                        mol_type = other RNA
                        organism = synthetic construct
SEQUENCE: 13
ccagcactag atggtcgttc aggcac                                          26

SEQ ID NO: 14           moltype = RNA  length = 24
FEATURE                 Location/Qualifiers
source                  1..24
                        mol_type = other RNA
                        organism = synthetic construct
SEQUENCE: 14
agcactagat ggtcgttcag gcac                                            24

SEQ ID NO: 15           moltype = RNA  length = 22
FEATURE                 Location/Qualifiers
source                  1..22
                        mol_type = other RNA
                        organism = synthetic construct
SEQUENCE: 15
cactagatgg tcgttcaggc ac                                              22

SEQ ID NO: 16           moltype = RNA  length = 20
FEATURE                 Location/Qualifiers
source                  1..20
                        mol_type = other RNA
                        organism = synthetic construct
SEQUENCE: 16
ctagatggtc gttcaggcac                                                 20

SEQ ID NO: 17           moltype = DNA  length = 36
FEATURE                 Location/Qualifiers
source                  1..36
                        mol_type = other DNA
                        organism = synthetic construct
SEQUENCE: 17
gtgctgacga ccagcactag atggtcgttc aggcac                               36

SEQ ID NO: 18           moltype = DNA  length = 37
FEATURE                 Location/Qualifiers
source                  1..37
                        mol_type = other DNA
                        organism = synthetic construct
SEQUENCE: 18
gtgctgaaca gggtcgctag gcgttgttca aggcacg                              37

SEQ ID NO: 19           moltype = DNA  length = 34
FEATURE                 Location/Qualifiers
source                  1..34
                        mol_type = other DNA
                        organism = synthetic construct
SEQUENCE: 19
gctgacgacc agcactagat ggtcgttcag gcac                                 34

SEQ ID NO: 20           moltype = DNA  length = 32
FEATURE                 Location/Qualifiers
source                  1..32
                        mol_type = other DNA
                        organism = synthetic construct
SEQUENCE: 20
tgacgaccag cactagatgg tcgttcaggc ac                                   32

SEQ ID NO: 21           moltype = DNA  length = 30
```

```
FEATURE                Location/Qualifiers
source                 1..30
                       mol_type = other DNA
                       organism = synthetic construct
SEQUENCE: 21
acgaccagca ctagatggtc gttcaggcac                         30

SEQ ID NO: 22          moltype = DNA  length = 28
FEATURE                Location/Qualifiers
source                 1..28
                       mol_type = other DNA
                       organism = synthetic construct
SEQUENCE: 22
gaccagcact agatggtcgt tcaggcac                           28

SEQ ID NO: 23          moltype = AA  length = 26
FEATURE                Location/Qualifiers
source                 1..26
                       mol_type = protein
                       organism = synthetic construct
SEQUENCE: 23
CCAGCACTAG ATGGTCGTTC AGGCAC                             26

SEQ ID NO: 24          moltype = DNA  length = 24
FEATURE                Location/Qualifiers
source                 1..24
                       mol_type = other DNA
                       organism = synthetic construct
SEQUENCE: 24
agcactagat ggtcgttcag gcac                               24

SEQ ID NO: 25          moltype = DNA  length = 22
FEATURE                Location/Qualifiers
source                 1..22
                       mol_type = other DNA
                       organism = synthetic construct
SEQUENCE: 25
cactagatgg tcgttcaggc ac                                 22

SEQ ID NO: 26          moltype = DNA  length = 20
FEATURE                Location/Qualifiers
source                 1..20
                       mol_type = other DNA
                       organism = synthetic construct
SEQUENCE: 26
ctagatggtc gttcaggcac                                    20

SEQ ID NO: 27          moltype = AA  length = 11
FEATURE                Location/Qualifiers
source                 1..11
                       mol_type = protein
                       organism = synthetic construct
SEQUENCE: 27
SRADPKKKRK V                                             11

SEQ ID NO: 28          moltype = AA  length = 979
FEATURE                Location/Qualifiers
source                 1..979
                       mol_type = protein
                       organism = synthetic construct
SEQUENCE: 28
MGPKKKRKVM DYKDHDGDYK DHDIDYKDDD DKMSKDGDKM KHSKQEVSED KGVKKDPSVF  60
RCQNLAILEM REEVADYYAD LQADYRHYLP LMILWGQNGF MEPDETGLNF SAVLPSTAKT  120
RCENRYGAQI AADLKLIADD LPSSLYAIFT NDYQPLTGVK KVGDRWKFVT SLNTVSDEEF  180
AKKVKPLLRD YKGVTEEQWR RFREERVAGK TADQVWDDLD SILRNPTLAA LKKIHDKHMF  240
RVKRPESKLY CDALAHMLSS SYDSWKKINE ARQLELQAMR DEQQGLLANK TTNSLYNLVC  300
EFADELESQN YGLTRRIFFI ARKEWEDEKS HYLPVIKLLV TEKYLPLLQA DNKTVSPAVK  360
AWDICSTLKQ RSPYIRFVPP TKDYPIPFGQ TGRGHKFTLK EEAGKVCFLV PGLTKDEMPL  420
SGSHYFSSLR IDKVGTDFKI SFRHKTKIRS KKSARVTVKQ PRINGTVTEV GILRRNGKFF  480
LRVAYKIAYP QHNIDLKSYF ASAAPSTQKL ELLPAQMRVA GVDLNISDPI VVSKADIFKG  540
EDGGPLSVLD YGSGKVVGEP VIICKDTSRA GKISSLATKC RTLRDVIRNF RHSLHQGTPL  600
PSKSLEFLQE VPVAQEDLKS PSPRYLIQTW IKYIRTEMKR LHYKVWLDGY CHTSEAMRML  660
DLVDQVAFLM KSYENIHVKP GHKIPKKTTA SLKIRETSRT RFRLHVSRLV GARVVRACED  720
CQMIFLEDLS TGFSEGSNNS LARLFSAGQL KNSIVMAAEK VGKAVVFVCK DGTSIKDPVF  780
GLHGLRPSKK TPGIPPDKKR LYVRRDGKIG YINADQAASL NVLLVGLSHS VAKYKFFVKD  840
GKLQDDEEVA AQQGKKPRKI GVRLERLLKM NFDTPARLFF SLEKDQVVPC YEATETPYTG  900
WVYVYHDRLL TTRQRDQQVN QLAQEVKDLL RDGVKIPKWD VIPDCDNSCL GFSPCLVLDD  960
ETAAVSVVSR ADPKKKRKV                                     979
```

```
SEQ ID NO: 29           moltype = AA  length = 910
FEATURE                 Location/Qualifiers
source                  1..910
                        mol_type = protein
                        organism = synthetic construct
SEQUENCE: 29
MGPKKKRKVM DYKDHDGDYK DHDIDYKDDD DKMELKTTFC QSLKIKILPE SHKLYYDELQ  60
ADLKKMRIFF ATHSGLNYSY KEDENDSEWK IASSKKSTLS PEAQRLIDII AKGGIGAEHA  120
YGIFYKDKKV SDKIRRDNSN CIFAMLLPNL VNFEEEYKKR KSKLQLTKEE WEEYHKRCLA  180
GESVEVLWSE EIAPKIGPNE AARLASLAYH QFPDSRHPAD ITHCRALMSM VADSFCSWVE  240
CHKLHREETE KLKTKLQEKI ESCKEAYNLL LAYSEDLYSR NYGLSARVLK ALIDNKSRCC  300
FDIAFQIAEK YPALMKIDEK TLFKAYNALK LHWKIKRRKP FISLPKIERD YQVPFGLTGS  360
RGKKFDVYVE NKNIVVEIDG QKVETFSSHY FSDMQISKIY GEKKNLKGFK LKFRHKLKDK  420
KKEVYGEWIE AELKEIKIKK DMETGDFYLY LPYTTTHNEK NLLLEKFFSY ADPLKETIFK  480
NGKTELPNEF LGFGFDLNLS DPIAMAVAEF VRDSSDGEIG ALDYGHGKLL DASVLVCNSS  540
LSKRINDLVG DNRKLIQAIR SYKNSLVTKE MDEESGEWLK KALGNAKYGN HRHQLQLVMS  600
KLNKKSKKYW QECRKNGHND LSENIALLKL LDVQFSLHKS YNNIHIFDYK KQIHSHKTDS  660
KRENFREFVT KQFAATIVKH CKEVMAKYGR EYAVVFLEDL EMYFDADADN NSLIRLFAPG  720
QLKKYIASAL AKSKIGYVFI PPAGTSKTDP LTSKIGFRAT GKYYKQLGYL LNKSDLYVER  780
NGVIGKINSD VAAAINILLK GVNHSIVPYR FLNKHAGSEQ KRLKRFEGEI GCDLKKMPKT  840
RLYYLDGKII TEEEKNSLEE ALLAEIKHFL LSKANIPEFD AIPGSNGTCK AFSVPRCLKS  900
RADPKKKRKV                                                         910

SEQ ID NO: 30           moltype = AA  length = 948
FEATURE                 Location/Qualifiers
source                  1..948
                        mol_type = protein
                        organism = synthetic construct
SEQUENCE: 30
MGPKKKRKVM DYKDHDGDYK DHDIDYKDDD DKNLAILEMR EEVADYYADL QADYRHYLPL  60
MILWGQNGFM EPDETGLNFS AVLPSTAKTR CENRYGAQIA ADLKLIADDL PSSLYAIFTN  120
DYQPLTGVKK VGDRWKFVTS LNTVSDEEFA KKVKPLLRDY KGVTEEQWRR FREERVAGKT  180
ADQVWDDLDS ILRNPTLAAL KKIHDKHMFR VKRPESKLYC DALAHMLSSS YDSWKKINEA  240
RQLELQAMRD EQQGLLANKT TNSLYNLVCE FADELESQNY GLTRRIFFIA RKEWEDEKSH  300
YLPVIKLLVT EKYLPLLQAD NKTVSPAVKA WDICSTLKQR SPYIRFVPPT KDYPIPFGQT  360
GRGHKFTLKE EAGKVCFLVP GLTKDEMPLS GSHYFSSLRI DKVGTDFKIS FRHKTKIRSK  420
KSARVTVKQP RINGTVTEVG ILRRNGKFFL RVAYKIAYPQ HNIDLKSYFA SAAPSTQKLE  480
LLPAQMRVAG VDLNISDPIV VSKADIFKGE DGGPLSVLDY GSGKVVGEPV IICKDTSRAG  540
KISSLATKCR TLRDVIRNFR HSLHQGTPLP SKSLEFLQEV PVAQEDLKSP SPRYLIQTWI  600
KYIRTEMKRL HYKVWLDGYC HTSEAMRMLD LVDQVAFLMK SYENIHVKPG HKIPKKTTAS  660
LKIRETSRTR FRLHVSRLVG ARVVRACEDC QMIFLEDLST GFSEGSNNSL ARLFSAGQLK  720
NSIVMAAEKV GKAVVFVCKD GTSIKDPVFG LHGLRPSKKT PGIPPDKKRL YVRRDGKIGY  780
INADQAASLN VLLVGLSHSV AKYKFFVKDG KLQDDEEVAA QQGKKPRKIG VRLERLLKMN  840
FDTPARLFFS LEKDQVVPCY EATETPYTGW VYVYHDRLLT TRQRDQQVNQ LAQEVKDLLR  900
DGVKIPKWDV IPDCDNSCLG FSPCLVLDDE TAAVSVVSRA DPKKKRKV              948

SEQ ID NO: 31           moltype = DNA  length = 2967
FEATURE                 Location/Qualifiers
source                  1..2967
                        mol_type = other DNA
                        organism = synthetic construct
SEQUENCE: 31
atgggaccaa agaagaagag aaaggttatg gattacaagg accacgacgg agactataaa  60
gatcatgaca tcgattataa ggatgatgat gacaagatgt ctaaagacgg ggacaaaatg  120
aaacactcca agcaagaagt ttccgaggac aaaggcgtca agaaagatcc gtccgtgttt  180
cgatgccaga acctcgccat actcgagatg agggaggagg tcgctgacta ttacgcagac  240
cttcaggctg actaccggca ctacctgcct ctgatgattc tgtgggggca aaatggcttt  300
atggagccag atgaaacggg cctcaacttc agcgccgtcc tgccgtcgac cgcgaaaaca  360
cgctgtgaga ataggtatgg tgcccagatt gcagccgacc tgaaactcat cgcagatgat  420
ctgccgtcta gcctgtatgc tatattcacg aatgattacc agcctttaac tggcgtgaag  480
aaggttggtg accgttggaa gtttgtgact tcattgaaca ccgtgtcgga tgaggaattt  540
gcaaagaaag tcaaacccct ccttcgcgac tacaaaggtg tcacagagga gcagtggcgt  600
cgtttccgtg aggaacgagt tgctgggaaa acagccgacc aggtttggga cgatctcgat  660
tccatcttga ggaacccgac gcttgccgcc ctcaaaaaga ttcatgacaa gcacatgttc  720
agagttaaga ggccggagtc aaagctgtat tgtgatgcat tggcgcatat gctctcatct  780
tcatatgatt catggaaaaa gatcaatgaa gcacgtcagt tggaactaca ggccatgaga  840
gacgaacaac aaggcctgct ggcaaataaa actactaact ctctttacaa tctggtctgt  900
gagttcgcgg atgagcttga atcacaaaac tacggcctga cccgaaggat attcttcatc  960
gccaggaaag agtgggagga tgaaaagtcg cactaccttc ctgtgatcaa actcttggtg  1020
accgagaagt atcttccact tctgcaggcg gataacaaaa cagtttctcc ggcggttaag  1080
gcgtgggata tttgcagcac gttgaagcag cgcagtccat atatacggtt cgttcctccc  1140
acaaaagact atccgattcc atttggccag acaggtaggg gacacaagtt tacactcaag  1200
gaggaggccg ggaaggtttg cttcctggtt ccaggactca ccaaggatga aatgccactc  1260
tcgggctccc actatttctc tagtctgcga attgacaagg tcggcacaga cttcaagatc  1320
agcttccgcc ataagacgaa gattcgaagc aagaagtcag ctagagtgac cgtaaaacaa  1380
cctcggatca acggcaccgt tacggaggtg ggtatcctgc gtcgcaacgg caagtttttc  1440
ttacgggttg cgtacaagat tgcttacccg caacacaaca ttgatcttaa gagctacttc  1500
gccagcgccg ccccttccac tcagaagctc gagctgctcc ctgctcagat gagggtggcg  1560
ggagtcgatt tgaacatttc cgatcccatc gtcgtatcca aagctgatat ttttaaggga  1620
```

```
gaggatggag ggccattatc ggtcttggac tacggatctg gcaaggtagt gggcgagccc  1680
gtcatcatct gtaaggatac aagtcgcgca ggtaaaatct cctcgctcgc gactaagtgc  1740
cgcaccttaa gagacgtcat tcggaatttc cgccactctc tccatcaggg aacccccccta  1800
cccagtaaga gcctggagtt tctgcaggag gtgccagtgg cccaggagga cctaaaatcg  1860
ccatccccca ggtatctcat acagacctgg ataaagtata tcagaacaga gatgaagcgc  1920
ttgcattata aagtgtggtt ggacggctac tgccacacat ctgaagctat gcgtatgctt  1980
gatctagttg atcaggtcgc cttcctcatg aagtcatacg aaaacataca tgtgaagccg  2040
ggccataaaa ttcccaagaa aactaccgcg agtctcaaga ttagggaaac atccaggacg  2100
agatttagac tgcatgtatc caggttggtc ggggccaggg tggtccgcgc ctgtgaagat  2160
tgtcagatga tcttcctgga agacttgtcg accggcttct cagaaggtag caacaatagc  2220
ctcgcgcggc tgtttagcgc cggccagctg aagaatagta tagtgatggc ggcggagaag  2280
gtgggtaaag ctgttgtatt tgtctgcaag gatggaacta gcataaagga ccctgtcttc  2340
ggtttacacg gccttcggcc gtcgaaaaag accccaggca tccctccgga taaaaaaaga  2400
ctttatgtga gacgggatgg taagattggg tacatcaatg ctgatcaagc tgcaagtctg  2460
aatgtactat tggtaggtct gagccatagt gtggccaagt acaagttctt cgtcaaagat  2520
ggtaagttgc aggatgacga agaggtggcg gcacaacaag gaaagaagcc taggaagatt  2580
ggcgttcgcc tggaaagact actaaagatg aattttgata ccccggcccg ccttttttt  2640
agcctggaga aggaccaggt ggttccgtgc tacgaggcga ctgagacgcc ttacacgggt  2700
tgggtgtacg tctaccatga caggcttctc acaacacgcc agagggacca acaggtgaat  2760
caacttgccc aagaggtgaa agacttactt agggacgggg tgaagatccc taaatgggac  2820
gtgatcccag actgcgacaa cagttgcctc gggttctctc cctgcctggt gcttgacgac  2880
gagactgctg ctgtctcagt tgttggatct gggagcaagc ggcccgcagc aacgaaaaag  2940
gcagggcaag caaaaaagaa gaaatga                                    2967
```

```
SEQ ID NO: 32          moltype = DNA  length = 2760
FEATURE                Location/Qualifiers
source                 1..2760
                       mol_type = other DNA
                       organism = synthetic construct
SEQUENCE: 32
atgggtccga aaaagaagcg gaaagttatg gattataagg atcatgatgg cgactataag  60
gatcatgaca tagattataa agatgatgac gacaaaatgg aattgaagac aactttttgt  120
cagtcactaa aaattaagat cctccccgaa agccataagt tgtattacga tgagctgcaa  180
gccgacctaa agaagatgag aatcttcttc gcaacgcact ctgggctcaa ctacagctac  240
aaggaagatg aaaacgattc ggaatggaag atagcgtcgt caaaaaagag cacactctca  300
cctgaagccc aaaggcttat tgacatcatc gccaaaggcg gtataggagc agagcacgcc  360
tacggaatat tttacaagga caaaaaggtg tcggacaaga tccggcgaga taattcaaac  420
tgcatcttcg ccatgctatt acctaacctc gtcaatttcg aggaagaata caaaaagagg  480
aaaagtaagc tccagctcac caaggaagag tgggaggagt accataaacg atgtcttgca  540
ggcgagagcg tggaagtcct gtggtccgag gagattgctc caaaaattgg gcctaacgaa  600
gcggcgagac tggcatcact cgcgtatcac cagttcccag attctcgtca tccggcggac  660
attacccact gcagggcgct catgtctatg gtagcagact ctttttgttc ctgggtcgag  720
tgccacaagc tgcaccgtga ggaaacagag aaactcaaga cgaaattaca ggagaagata  780
gagagctgca aggaggcata caatctgcta ctcgcttatt ccgaagacct gtacagtagg  840
aattatggtc tgagtgccag ggttttgaag gcacttattg acaacaaatc ccggtgctgc  900
ttcgacatag cctttcagat cgcggagaaa tatcctgcac tgatgaagat tgatgaaaag  960
accctgttca aggcctacaa cgccctaaag ctccactgga aataaaacg acgcaagccg  1020
ttcatctcgc tgcccaagat cgagagggac taccaggtgc cctttggact cacaggaagc  1080
agaggcaaga agttcgacgt ctatgtggaa aacaagaata ttgtggtcga gatcgacggc  1140
cagaaagtcg aaaccttcag ctctcactat ttctctgata tgcagatctc caagatttac  1200
ggtgaaaaga aaaatttgaa gggattcaag ttgaaattcc gccacaagct gaaggacaag  1260
aagaaggagg tttatggaga gtggattgag gcggagctga aggaaatcaa gattaagaaa  1320
gacatggaga caggcgactt ctacctgtat ctcccataca ctacaacgca taatgagaaa  1380
aacttattgc tcgagaagtt cttttcctac gccgatccac ttaaggagac tatttttaag  1440
aacggaaaga cggagcttcc aaatgaattt ctaggcttcg gcttcgattt gaacctttcc  1500
gacccgattg cgatggcggt tgccgagttt gttcgggact catcagatgg tgagattggc  1560
gccctcgact atggtcacgg taagctcctc gacgctagtg ttttggtctg caactcatca  1620
ctatcaaagc gcatcaatga cctggttgga gacaatagaa agctgatcca agctattaga  1680
tcgtacaaga actcgctagt aactaaggaa atggacgagg agagtggcga gtggcttaaa  1740
aaagctctag gcaatgcaaa gtacggcaac cataggcatc agcttcaact ggtcatgtct  1800
aagctgaaca aaaaaagcaa aaagtactgg caggaatgtc gcaagaacgg ccacaacgat  1860
ctttccgaaa atattgcact attaaagttg ttggacgtgc agttctcttt gcataaaagc  1920
tataacaaca tacacatctt tgattacaaa aaacaaattc acagccataa gactgactcc  1980
aaaagggaga atttccgtga atttgtgacg aagcaatttg cggctaccat agtaaagcat  2040
tgcaaggagg tgatggctaa atatggcaga gagtacgccg ttgtcttttt ggaggacctg  2100
gagatgtact ttgatgctga tgctgataac aattctctga tccggctttt tgcacccggc  2160
caattgaaga agtacatcgc ctccgctctg gctaagagca agataggtta tgtgttcatc  2220
cctcctgctg ggacaagtaa gaccgacccg ttaacttcga aaattggatt cagggctacc  2280
ggaaaatact acaagcagct gggctatctg cttaataagt ccgacctcta cgtggagcgc  2340
aacggggtta tcgggaagat caacagtgat gtagctgcgg cgataaatat tctcttaaag  2400
ggcgtgaacc actcaatcgt gccgtaccgc ttcctgaata aacatgctgg gtctgaacag  2460
aagcgcctca aacgttttga aggggagatc ggttgtgatc tgaaaaagat gccaaagaca  2520
cgcctctact atcttgacgg aaaaatcatc actgaagagg agaagaacag cctggaggaa  2580
gcgctactcg ctgagatcaa gcacttcctt ctgtcgaagg ccaacattcc ggagtttgat  2640
gcaataccgg ggagcaatgg cacctgcaaa gccttctccg ttccacgctg ccttaagggc  2700
agcgggagca agcggcccgc cgcgaccaaa aaagcggggc aagccaagaa gaaaaagtga  2760
```

```
SEQ ID NO: 33          moltype = DNA  length = 2874
FEATURE                Location/Qualifiers
```

```
source                  1..2874
                        mol_type = other DNA
                        organism = synthetic construct
SEQUENCE: 33
atgggaccaa agaagaagag aaaggttatg gattacaagg accacgacgg agactataaa  60
gatcatgaca tcgattataa ggatgatgat gacaagaacc tcgccatact cgagatgagg  120
gaggaggtcg ctgactatta cgcagacctt caggctgact accggcacta cctgcctctg  180
atgattctgt gggggcaaaa tggctttatg gagccagatg aaacgggcct caacttcagc  240
gccgtcctgc cgtcgaccgc gaaaacacgc tgtgagaata ggtatggtgc ccagattgca  300
gccgacctga aactcatcgc agatgatctg ccgtctagcc tgtatgctat attcacgaat  360
gattaccagc ctttaactgg cgtgaagaag gttggtgacc gttggaagtt tgtgacttca  420
ttgaacaccg tgtcggatga ggaatttgca aagaaagtca aacccctcct tcgcgactac  480
aaaggtgtca cagaggagca gtggcgtcgt ttccgtgagg aacgagttgc tgggaaaaca  540
gccgaccagg tttgggacga tctcgattcc atcttgagga acccgacgct tgccgccctc  600
aaaaagattc atgacaagca catgttcaga gttaagaggc cggagtcaaa gctgtattgt  660
gatgcattgg cgcatatgct ctcatcttca tatgattcat ggaaaaagat caatgaagca  720
cgtcagttgg aactacaggc catgagagac gaacaacaag gcctgctggc aaataaaact  780
actaactctc tttacaatct ggtctgtgag ttcgcggatg agcttgaatc acaaaactac  840
ggcctgaccc gaaggatatt cttcatcgcc aggaaagagt gggaggatga aaagtcgcac  900
taccttcctg tgatcaaact cttggtgacc gagaagtatc ttccacttct gcaggcggat  960
aacaaaacag tttctccggc ggttaaggcg tgggatattt gcagcacgtt gaagcagcgc  1020
agtccatata tacggttcgt tcctcccaca aaagactatc cgattccatt tggccagaca  1080
ggtaggggac acaagtttac actcaaggag gaggccggga aggtttgctt cctggttcca  1140
ggactcacca aggatgaaat gccactctcg ggctcccact atttctctag tctgcgaatt  1200
gacaaggtcg gcacagactt caagatcagc ttccgccata agacgaagat tcgaagcaag  1260
aagtcagcta gagtgaccgt aaaacaacct cggatcaacg gcaccgttac ggaggtgggt  1320
atcctgcgtc gcaacggcaa gtttttctta cgggttgcgt acaagattgc ttacccgcaa  1380
cacaacattg atcttaagag ctacttcgcc agcgccgccc cttccactca gaagctcgag  1440
ctgctccctg ctcagatgag ggtggcggga gtcgatttga acatttccga tcccatcgtc  1500
gtatccaaag ctgatatttt taagggagag gatggagggc cattatcggt cttggactac  1560
ggatctggca aggtagtggg cgagcccgtc atcatctgta aggatacaag tcgcgcaggt  1620
aaaatctcct cgctcgcgac taagtgccgc accttaagag acgtcattcg gaatttccgc  1680
cactctctcc atcagggaac ccccctaccc agtaagagcc tggagtttct gcaggaggtg  1740
ccagtggccc aggaggacct aaaatcgcca tcccccaggt atctcataca gacctggata  1800
aagtatatca gaacagagat gaagcgcttg cattataaag tgtggttgga cggctactgc  1860
cacacatctg aagctatgcg tatgcttgat ctagttgatc aggtcgcctt cctcatgaag  1920
tcatacgaaa acatacatgt gaagccgggc cataaaattc ccaagaaaac taccgcgagt  1980
ctcaagatta gggaaacatc caggacgaga tttagactgc atgtatccag gttggtcggg  2040
gccagggtgg tccgcgcctg tgaagattgt cagatgatct tcctggaaga cttgtcgacc  2100
ggcttctcag aaggtagcaa caatagcctc gcgcggctgt ttagcgccgg ccagctgaag  2160
aatagtatag tgatggcggc ggagaaggtg ggtaaagctg ttgtatttgt ctgcaaggat  2220
ggaactagca taaaggaccc tgtcttcggt ttacacggcc ttcggccgtc gaaaaagacc  2280
ccaggcatcc ctccggataa aaaaagactt tatgtgagac gggatggtaa gattgggtac  2340
atcaatgctg atcaagctgc aagtctgaat gtactattgg taggtctgag ccatagtgtg  2400
gccaagtaca agttcttcgt caaagatggt aagttgcagg atgacgaaga ggtggcggca  2460
caacaaggaa agaagcctag gaagattggc gttcgcctgg aaagactact aaagatgaat  2520
tttgataccc cggcccgcct ttttttagc ctggagaagg accaggtggt tccgtgctac  2580
gaggcgactg agacgcctta cacgggttgg gtgtacgtct accatgacag gcttctcaca  2640
acacgccaga gggaccaaca ggtgaatcaa cttgcccaag aggtgaaaga cttacttagg  2700
gacggggtga agatccctaa atgggacgtg atcccagact gcgacaacag ttgcctcggg  2760
ttctctccct gcctggtgct tgacgacgag actgctgctg tctcagttgt tggatctggg  2820
agcaagcggc ccgcagcaac gaaaaaggca gggcaagcaa aaaagaagaa atga        2874

SEQ ID NO: 34           moltype = DNA  length = 35
FEATURE                 Location/Qualifiers
source                  1..35
                        mol_type = other DNA
                        organism = synthetic construct
SEQUENCE: 34
nnnnnnnngg tataacaact tcgacgagct ctaca                              35

SEQ ID NO: 35           moltype = RNA  length = 27
FEATURE                 Location/Qualifiers
source                  1..27
                        mol_type = other RNA
                        organism = synthetic construct
SEQUENCE: 35
ggtataacaa cttcgacgag ctctaca                                       27

SEQ ID NO: 36           moltype = RNA  length = 27
FEATURE                 Location/Qualifiers
source                  1..27
                        mol_type = other RNA
                        organism = synthetic construct
SEQUENCE: 36
ggtataacaa cttcgacgag ctctaca                                       27

SEQ ID NO: 37           moltype = RNA  length = 26
FEATURE                 Location/Qualifiers
```

```
source                  1..26
                        mol_type = other RNA
                        organism = synthetic construct
SEQUENCE: 37
cggtgggctg gcgctggggt tcagct                                            26

SEQ ID NO: 38           moltype = RNA  length = 26
FEATURE                 Location/Qualifiers
source                  1..26
                        mol_type = other RNA
                        organism = synthetic construct
SEQUENCE: 38
gagccagaga ggatcctggg agggag                                            26

SEQ ID NO: 39           moltype = RNA  length = 26
FEATURE                 Location/Qualifiers
source                  1..26
                        mol_type = other RNA
                        organism = synthetic construct
SEQUENCE: 39
tgactttgtc acagcccaag atagtt                                            26

SEQ ID NO: 40           moltype = RNA  length = 26
FEATURE                 Location/Qualifiers
source                  1..26
                        mol_type = other RNA
                        organism = synthetic construct
SEQUENCE: 40
aaacccagac acatagcaat tcagga                                            26

SEQ ID NO: 41           moltype = RNA  length = 26
FEATURE                 Location/Qualifiers
source                  1..26
                        mol_type = other RNA
                        organism = synthetic construct
SEQUENCE: 41
ctgaggggct gctggtttgg ctggtg                                            26

SEQ ID NO: 42           moltype = RNA  length = 26
FEATURE                 Location/Qualifiers
source                  1..26
                        mol_type = other RNA
                        organism = synthetic construct
SEQUENCE: 42
gagatgccag cagaagttgg gcagaa                                            26

SEQ ID NO: 43           moltype = RNA  length = 26
FEATURE                 Location/Qualifiers
source                  1..26
                        mol_type = other RNA
                        organism = synthetic construct
SEQUENCE: 43
gggcagagtg gagatggtgg ggacaa                                            26

SEQ ID NO: 44           moltype = RNA  length = 26
FEATURE                 Location/Qualifiers
source                  1..26
                        mol_type = other RNA
                        organism = synthetic construct
SEQUENCE: 44
actagggtgg gcaaccacaa acccac                                            26

SEQ ID NO: 45           moltype = RNA  length = 26
FEATURE                 Location/Qualifiers
source                  1..26
                        mol_type = other RNA
                        organism = synthetic construct
SEQUENCE: 45
tgtacagaag gctgaaagga gagaac                                            26

SEQ ID NO: 46           moltype = RNA  length = 26
FEATURE                 Location/Qualifiers
source                  1..26
                        mol_type = other RNA
                        organism = synthetic construct
SEQUENCE: 46
cggtaccagt ttagcacgaa gctctc                                            26

SEQ ID NO: 47           moltype = RNA  length = 26
```

```
FEATURE                 Location/Qualifiers
source                  1..26
                        mol_type = other RNA
                        organism = synthetic construct
SEQUENCE: 47
ccaccattgt ctttcctagc ggaatg                                       26

SEQ ID NO: 48           moltype = RNA  length = 26
FEATURE                 Location/Qualifiers
source                  1..26
                        mol_type = other RNA
                        organism = synthetic construct
SEQUENCE: 48
aagcactgtg ggtacgaagg aaatga                                       26

SEQ ID NO: 49           moltype = RNA  length = 26
FEATURE                 Location/Qualifiers
source                  1..26
                        mol_type = other RNA
                        organism = synthetic construct
SEQUENCE: 49
tgtcacaaag taaggattct gatgtg                                       26

SEQ ID NO: 50           moltype = RNA  length = 26
FEATURE                 Location/Qualifiers
source                  1..26
                        mol_type = other RNA
                        organism = synthetic construct
SEQUENCE: 50
ctgttgttga aggcgtttgc acatgc                                       26

SEQ ID NO: 51           moltype = RNA  length = 26
FEATURE                 Location/Qualifiers
source                  1..26
                        mol_type = other RNA
                        organism = synthetic construct
SEQUENCE: 51
tctgcaggcc agatgagggc tccaga                                       26

SEQ ID NO: 52           moltype = RNA  length = 26
FEATURE                 Location/Qualifiers
source                  1..26
                        mol_type = other RNA
                        organism = synthetic construct
SEQUENCE: 52
gagccagaga ggatcctggg agggag                                       26

SEQ ID NO: 53           moltype = RNA  length = 26
FEATURE                 Location/Qualifiers
source                  1..26
                        mol_type = other RNA
                        organism = synthetic construct
SEQUENCE: 53
gaccactgtg tgggggtaaa ggacct                                       26

SEQ ID NO: 54           moltype = RNA  length = 26
FEATURE                 Location/Qualifiers
source                  1..26
                        mol_type = other RNA
                        organism = synthetic construct
SEQUENCE: 54
cccccatttc ctggagccat ctctct                                       26

SEQ ID NO: 55           moltype = RNA  length = 26
FEATURE                 Location/Qualifiers
source                  1..26
                        mol_type = other RNA
                        organism = synthetic construct
SEQUENCE: 55
aaccttagag gttctggcaa ggagag                                       26

SEQ ID NO: 56           moltype = RNA  length = 26
FEATURE                 Location/Qualifiers
source                  1..26
                        mol_type = other RNA
                        organism = synthetic construct
SEQUENCE: 56
agcaaacctt agaggttctg gcaagg                                       26
```

-continued

```
SEQ ID NO: 57          moltype = RNA  length = 26
FEATURE                Location/Qualifiers
source                 1..26
                       mol_type = other RNA
                       organism = synthetic construct
SEQUENCE: 57
atggagccag agaggatcct gggagg                                        26

SEQ ID NO: 58          moltype = RNA  length = 26
FEATURE                Location/Qualifiers
source                 1..26
                       mol_type = other RNA
                       organism = synthetic construct
SEQUENCE: 58
ggagggaagg gggggatgcg tgacct                                        26

SEQ ID NO: 59          moltype = RNA  length = 26
FEATURE                Location/Qualifiers
source                 1..26
                       mol_type = other RNA
                       organism = synthetic construct
SEQUENCE: 59
tgacctgccc ggttctcagt ggccac                                        26

SEQ ID NO: 60          moltype = RNA  length = 26
FEATURE                Location/Qualifiers
source                 1..26
                       mol_type = other RNA
                       organism = synthetic construct
SEQUENCE: 60
gagccagaga ggatcctggg agggag                                        26

SEQ ID NO: 61          moltype = RNA  length = 24
FEATURE                Location/Qualifiers
source                 1..24
                       mol_type = other RNA
                       organism = synthetic construct
SEQUENCE: 61
gagccagaga ggatcctggg aggg                                          24

SEQ ID NO: 62          moltype = RNA  length = 22
FEATURE                Location/Qualifiers
source                 1..22
                       mol_type = other RNA
                       organism = synthetic construct
SEQUENCE: 62
gagccagaga ggatcctggg ag                                            22

SEQ ID NO: 63          moltype = RNA  length = 21
FEATURE                Location/Qualifiers
source                 1..21
                       mol_type = other RNA
                       organism = synthetic construct
SEQUENCE: 63
gagccagaga ggatcctggg a                                             21

SEQ ID NO: 64          moltype = RNA  length = 20
FEATURE                Location/Qualifiers
source                 1..20
                       mol_type = other RNA
                       organism = synthetic construct
SEQUENCE: 64
gagccagaga ggatcctggg                                               20

SEQ ID NO: 65          moltype = RNA  length = 19
FEATURE                Location/Qualifiers
source                 1..19
                       mol_type = other RNA
                       organism = synthetic construct
SEQUENCE: 65
gagccagaga ggatcctgg                                                19

SEQ ID NO: 66          moltype = RNA  length = 18
FEATURE                Location/Qualifiers
source                 1..18
                       mol_type = other RNA
                       organism = synthetic construct
SEQUENCE: 66
gagccagaga ggatcctg                                                 18
```

```
SEQ ID NO: 67           moltype = RNA  length = 16
FEATURE                 Location/Qualifiers
source                  1..16
                        mol_type = other RNA
                        organism = synthetic construct
SEQUENCE: 67
gagccagaga ggatcc                                                  16
```